United States Patent [19]

Milner

[11] Patent Number: 4,670,431
[45] Date of Patent: * Jun. 2, 1987

[54] BETA-LACTAM ANTIBACTERIAL AGENTS

[75] Inventor: Peter H. Milner, Horsham, England

[73] Assignee: Beecham Group p.l.c., England

[*] Notice: The portion of the term of this patent subsequent to Sep. 3, 2002 has been disclaimed.

[21] Appl. No.: 572,195

[22] Filed: Jan. 19, 1984

[30] Foreign Application Priority Data

Jan. 21, 1983 [GB] United Kingdom ............... 8301690
Jan. 24, 1983 [GB] United Kingdom ............... 8301877
Jan. 24, 1983 [GB] United Kingdom ............... 8301875
Jan. 24, 1983 [GB] United Kingdom ............... 8301879
Jul. 13, 1983 [GB] United Kingdom ............... 8318884

[51] Int. Cl.$^4$ ............... A61K 31/43; A61K 31/545; C07D 501/18; C07D 499/00; C07D 499/44; C07D 499/46; C07D 501/00
[52] U.S. Cl. ............... 514/194; 514/201; 540/219; 540/221; 540/312; 540/314; 540/328
[58] Field of Search ............... 260/239.1, 245.2 R; 424/246, 271; 544/22, 26, 28; 514/194, 201; 540/219, 221, 312, 314, 328, 215

[56] References Cited

U.S. PATENT DOCUMENTS 4,255,330 3/1981 Christensen et al. ............ 260/239.1
4,308,259 12/1981 Bentley ............ 424/200

OTHER PUBLICATIONS

Chemical Abstracts 80:120975v, Clark et al., (1974).
Chemical Abstracts 75:118332m, Laundon et al., (1971).
Chemical Abstracts 76:3882u, Bain et al., (1972).
Huffman, Chemical Abstracts, vol. 53, Column 14089h to 14090d, (1959), Abstracting *J. Org. Chem.* 23, 727-9, (1958).

Primary Examiner—Natalie Trousof
Assistant Examiner—Vera C. Clarke
Attorney, Agent, or Firm—Jacobs & Jacobs

[57] ABSTRACT

A compound having the partial structure (A):

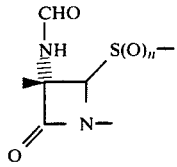

(A)

wherein n is 1 or 2.

19 Claims, No Drawings

BETA-LACTAM ANTIBACTERIAL AGENTS

This invention relates to a class of novel β-lactam derivatives which have antibacterial activity and/or β-lactamase inhibitory activity. The invention also relates to a process for the preparation of such compounds, intermediates for use in the preparation of the compounds and to pharmaceutical compositions comprising the antibacterially active compounds.

Accordingly the present invention provides a compound having the partial structure (A):

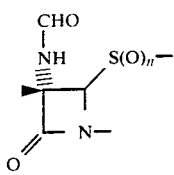
(A)

wherein n is 1 or 2.

More particularly the present invention provides a compound of formula (I) or a salt thereof:

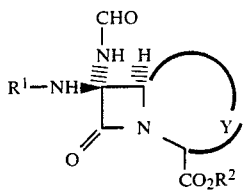
(I)

wherein $R^1$ is hydrogen, an acyl group, in particular that of an antibacterially active penicillin or cephalosporin, or an amino-protecting group; $R^2$ is hydrogen or a readily removable carboxyl protecting group; and Y is:

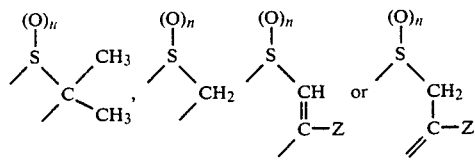

wherein n is 1 or 2 and Z represents hydrogen, halogen, or an organic group such as $C_{1-4}$ alkoxy, $-CH_2Q$ or $-CH=CH-Q$ wherein Q represents hydrogen, halogen, hydroxy, mercapto, cyano, carboxy, carboxylic ester, carbamoyloxy, $C_{1-4}$ alkyloxy, acyloxy, aryl, a heterocyclyl group bonded via carbon, a heterocyclylthio group or a nitrogen containing heterocyclic group bonded via nitrogen. Preferably n is 1.

When used herein the term 'halogen' unless otherwise defined is suitably fluorine, chlorine, bromine, and iodine, preferably chlorine and bromine.

When used herein the term 'carboxylic ester' unless otherwise defined suitably includes $C_{1-6}$ alkyl esters.

When used herein the term 'acyloxy' unless otherwise defined suitably includes $C_{1-6}$ alkylcarbonyloxy groups.

When used herein the term 'aryl' unless otherwise defined suitably includes phenyl and naphthyl, preferably phenyl, optionally substituted with up to five halogen, $C_{1-6}$ alkyl, $C_{1-6}$ alkoxy, halo($C_{1-6}$)alkyl, hydroxy, amino, carboxy, $C_{1-6}$ alkoxycarbonyl, or $C_{1-6}$ alkoxycarbonyl-($C_{1-6}$)-alkyl groups, or $C_{1-6}$ alkoxycarbonyloxy.

When used herein the term 'heterocyclyl' unless otherwise defined suitably includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$alkoxy-carbonyl($C_{1-6}$)alkyl, aryl, oxo, carboxyalkyl or optionally substituted amino($C_{1-6}$)alkyl groups.

The compounds of the present invention may contain both an amino group and/or a carboxyl group and may, therefore, exist as the zwitterion or may form salts with suitable acids or bases.

The formamido group can exist in two preferred conformations, those wherein the hydrogen atoms of the —NH—CHO are, cis- or trans-, of which the cis-conformation normally predominates.

Suitably Y is $-SO-C(CH_3)_2-$, $-SO_2-C(CH_3)_2-$, $-SO-CH_2-CZ=$; or $-SO-CH=CZ-$.

Preferred values for Y in the compounds of formula (I) are $-SO-C(CH_3)_2-$ and $-SO-CH_2-CZ=$, ie when the compound of formula (I) is a derivative of a penicillin or cephalosporin.

A further preferred value for Y is $-SO-CH=CZ-$ wherein Z is as hereinbefore defined.

Those compounds of the formula (I) wherein $R^1$ is a hydrogen group, or an amino-protecting group are mainly useful as intermediates in the preparation of compounds of the formula (I) wherein $R^1$ is an acyl group, in particular those found in antibacterially active penicillins or cephalosporins.

Those compounds of the formula (I) wherein $R^2$ is a readily removable carboxyl protecting group or a non-pharmaceutically acceptable salt are primarily useful as intermediates in the preparation of compounds of the formula (I) wherein $R^2$ is a free carboxyl group or a pharmaceutically acceptable salt thereof. Also included within the readily removable carboxyl protecting groups $R^2$ are pharmaceutically acceptable in vivo hydrolysable ester groups.

Those compounds of the formula (I) wherein Y is $-SO-CH=CZ-$ are primarily useful as intermediates in the preparation of compounds of the formula (I) wherein Y is $-SO-CH_2-CZ=$.

Since the β-lactam antibiotic compounds of the present invention are intended for use in pharmaceutical compositions it will readily be understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical it will readily be understood that the substantially pure form is preferred as for the β-lactam antibiotic compounds. Preferably, whenever possible, the compounds of the present invention are obtained in crystalline form.

Suitable amino-protecting groups $R^1$ are those well-known in the art which may be removed under conventional conditions without disruption of the remainder of the molecule.

Examples of amino-protecting groups for $R^1$ include benzyl optionally substituted in the phenyl ring by one or two substituents selected from $C_{1-4}$ alkyl, $C_{1-4}$ alkoxy, trifluoromethyl, halogen or nitro; $C_{1-4}$ alkoxycarbonyl, for example tert-butoxycarbonyl; benzyloxycarbonyl optionally substituted as for benzyl above; allyloxycarbonyl; trityl or trichloroethoxycarbonyl.

Preferred examples of N-protecting groups within $R^1$ include those listed above which are removable under acid conditions optionally in the presence of a group IIb metal.

Examples of suitable pharmaceutically acceptable in vivo hydrolysable ester groups include those which break down readily in the human body to leave the parent acid or its salt. Suitable ester groups of this type include those of part formula (i), (ii) and (iii):

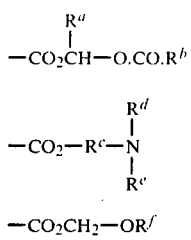

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups; $R^c$ represents $C_{1-6}$ alkylene optionally substituted with a methyl or ethyl group-$R^d$ and $R^e$ independently represent $C_{1-6}$ alkyl; $R^f$ represents $C_{1-6}$ alkyl. Examples of suitable in vivo hydrolysable ester groups include for example acyloxyalkyl groups such as acetoxymethyl, pivaloyloxymethyl, α-acetoxyethyl and α-pivaloyloxy-ethyl groups; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

Suitable readily removable carboxyl protecting groups for the group —$CO_2R^2$ in formula (I) include ester derivatives of the carboxylic acid. The derivative is preferably one which may readily be cleaved.

Suitable ester-forming carboxyl-protecting groups are those which may be removed under conventional conditions. Such groups for $R^2$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR< where R< is aryl or heterocyclic, or an in vivo hydrolysable ester radical such as defined above.

The carboxyl group may be regenerated from any of the above esters by usual methods appropriate to the particular $R^2$ group, for example, acid—and base—catalysed hydrolysis, or by enzymically—catalysed hydrolysis, or by hydrogenolysis.

Suitable pharmaceutically acceptable salts of the carboxy group of the compound of formula (I) include metal salts eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine, cycloalkylamines such as dicyclohexylamine, or with procaine, dibenzylamine, N,N'-dibenzylethylenediamine, 1-ephenamine, N-ethylpiperidine, N-benzyl-β-phenethylamine, dehydroabiethylamine, N,N'-bisdehydroabiethylamine, ethylenediamine, or bases of the pyridine type such as pyridine, collidine or quinoline, or other amines which have been used to form salts with known penicillins and cephalosporins. Other suitable salts include the lithium and silver salt.

Some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Suitable values for Q in the compounds of the formula (I) include the acetoxy, heterocyclylthio group, and nitrogen containing heterocyclic group bonded via nitrogen.

More suitably Q represents the acetoxy or heterocyclylthio group.

The heterocyclylthio group may suitably be represented by the formula:

—S—Het wherein 'Het' is a five or six membered heterocyclic ring containing from 1 to 4 atoms selected from N, O, and S unsubstituted or substituted with one or two groups selected from $C_{1-6}$ alkyl, $C_{1-6}$ alkoxy, hydroxyalkyl, $C_{1-6}$ alkenyl, alkoxyalkyl, sulphonylalkyl, carbamoylalkyl, trifluoromethyl, hydroxy, halogen, oxo, (subst)aminoalkyl, and carboxyalkyl or two substituents may be linked to form the residue of a heterocyclic or carbocyclic ring.

Examples of the group 'Het' include unsubstituted and substituted imidazolyl, triazolyl, tetrazolyl, thiazolyl, thiadiazolyl, thiatriazolyl, oxazolyl, triazinyl and oxadiazolyl.

Suitable groups 'Het' include unsubstituted and substituted 1,2,3-triazolyl; 1,2,4-triazolyl; tetrazolyl; oxazolyl; thiazolyl; 1,3,4-oxadiazolyl; 1,3,4-thiadiazolyl, or 1,2,4-thiadiazolyl. Preferably the heterocyclylthio group is 1-methyl-1H-tetrazol-5-ylthio, 2-methyl-1,3,4-thia-diazol-5-ylthio, 1-carboxymethyl-1H-tetrazol-5-ylthio or 6-hydroxy-2-methyl-5-oxo-2H-1,2,4-triazin-3-ylthio.

The nitrogen containing heterocyclic group bonded via nitrogen is suitably a pyridinium group unsubstituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylmethyl, carbamoyl, trifluoromethyl, hydroxy, halogen, oxo, aminoalkyl or two substituents may be linked to form the residue of a carbocyclic ring.

From the foregoing it will be realised that preferred antibacterially active compounds of this invention can be represented by the formula (II) or a pharmaceutically acceptable salt or in vivo hydrolysable ester thereof.

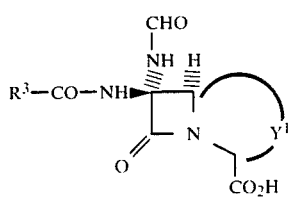

(II)

wherein $R^3$ is a group such that $R^3$—CO—NH— is an acylamino group, in particular that as found in antibacterially active penicillins or cephalosporins and $Y^1$ is:

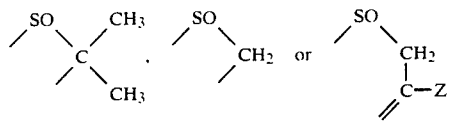

wherein Z is as defined with respect to formula (I).

Suitable groups $R^3CO$— for inclusion in the compounds of the formula (II) include those of the subformulae (a)–(e):

$$A_1-(CH_2)_p-\underset{X}{\overset{|}{CH}}-(CH_2)_m-CO- \quad (a)$$

$$A_2-CO- \quad (b)$$

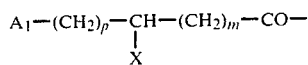  (c)

$$A_2-X_2-(CH_2)_p-CO- \quad (d)$$

$$A_3-\underset{\underset{N-OA_4}{\|}}{C}-CO- \quad (e)$$

wherein p is 0, 1 or 2; m is 0, 1 or 2; $A_1$ is $C_{1-6}$ alkyl, substituted $C_{1-6}$ alkyl, $C_{3-6}$ cycloalkyl, cyclohexenyl, cyclohexadienyl, an aromatic group, such as phenyl, substituted phenyl, thienyl, pyridyl, an optionally substituted thiazolyl group a $C_{1-6}$ alkylthio group or $C_{1-6}$ alkyloxy; X is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group such as a phenyl, a 2,6-dimethoxyphenyl, 2-alkoxy-1-naphthyl, 3-arylisoxazolyl, 3-aryl-5-methylisoxazolyl group, a substituted alkyl group, or a substituted dithietane; $X_1$ is a $CH_2OCH_2$, $CH_2SCH_2$ or $(CH_2)_p$ group; $X_2$ is an oxygen or sulphur atom; $A_3$ is an aryl or heteroaryl group such as phenyl, substituted phenyl or aminothiazolyl; and $A_4$ is hydrogen, $C_{1-6}$ alkyl, $C_{3-6}$ cycloalkyl, arylamino- carbonyl, $C_{1-6}$ alkylaminocarbonyl, $C_{1-6}$ alkanoyl, $C_{1-6}$ alkoxycarbonyl, $C_{2-6}$ alkenyl, carboxy $C_{1-6}$ alkyl, $C_{1-6}$ alkylsulphonyl and di-$C_{1-6}$ alkylphosphatomethyl.

More suitably $A_1$ is $C_{1-6}$ alkyl, $C_{3-6}$ cycloalkyl, cyclohexenyl, cyclohexadienyl, phenyl, hydroxy-phenyl, thienyl or pyridyl group; and X is a hydrogen or halogen atom, a carboxylic acid, carboxylic ester, azido, tetrazolyl, hydroxy, acyloxy, amino, ureido, guanidino or acylureido group.

Other more suitable groups $A_1$ include dihydroxyphenyl and diacetoxyphenyl.

Favoured groups $R^3$ for inclusion in the compounds of the formula (II) include those of the sub-formula (f) and (g):

 (f)

 (g)

wherein $R^4$ is a phenyl, thienyl or phenoxy group; $R^5$ is a hydrogen atom or methyl group; $R^6$ is a phenyl, substituted phenyl, substituted thiazolyl, thienyl or cyclohexadienyl group; and $R^7$ is a hydroxyl, carboxylic acid group or lower alkyl or phenyl, tolyl or indanyl ester thereof, amino or a substituted amino group.

Suitably the substituted phenyl group for $R^6$ is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, halo($C_{1-6}$)alkyl, oxo($C_{1-6}$)alkyl, $C_{1-6}$ alkylcarbonyl, aryloxy, aralkyloxy, arylcarbonyl, $C_{1-6}$ alkylamino or di($C_{1-6}$)alkylamino.

Preferably $R^6$ is a phenyl, p-hydroxyphenyl, thienyl or cyclohexadienyl group.

Other preferred groups $R^6$ include 3,4-dihydroxyphenyl and 3,4-diacetoxyphenyl.

Preferably $R^7$ is a substituted amino group.

More preferably the substituted amino group $R^7$ is a ureido, acylamino or acylureido group.

One suitable sub-group within the present invention provides a compound of formula (III) or a pharmaceutically acceptable salt or in vivo hydrolysable ester thereof:

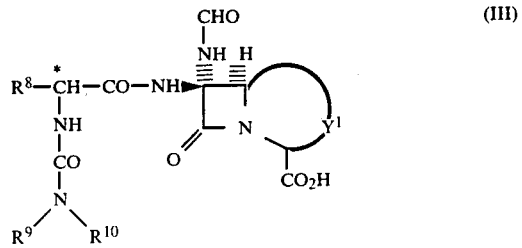

(III)

wherein $Y^1$ is as defined with respect to formula (II) and $R^8$ is phenyl, substituted phenyl, cyclohexenyl, cyclohexadienyl, or a 5- or 6-membered heterocyclic ring containing up to three hetero-atoms selected from oxygen, sulphur or nitrogen, optionally substituted with hydroxy, amino, halogen, substituted amino or $C_{1-6}$ alkoxy; $R^9$ is hydrogen or an optionally substituted $C_{1-6}$ alkyl group and $R^{10}$ is an optionally substituted 5- or 6-membered heterocyclic group containing one or two nitrogen heteroatoms; or $R^9$ and $R^{10}$ together with the nitrogen atom to which they are attached form an optionally substituted five- or six-membered heterocyclic group containing one or two nitrogen heteroatoms.

Suitably the substituted phenyl group for $R^8$ is a phenyl group substituted with up to three groups selected from $C_{1-6}$alkyl, phenyl, halogen, $C_{1-6}$ alkoxy, amino, nitro, hydroxy, $C_{1-6}$ alkylamino, $C_{1-6}$ alkylcarbonyloxy, carboxy, $C_{1-6}$ alkoxycarbonyl, halo($C_{1-6}$)alkyl, oxo($C_{1-6}$)alkyl, $C_{1-6}$ alkylcarbonyl, aryloxy, aralkyloxy, arylcarbonyl, $C_{1-6}$ alkylamino or di($C_{1-6}$)alkylamino.

In formula (III), the group $R^8$ is preferably phenyl, 4-hydroxyphenyl, 3,4-di($C_{1-6}$alkylcarbonyloxy)phenyl, 3,4-dihydroxyphenyl, 2-thienyl, 3-thienyl or 2-amino-4-thiazolyl.

Particularly preferred groups $R^8$ are 3,4-dihydroxyphenyl and 3,4-diacetoxyphenyl.

Suitably $R^9$ is hydrogen.

Suitable substituents for the 5- or 6-membered heterocyclic group of $R^{10}$ or $R^9$ and $R^{10}$ together include the optionally substituted alkyl, alkenyl, alkynyl, cycloalkyl or cycloalkenyl group; optionally substituted phenyl, oxo; the hydroxy group optionally substituted by alkyl, alkenyl, cycloalkyl, phenyl, pyridyl, pyrimidyl or benzyl; the optionally substituted mercapto group, the alkylsulphonyl group; the substituted imino group; or the amino group optionally substituted by an alkyl, alkenyl, cycloalkyl, phenyl, substituted phenyl or benzyl group. Alternatively two substituents on the ring may form the residue of a further carbocyclic or heterocyclic ring.

Preferred values for $Y^1$ in the compounds of formula (III) are —SO—C(CH$_3$)$_2$— and —SO—CH$_2$—C(CH$_2$Q)=, wherein Q is as hereinbefore defined ie when the compounds of formula (III) are derivatives of a penicillin or cephalosporin.

The carbon atom marked * in formulae herein is asymmetric so that the compounds may exist as two optionally active diastereisomers. In general that prepared from the D-side chain exhibits the highest antibacterial activity and accordingly the D compound of the DL mixtures are preferred, with the D compound being particularly preferred.

One particularly preferred sub-group within the present invention provides a compound of formula (IV) or a pharmaceutically acceptable salt or in vivo hydrolysable ester thereof:

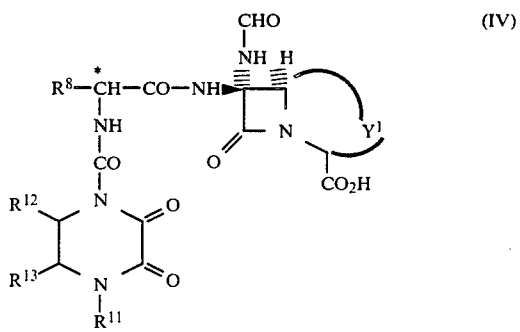

wherein $R^8$ and $Y^1$ are as defined with respect to formula (III) and $R^{11}$ represents hydrogen, $C_{1-6}$ alkyl, substituted alkyl, aryl, or aralkyl; $R^{12}$ and $R^{13}$ are the same or different and represent hydrogen, $C_{1-6}$ alkyl, substituted alkyl, halogen, amino, hydroxy or $C_{1-6}$ alkoxy or $R^{12}$ and $R^{13}$ form the residue of 5- or 6-membered carbocyclic or heterocyclic ring.

Suitable values for $Y^1$ in the compounds of formula (IV) are —SO—C(CH$_3$)$_2$— and —SO—CH$_2$—C(CH$_2$Q)= wherein Q is as hereinbefore defined.

Suitable $C_{1-6}$ alkyl groups for the groups $R^{11}$, $R^{12}$ and $R^{13}$ in formula (IV) include methyl, ethyl, n- and isopropyl, n, sec-, iso- and tert-butyl. Preferably $R^{11}$ is ethyl. Preferably $R^{12}$ and $R^{13}$ are hydrogen.

Specific compounds within this invention include the following and pharmaceutically acceptable salts and in vivo hydrolysable esters thereof:

7β-[D-2-[(4-Ethyl-2,3-dioxopiperazin-1-yl)carbonylamino]-2-(3,4-diacetoxyphenyl)acetamido]-7α-formamidocephalosporanic acid-1-oxide;

7β-[D-2-[(4-Ethyl-2,3-dioxopiperazin-1-yl)carbonylamino]-2-phenylacetamido]-7α-formamidocephalosporanic acid-1-oxide;

6β-[D-2-[(4-Ethyl-2,3-dioxopiperazin-1-yl)carbonylamino]-2-(3,4-diacetoxyphenyl)acetamido]-6β-formamidopenicillanic acid-1-oxide;

7β-[D-2-(3,4-Diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-(3,4-Dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-cephem-3-em-4-carboxylic acid-1-oxide;

7β-[D-2-[(4-Ethyl-2,3-dioxopiperazin-1-yl)carbonylamino]-2-phenylacetamido]-7α-formamido-3-pyridiniummethyl-ceph-3-em-4-carboxylate-1-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1α-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1β-oxide;

6α-Formamido-6β-(phenylacetamido)penicillanic acid-1β-oxide;

7β-[D-2-[(4-Ethyl-2,3-dioxopiperazin-1-yl)carbonylamino]-2-(4-hydroxyphenyl)acetamido]-7α-formamidocephalosporanic acid 1-oxide;

3-[(1-Carboxymethyl-1H-tetrazol-5-yl)thiomethyl]-7β-[D-2-(3,4-diacetoxyphenyl)-2-[(4-ethyl-2,3-dioxopiperazin-1-yl)carbonylamino]acetamido]-7α-formamidoceph-3-em-4-carboxylic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1α-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1β-oxide;

6β-(Phenoxyacetamido)-6α-formamidopenicillanic acid-1-oxide;

6β-[D-2-[(4-Ethyl-2,3-dioxopiperazin-1-yl)carbonylamino]-2-phenylacetamido]-6α-formamidopenicillanic acid-1-oxide;

6β-(D-2-Amino-2-phenylacetamido)-6α-formamidopenicillanic acid-1-oxide;

6β-[D-2-(4-Hydroxyphenyl)-2-[[3-(methylsulphonyl)-2-oxoimidazolidin-1-yl)carbonylamino]acetamido]-6α-formamidopenicillanic acid-1-oxide;

7α-Formamido-7β-(thien-2-ylacetamido)cephalosporanic acid-1β-oxide;

7α-Formamido-7β-(thien-2-ylacetamido)cephalosporanic acid-1α-oxide;

3-Carbamoyloxymethyl-7α-formamido-7β-(thien-2-ylacetamido)ceph-3-em-4-carboxylic acid-1-oxide; and 6α-Formamidopenicillanic acid-1-oxide.

Further specific compounds within this invention include the following and pharmaceutically acceptable salts and in vivo hydrolysable esters thereof;

7β-[D,2-[(4-Ethyl-2,3-dioxopiperazin-1-yl)carbonylamino]-2-phenylacetamido]-7α-formamidocephalosporanic acid-1,1-dioxide and
6β-[D-2-[(4-Ethyl-2,3-dioxopiperazin-1-yl)carbonylamino]-2-(3,4-diacetoxyphenyl)acetamido]-6α-formamidopenicillanic acid-1,1-dioxide.

The antibiotic and β-lactamase inhibitory compounds according to the invention may be formulated for administration in any convenient way for use in human or veterinary medicine, according to techniques and procedures per se known in the art with reference to other antibiotics and β-lactamase inhibitors, and the invention therefore includes within its scope a pharmaceutical composition comprising an antibiotic or β-lactamase inhibitory compound according to the present invention such as, for example a compound of formula (II) above together with a pharmaceutical carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose preparation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol, or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may contain edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, eg cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100–10000 mg per day, for instance 1500 mg per day depending on the route and frequency of administration.

The antibiotic compound according to the present invention may be the sole therapeutic agent in the compositions of the invention or is present in combination with other antibiotics and/or β-lactamase inhibitory agents.

Advantageously the compositions also comprise a compound of formula (V) or a pharmaceutically acceptable salt or ester thereof;

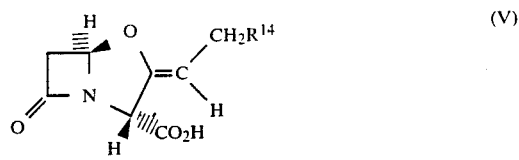

wherein $R^{14}$ is hydroxyl, substituted hydroxyl, thiol, substituted thiol, amino, mono- or di-hydrocarbyl substituted amino, or mono- or di-acylamino.

A further advantageous composition comprises an antibacterially effective amount of an antibiotic compound according to the invention together with a β-lactamase inhibitory amount of a β-lactamase inhibitor or formula (VI) or a pharmaceutically acceptable salt or in vivo hydrolysable ester thereof:

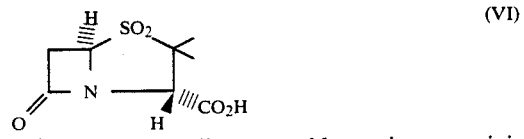

ps and a pharmaceutically acceptable carrier or excipient.

Further suitable β-lactamase inhibitors include 6β-bromopenicillanic acid and salts and in vivo hydrolysable esters and 6β-iodopenicillanic acid and salts and in vivo hydrolysable esters thereof.

Such compositions of this invention which include a β-lactamase inhibitory amounts of a β-lactamase inhibitor are formulated in a conventional manner using techniques and procedures per se known in the art.

The present invention also includes a method of treating bacterial infections in humans and animals which comprises the administration of a therapeutically effective amount of an antibiotic compound of this invention.

The antibiotic compounds of the present invention are active against a broad range of gram positive and gram negative bacteria, in particular they are useful for treatment of respiratory tract and urinary tract infection in humans and mastitis in cattle. A particular advantage of the antibacterially active compounds of this invention is their stability to β-lactamase enzymes and they are therefore effective against β-lactamase producing organisms.

In another aspect the present invention provides a process for the preparation of a compound having partial structure (A) which process comprises formylating a compound having the partial structure (VII):

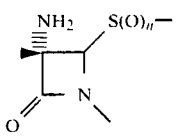 (VII)

wherein n is as hereinbefore defined.

The present invention further provides a process for the preparation of a compound of formula (I) which process comprising formylating a compound of formula (VIII).

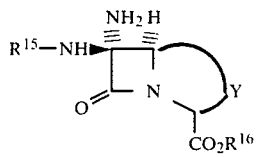 (VIII)

where any reactive groups may be protected; $R^{15}$ is an amino-protecting group or an acyl group as found in antibacterially active penicillins and cephalosporins and wherein any reactive groups may be protected; and $R^{16}$ is a readily removable carboxy protecting group; and thereafter, if necessary, carrying out one or more of the following steps:

i. converting a group $R^{15}$ to a group $R^1$;
ii. converting a group $R^{16}$ to a group $R^2$;
iii. converting one group Z into a different group Z;
iv. converting the product into a salt.

Suitable formylating agents include mixed anhydrides such as formic acetic anhydride. The reaction may suitably be carried out in a temperature in the range −50° C. to 30° C. in aprotic solvent such as for example, dichloromethane, chloroform, dimethylformamide, tetrahydrofuran, hexamethylphosphoramide, or dimethylsulphoxide, in the presence of a tertiary base. A preferred tertiary basse employed in the reaction is a base of the pyridine type, such as pyridine, lutidine or picoline.

Processes for the preparation of compounds of formula (VIII) are analogous to those disclosed in U.S. Pat. No. 3,962,214, and UK Pat. No. 1348984 and UK Patent Application GB No. 2107307A.

In a further aspect the present invention provides a process for the preparation of a compound having partial structure (A) which process comprises oxidation of a compound of formula (IX):

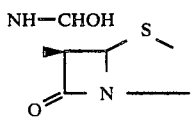 (IX)

Processes for the preparation of compounds within formula (IX) are disclosed in UK Patent Application GB No. 2107307A.

Compounds of the formula (I) may be prepared by the oxidation of a corresponding compound of formula (X):

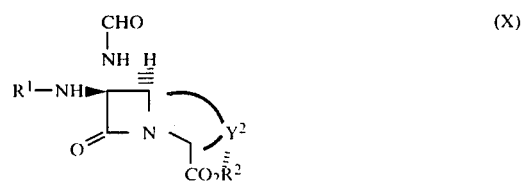 (X)

wherein $R^1$ and $R^2$ are as hereinbefore defined; and $Y^2$ is:

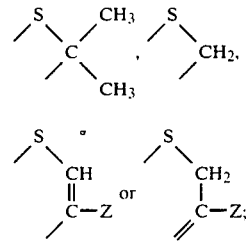

wherein Z is as hereinbefore defined.

Such oxidation may conveniently be performed in conventional manner, for example using a per-acid such as peracetic acid or m-chloroperbenzoic acid, suitably at an ambient or depressed temperature. Suitable solvents for such a sulphoxidation include ethylacetate, chloroform, dichloromethane, dioxan and tetrahydrofuran.

Processes for the preparation of compounds of the formula (X) are disclosed or are analogous to those disclosed in our copending European Patent Application No. 823038212.1, UK Patent Application No. 8221059 (UK Patent Application GB No. 2107307A) and U.S. Patent Application No. 401,266 of 23rd July 1982.

Compounds of the formula (I) wherein n is 1 are also useful intermediates in the preparation of compounds of formula (X); for example compounds of formula (I) wherein Y is —SO—CH$_2$—CZ= may be converted to the corresponding compound of formula (X) wherein $Y^2$ is —S—CH$_2$—CZ= by reduction. Suitable reducing agents include those known in the art for reducing Δ3 and Δ2 cephalosporin sulphoxides. In particular these compounds of formula (X) wherein $Y^2$ is —S—CH= CZ— may be converted to a corresponding compound of formula (X) wherein $Y^2$ is —S—CH$_2$—CZ= by oxidation, isomerisation and subsequent reduction.

Certain compounds within formula (X) are novel and form a further aspect of the present invention.

Novel compounds within formula (X) include those wherein $Y^2$ represents:

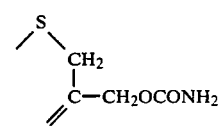

Further novel compounds within formula (X) include:

7β-[D-2-[(4-Ethyl-2,3-dioxopiperazin-1-yl)car-
bonylamino]-2-phenylacetamido]-7α-formamido-3-
[(1-methyl-1H-tetrazol-5-yl)thiomethyl]ceph-3-em-4-
carboxylic acid, sodium salt;

7β-[D-2-(4-Ethyl-2,3-dioxopiperazin-1-ylcarbox-
amido)-2-phenylacetamido]-7α-formamido-3-
pyridiniummethylceph-3-em-4-carboxylate; and 7β-[D-2-[(4-Ethyl-2,3-dioxopiperazin-1-yl)car-
bonylamino]-2-(3,4-dihydroxyphenyl)acetamido]-7α-
formamido-3-[(1-methyl-1H-tetrazol-5-yl)thiome-
thyl]ceph-3-em-4-carboxylic acid, sodium salt.

The antibacterially active compounds of formula (II) as hereinbefore defined may suitably be prepared by reacting a compound of formula (XI):

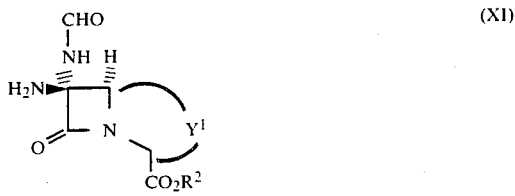

wherein the amino group is optionally substituted with a group which permits acylation to take place and $R^2$ is as hereinbefore defined with reference to formula (I) above, with an N-acylating derivative of an acid of formula (XII):

$$R^3CO_2H \qquad (XII)$$

wherein $R^3$ is as defined with respect to formula (II) and wherein any reactive groups therein may be protected; and thereafter, if necessary, carrying out one or more of the following steps:

i. removing any carboxyl-protecting group $R^2$;
ii. removing any protecting groups on the side-chain group;
iii. further derivatising the side chain group;
iv. converting one group Z to a different group Z;
v. converting the product into a salt or in vivo hydrolysable ester thereof.

Suitable groups which permit acylation to take place and which are optionally present on the amino group of the starting material of the formula (XII) include N-silyl, N-stannyl and N-phosphorus groups, for example trialkylsilyl groups such as trimethylsilyl, trialkyltin groups such as tri-n-butyltin, groups of formula —P.-$R^aR^b$ wherein $R^a$ is an alkyl, haloalkyl, aryl, aralkyl, alkoxy, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P-(OC$_2$H$_5$)$_2$, —P(C$_2$H$_5$)$_2$,

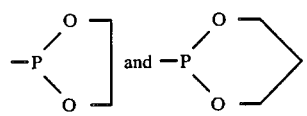

The carboxy group may be regenerated from any of the above esters by usual methods appropriate to the particular $R^2$ group, for example, acid—and base—catalysed hydrolysis, or by enzymically—catalysed hydrolysis, or by hydrogenolysis.

Suitable carboxyl-protecting derivatives for the group —CO$_2$R$^2$ in formula (XI) include salts and ester derivatives of the carboxylic acid as described hereinbefore with reference to formula (I).

A reactive N-acylating derivative of the acid (XII) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example, tertiary amine (such as triethylamine, pyridine or dimethylaniline), an inorganic base (such as calcium carbonate or sodium bicarbonate) or an oxirane, which binds hydrogen halide liberated in the acylation reaction. The oxirane is preferably a (C$_{1-6}$)—1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (XII) or a salt thereof with a halogenating (eg chlorinating or brominating) agent such as phosphorus pentachloride, thionyl chloride or oxalyl chloride.

Alternatively, the N-acylating derivative of the acid (XII) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as p-toluenesulphonic acid). When a symmetrical anhydride is employed, the reaction may be carried out in the presence of 2,6-lutidine as catalyst.

Alternative N-acylating derivatives of acid (XII) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, or 8-hydroxyquinoline; or amides such as N-acylsaccharins, N-acylthiazolidin-2-thione or N-acylphthalimides; or an alkylidene iminoester prepared by reaction of the acid (XII) with an oxime.

Other reactive N-acylating derivatives of the acid (XII) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

Aptly the acid of formula (XII) is an acid of formula (XIII):

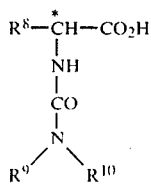  (XIII)

wherein $R^8$, $R^9$ and $R^{10}$ are as hereinbefore defined; thereby affording a compound of formula (III) as hereinbefore defined.

The compounds of formula (III) may also suitably be prepared by reacting a compound of formula (XIV):

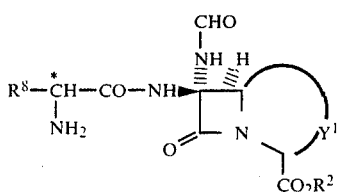  (XIV)

wherein $R^2$, $R^8$ and $Y^1$ are as hereinbefore defined and the α-amino group is optionally substituted with a group which permits acylation to take place, and any reactive groups may be protected, with an N-acylating derivative of an acid of formula (XV):

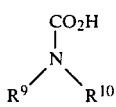  (XV)

wherein $R^9$ and $R^{10}$ are as hereinbefore defined and wherein any reactive groups may be protected; and thereafter, if necessary, carrying out one or more of the following steps:
  i. removing any carboxyl-protecting group $R^2$;
  ii. removing any protecting groups on the side-chain group;
  iii. converting one group Z to a different group Z;
  iv. converting the product into a salt or in vivo hydrolysable ester thereof.

The compounds of formula (XIV) herein which are inter alia intermediates for the compounds of formula (III) as hereinbefore defined may be prepared by reacting a compound of formula (XI) with an N-acylating derivative of an acid of formula (XVI):

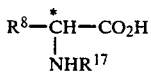  (XVI)

wherein $R^{17}$ is an amino-protecting group and thereafter removing protecting group $R^{17}$.

Suitable amino protecting groups $R^{17}$ include those disclosed hereinbefore with reference to group $R^1$, with alkoxycarbonyl groups such as, for example, 4-nitrobenzyloxycarbonyl and trichloroethyloxycarbonyl being particularly preferred.

The sub-group of compounds within the present invention of formula (XVII):

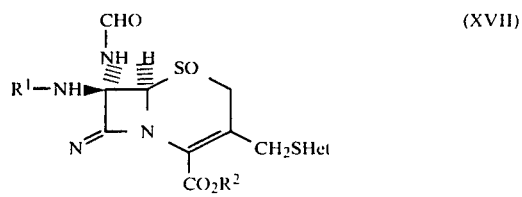  (XVII)

wherein $R^1$, $R^2$ and 'Het' are as defined hereinbefore with reference to formula (I) may suitably be prepared by reacting a compound of formula (XVIII):

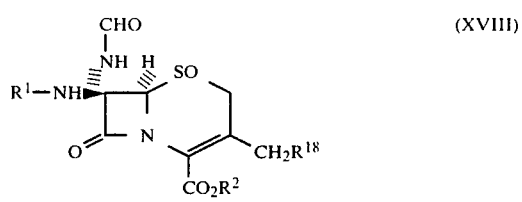  (XVIII)

wherein $R^1$ and $R^2$ are as defined hereinbefore and wherein any reactive groups may be protected and $R^{18}$ is a leaving group; with a thiol of formula:

HetSH with the proviso that when $R^{18}$ is an acyloxy group $-CO_2R^2$ must be in the free acid form or a salt thereof.

Suitable leaving groups $R^{18}$ include halogen such as iodide or bromide or an acyloxy group such as, for example the acetyloxy group.

The thiol HetSH may be reacted as the free compound or a slat with an alkali metal such as sodium or potassium. This reaction is desirably conducted in a solvent. For example, use can be made of water, or organic solvents inert to the starting compounds, such as dimethylformamide, dimethylacetamide, dioxane, acetone, alcohol, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carried out at a selected temperature within the range of 0° to 100° C. for a selected time of a few hours to several days. The reaction is desirably conducted between pH 3 and 7.

To prevent oxidation of the thio compounds it is advantageous to carry out the reaction in an inert gaseous atmosphere, eg nitrogen gas.

The subgroup of compounds within the present invention of formula (XIX):

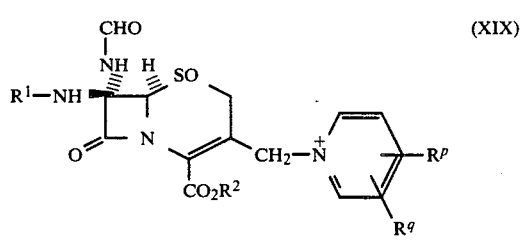  (XIX)

wherein $R^1$, $R^2$, $R^p$, $R^q$ are as defined hereinbefore may suitably be prepared by reacting a compound of formula (XVIII) as hereinbefore defined with the appropriately substituted pyridine.

Suitably the reaction with the pyridine is carried out in a polar solvent such as water, and in the presence of a catalyst such as an alkali metal thiocyanate or an alkali metal halide such as, for example sodium iodide.

The antibiotic compounds of the present invention are active against a wide range of gram negative and gram positive organisms including *E. coli* such as, for example ESS, JT4, JT425 and NCTC 10418; *Pseudomonas Spp.* such *Ps.aeruginosa* for example 10662 and Dalgleish; *Serratia marcescens* US32; *Klebsiella aerogenes* A; *Enterobacter cloacae* N1; *P.mirabilis* such as, for example C977 and 889; *P.morganii, P.rettgeri; B.subtilis; Staph aureus* such as, for example Oxford and Russell; *N.catarrhalis* 1502; *Strep faecalis* I; β-*Haemolytic Strep* CN10. The MIC data included in the following examples is representative of the activity of the compounds of the present invention.

The following Examples illustrate the preparation and use of the compounds of the present invention.

EXAMPLE 1

Sodium
7β-[D-2-[(4-ethyl-2,3-dioxopiperazin-1-yl)carbonylamino]-2-(3,4-diacetoxyphenyl)acetamido]-7α-formamidocephalosporanate-1-oxide (a) t-Butyl 7β-[D-2-[(4-ethyl-2,3-dioxopiperazin-1-yl)carbonylamino]-2-(3,4-diacetoxyphenyl)acetamido]-7αformamidocephalosporanate-1-oxide t-Butyl 7β-[D-2-[(4-ethyl-2,3-dioxopiperazin-1-yl)carbonylamino]-2-(3,4-diacetoxyphenyl)acetamido]-7α-formamidocephalosporanate (229 mg; see U.K. Patent Application GB No. 2,107,307A) in dichloromethane (10 ml) was cooled to −20° C. and peracetic acid (0.35 ml; 5.2% w/v solution in acetic acid) added. After 30 min. more peracetic acid (0.2 ml) was added and after a further 10 min the solution was evaporated in vacuo. Toluene was added and the solvent evaporated off. This was repeated once more to give a white solid. Chromatography (silica gel; gradient elution 2%–10% methanol in ethyl acetate) afforded the two sulphoxide isomers of the title compound.

Isomer A (76 mg); $\nu_{max}$ (CHCl$_3$) 3260, 1795, 1775, 1718, 1690, 1045, 1010 cm$^{-1}$. δ(CDCl$_3$) inter alia 1.19 (t, 3H, J 8 Hz), 1.55(s, 9H, CO$_2$C(CH$_3$)$_3$), 2.07(3H, s, CH$_2$OAc), 2.27(6H, s, ArOAc), 3.19 (1H, d, part of ABq J17 Hz) 3.53(4H, m), 4.05(2H, m), 4.66 and 5.13 (2H, ABq, J14 Hz, —CH$_2$—O), 4.84(1H, s, 6-H), 5.77(1H, d, J7 Hz), 7.15–7.45(3H, m, aromatics), 7.92b(1H, s, exch. D20), 8.11(1H, s, CHO), 8.81b(1H, s, exch.D20), 9.98(1H, d, J7 Hz, exch. D20).

Isomer B (93 mg); $\nu_{max}$ (CHCl$_3$) 3300, 1795, 1770, 1718, 1685, 1045 cm$^{-1}$. δ(CDCl$_3$) inter alia 1.21 (t, 3H, J7 Hz), 1.54(s, 9H, CO$_2$C(CH$_3$)$_3$), 2.08(3H, s, CH$_2$OAC), 2.27 (3H, s, ArOAc), 2.30(3H, s, ArOAc) 3.42 and 3.6(2H, ABq, J15.5 Hz) 3.4–3.7(4H, m), 3.8–4.0(1H, m), 4.0–4.2(1H, m), 4.72(1H, s, 6-H), 4.79 and 5.13(2H, ABq, J14 Hz), 5.6(1H, d, J7 Hz), 7.15(1H, s, exch. D20), 7.1–7.4(3H, m, aromatics), 8.0b (1H, s, exch.D20), 8.6b (1H, s, exch. D20), 10.06(1H, d, J7 Hz, exch D20).

(b) Sodium 7β-[D-2-[(4-ethyl-2,3-dioxopiperazin-1-yl)carbonylamino]-2-(3,4-diacetoxyphenyl)acetamido]-7α-formamidocephalosporanate-1-oxide Isomer A t-butyl 7β-[D-2-[(4-ethyl-2,3-dioxopiperazin-1-yl)carbonylamino]-2-(3,4-diacetoxyphenyl)acetamido]-7α-formamidocephalosporanate-1-oxide (71 mg; isomer A) was dissolved in trifluoroacetic acid (5 ml). After 30 min. the solvent was evaporated, toluene added and the process repeated. The residue was dried in vacuo and the resulting solid suspended in water (2 ml). The pH was adjusted to 6.5 by the addition of dilute sodium hydrogen carbonate solution. The solution was chromatographed on HP20SS using acetone-water mixtures. The combined product containing fractions (hplc control) were partially evaporated and then freeze-dried to give the title compound (54 mg) $\nu_{max}$(KBr), 3424, 1776, 1712, 1678, 1614, 1045, 1019 cm$^{-1}$. δ(D$_2$O) inter alia 1.2(3H, t, J9 Hz), 2.08(3H, s, CH20Ac), 2.36(6H, s, ArOAc), 3.42–3.8(6H, m), 3.92–4.15(2H, m), 4.61(2H, d, part of Abq, J.16 Hz), 5.08(1H, s, 6-H), 5.57(1H, s, NCHCO), 7.3–7.6(3H, m, aromatics), 8.15(1H, s, CHO).

MIC against *P. mirabilis* 889 is 0.5 μg/ml.

Isomer B t-Butyl 7β-[D-2-[4-ethyl-2,3-dioxopiperazin-1-yl)-carbonylamino]-2-(3,4-diacetoxyphenyl)acetamido]-7α-formamidocephalosporanate-1-oxide (89 mg; isomer B) was treated with trifluoroacetic acid and the product (68 mg) isolated as a freeze-dried solid as described for isomer A. $\nu_{max}$ (KBr) 3441, 1777, 1712, 1680, 1615, 1043, 1020 cm$^{-1}$. δ(D$_2$O) inter alia 1.18(3H, t, J8 Hz), 2.1(3H, s, CH$_2$OAc), 2.34(6H, s, ArOAc), 3.42–3.6(3H, m), 3.62–3.79(2H, m), 3.91–4.12(3H, m), 4.63(1H, d, part of ABq, J15 Hz), 5.07 (1H, s, 6-H), 5.58(1H, s, NCHCO), 7.3–7.58(3H, m, aromatics), 8.21(1H, s, CHO)).

MIC against *P. mirabilis* 889 is <0.06 μg/ml.

EXAMPLE 2

Sodium
7β-[D,2-([4-Ethyl-2,3-dioxopiperazin-1-yl]carbonylamino)-2-phenylacetamido]-7α-formamidocephalosporanate-1,1-dioxide 7β-[D,2-([4-Ethyl-2,3-dioxopiperazin-1-yl]carbonylamino)-2-phenylacetamido]-7α-formamidocephalosporanic acid (100 mg; 0.16 mmol) was dissolved in methanol (8 ml), cooled to 0° and m-chloroperbenzoic acid (60 mg; 0.32 mmol) added. After stirring at 0° for 30 min and at room temperature for 7 h., further m-chloroperbenzoic acid (60 mg; 0.32 mmol) was added, and stirring continued a further 16 h. The solution was evaporated and the residue dissolved in water by adjusting the pH to 6.5 with dilute aqueous sodium hydrogencarbonate solution. Chromatography on Diaion HP 20 SS and lyophilisation of the product containing fractions gave the title compound (49 mg; 45%). $\nu_{max}$ (H$_2$O) 253 nm, $\epsilon_m$ (13.058); $\nu_{max}$ (KBr) 1800, 1710, 1680, 1620, 1330, 1125 cm$^{-1}$; δppm (D$_2$O) 1.20 (3H, t, J 7 Hz), 2.08 (3H, s), 3.51 (2H, q, J 7 Hz), 3.69 (2H, m), 3.84 and 4.23 (2H, ABq, J 18 Hz) 4.01 (2H, m), 4.66 and 4.86 (2H, ABq, J 14 Hz), 5.49 (1H, s, ), 5.53 (1H, s), 7.46 (5H, m), 8.18 and 8.46 (together 1H, s).

MIC against *P. mirabilis* 889 is 8 μg/ml.

EXAMPLE 3

Sodium
7β-[D-2-[(4-Ethyl-2,3-dioxopiperazin-1-yl)carbonylamino]-2-phenylacetamido]-7α-formamidocephalosporanate-1-oxide (a) t-Butyl 7β-[D-2-[(4-Ethyl-2,3-dioxopiperazin-1-yl)carbonylamino]-2-phenylacetamido]-7α-formamidocephalosporanate-1-oxide t-Butyl 7β-[D-2-[(4-Ethyl-2,3-dioxopiperazin-1-yl)carbonylamino]-2-phenylacetamido]-7α-formamidocephalosporanate (200 mg; 0.297 mmol) was dissolved in anhydrous dichloromethane (5 ml), cooled to −20° and peracetic acid (42 μl of a 52% w/v solution in acetic acid; 0.297 mmol) added. The reaction mixture was allowed to reach room temperature over 2 h., and evaporated to dryness. Toluene was added to the residue and the suspension evaporated; this was repeated. The residue was chromatographed on silica gel to give the two isomers of the title compound.

Isomer A. (59 mg; 29%) γmax (EtOH) 263 nm, $\epsilon_m$ (10,871); $\nu_{max}$(CHCl$_3$) 3275, 1800, 1715, 1690, 1620 (sh), 1040 cm$^{-1}$; δppm ([CD$_3$]$_2$CO) 1.17 (3H, t, J 7 Hz), 1.57 (9H, s), 2.02 (3H, s), 3.51 (2H, q, J 7 Hz), 3.71 (2H, m), 3.47 and 3.64 (two lines of ABq, 2H obscured by multiplets at 3.51δ and 3.71δ), 4.06 (2H, m), 4.58 and 5.13, 4.66 and 5.25 (together 2H, ABq, J 14 Hz), 4.93 and 5.02 (together 1H, s), 5.69 (1H, s), 7.35 (3H, m), 7.55 (2H, m), 8.19 and 8.55 (together 1H, s).

Isomer B. (38 mg; 19%) $\nu_{max}$ (CHCl$_3$) 3280, 1800, 1715, 1690, 1620 (sh), 1045 cm$^-$; δppm ([CD$_3$]$_2$CO) 1.17 (3H, t, J 7 Hz), C-3 CH$_3$CO obscured by solvent peak, 1.51 (9H, s), 3.50 (2H, q, J 7 Hz), 3.54 and 3.80 (2H, ABq, J 16 Hz), 3.72 (2H, m), 4.05 (2H, m), 4.70 (1H, s), 4.80 and 5.21 (2H, ABq, J 14 Hz), 5.69 (1H, s), 7.39 (3H, m), 7.52 (2H, m), 8.28 and 8.36 (together 1H, s).

(b) Sodium 7β-[D-2-[(4-Ethyl-2,3-dioxopiperazin-1-yl)carbonylamino]-2-phenylacetamido]-7α-formamidocephalosporanate-1-oxide Isomer A t-Butyl 7β-[D-2-[(4-Ethyl-2,3-dioxopiperazin-1-yl)carbonylamino]-2-phenylacetamido]7α-formamidocephalosporanate-1-oxide (Isomer A) (59 mg; 0.086 mmol) was dissolved in trifluoroacetic acid (0.5 ml) at room temperature. After 30 min., the solution was evaporated and the residue redissolved in toluene and evaporated; this process was repeated. The residue was dissolved in dilute aqueous sodium hydrogencarbonate to pH 6.5 and chromatographed on HP 20 SS. Lyophilisation of the relevant fractions gave the title compound (40 mg; 71%). $\nu_{max}$ (KBr) 3434, 1788, 1712, 1679, 1617, 1043 cm$^{-1}$ δppm (D$_2$O) 1.19 (3H, t, J 7 Hz), 2.07(3H, s), 3.48 and 3.63 (2H, ABq, J 19 Hz), 3.51(2H, q, J 7 Hz), 3.70(2H, m), 4.0 (2H, m), 5.45 (1H, higher field arm of ABq, J 12 Hz; lower field arm obscured by HOD), 5.08 (1H, s), 5.52(1H, s), 7.3–7.5(5H, m), 8.15 and 8.49 (together 1H, s).

MIC against *P mirabilis* 889 is 0.25 μg.ml$^{-1}$

Isomer B t Butyl 7β-[D-2-([4-Ethyl-2,3-dioxopiperazin-1-yl]carbonylamino)-2-phenylacetamido]-7α-formamidocephalosporanate-1-oxide (Isomer B) (35 mg; 0.051 mmol) was dissolved in trifluoroacetic acid (0.5 ml) as described above for Isomer A. Workup and chromatography gave the title compound (26 mg; 79%). $\nu_{max}$ (KBr) 3433, 1786, 1680, 1614, 1044 cm$^{-1}$; δppm (D$_2$O) 1.19 (3h, t, J 7 Hz), 2.09 (3H, s), 3.55 and 4.09 (2H, ABq, J 18 Hz), 3.51(2H, q, J 7 Hz), 3.71 (2H, m), 4.05(2H, m), 4.62 and 4.87(2H, ABq, J 13 Hz), 5.08(1H, s), 5.56 (1H, s), 7.2–7.4 (5H, m), 8.21 (1H, s).

MIC against *P. Mirabilis* 889 is 0.25 μg ml$^{-1}$.

(c) Sodium 7β-[D-2-(4-Ethyl-2,3-dioxopiperazin-1-yl)carbonylamino)-2-phenylacetamido]-7α-formamidocephalosporanate-1-oxide.

7β-[D-2-(4-Ethyl-2,3-dioxopiperazin-1-yl)carbonylamino)-2-phenylacetamido]-7α-formamido-cephalosporanic acid (100 mg; 0.16 mmol) was dissolved in methanol (8 ml), cooled to −20° and peracetic acid (27 μl, of a 52% w/v solution in acetic acid; 0.16 mmol) added. The reaction was allowed to warm to room temperature over 2 hour, and then evaporated to dryness. The residue was dissolved in toluene and the solution evaporated; this process was repeated. The residue was dissolved in water, the pH adjusted to 6.5 with dilute aqueous sodium hydrogencarbonate and chromatographed on HP 20SS to give the title compound. Isomer A (54 mg; 51%) and Isomer B (33 mg; 31%) were identical to the products described in (b).

EXAMPLE 4

Sodium 6β-[D-2-[(4-ethyl-2,3-dioxopiperazin-1-yl)carbonylamino]-2-(3,4-diacetoxyphenyl)acetamido]-6α-formamidopenicillanate-1-oxide.

(a) Benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide.

A solution of benzyl 6β-[D-2-[(4-ethyl-2,3-dioxopiperazin-1-yl)carbonylamino]-2-(3,4-diacetoxyphenyl)acetamido]-6α-formamidopenicillanate (see UK Patent Application GB No. 2107307A) (1.00 g) in dry dichloromethane (20 ml) was stirred at 0° C. and treated with m-chloroperbenzoic acid (0.25 g). After a period of 2 hour the product was concentrated under reduced pressure and chromatographed on a column of silica gel 60, eluting with ethyl acetate/ethanol 9:1 grading to 4:1. The product was obtained as a colourless solid, which was a mixture of the two diastereoisomers about the sulphur atom (0.86 g); $\nu_{max}$. (CHCl$_3$) 3290, 2980, 1790, 1775, 1750, 1715, and 1680 cm$^{-1}$; δ(CDCl$_3$+D$_2$O) 0.84 (ca2H, s, 2-CH$_3$), 1.1–1.3 (ca7H, m, 2-CH$_3$ and NCH$_2$CH$_3$), 2.26(6H, s, COCH$_3$'s), 3.4–4.1 (6H, m, CH$_2$NCH$_2$CH$_2$N), 4.45 and 4.63 (1H, 2s, 3-H), 5.05 and 5.16 (2H, ABq, J 12 H, PhCH$_2$), 5.17 and 5.25(1H, 2s, 5-H), 5.52 and 5.65 (1H, 2d, J6 Hz, NCHCO), 7.1–7.4 (8H, m, phenyls), 8.23 and 8.08 (1H, 2s, NCHO), 10.03 and 9.80 (1H, 2d, J6 Hz, NH).

(b) Sodium 6β-[D-2-[(4-ethyl-2,3-dioxopiperazin-1-yl)carbonylamino]-2-(3,4-diacetoxyphenyl)acetamido]-6α-formamidopenicillanate-1-oxide.

A solution of benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide (0.200 g) in dry tetrahydrofuran (5 ml) was treated with 10% palladium on charcoal catalyst (0.200 g) and hydrogenated at atmospheric pressure until chromatography indicated complete deprotection (2 hour). The product was filtered through celite and washed through with dioxane (5 ml). The filtrate was concentrated to about 3 ml volume and treated with 1.93M. sodium 2-ethylhexanoate in 4-methylpentan-2-one (0.13 ml). Diethyl ether (10 ml) was added and the solid isolated by centrifugation. It was washed with 1:1 acetone/diethyl ether followed by diethyl ether, and dried under vacuum. The product, which was a mixture of two sulphoxide diastereoisomers, was obtained as a white powder (0.135 g); $\nu_{max}$ (KBr) 3410, 2980, 2965, 2835, 1776, 1710, 1677, 1617 and 1502 cm$^{-1}$; δ(D$_2$O) 0.98 1.25 and 1.55 (6H, 3s, 2-CH$_3$'s), 1.19 (3H, t, J 7 Hz, NCH$_2$CH$_3$), 2.34 (6H, s, OCOCH$_3$'s), 3.5–4.1 (6H, m, CH$_2$NCH$_2$CH$_2$N), 4.26 and 4.35 (1H, 2s, 3-H), 5.19 and 5.27(1H, 2s, 5-H), 5.51 and 5.49(1H, 2s, NCHCO), 7.3–7.6(3H, m, phenyl), 8.17 and 8.11 (1H, 2s, NCHO). MIC against *Proteus mirabilis* 889 is 0.12 μg/ml.

EXAMPLE 5

Sodium 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1-oxide.

(a) Diphenylmethyl 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1-oxide.

Diphenylmethyl 7β-[D-2-(3,4-diacetoxyphenyl)-2-[(4-ethyl-2,3-dioxopiperazin-1-yl)carbonylamino]acetamido]-7α-formamido-3[(1-methyl-1H-tetrazol-5-yl)thiomethyl]-ceph-3-em-4-carboxylate (200 mg: 0.21 mmol) (see UK Patent Application; GB No. 2,107,307A) in dichloromethane (5 ml) was treated with peracetic acid (35 μl. 52% w/v solution in acetic acid: 0.23 mmol) at −20°. The reaction mixture was allowed to warm towards room temperature over 1 hour and then evaporated. The residue was tken up in toluene and evaporated to dryness; this process was repeated. The residual solid was chromatographed to give the title compound (172 mg; 85%) as a mixture of isomers.

Isomer A $\lambda_{max}$ (EtoH)270 nm; Em(8561); $\nu_{max}$(CHCl$_3$) 3250, 1798, 1770, 1710, 1690, 1620(sh), cm$^{-1}$; δppm [(CD$_3$)$_2$CO] inter alial. 18(3H, , J7 Hz), 2.24, 2.25, 2.26, 2.27 (together 6H, s), 3.52(2H, q, J7 Hz), 3.70(2H, m), 3.92 (3H, s), 4.05 (2H, m) 4.23 and 4.41 (2H, ABq, J 13 Hz), 5.03 (1H, s), 5.83(1H, s), 6.96(1H, s), 7.1–7.7 (13H, m), 8.24, 8.50 (together 1H, s).

Isomer B $\nu_{max}$. (CHCl$_3$) 3260, 1798, 1770, 1715, 1690, 1620(sh), 1040 cm$^{-1}$; δppm. [(CD$_3$)$_2$CO] inter alia 1.18(3H, t, J7 Hz), 2.29(6H, s), 3.43(1H, d, J15 Hz higher field arm of ABq), 3.50 (2H, q, J7 Hz), 3.70(2H, m), 3.93(3H, s), 4.05 (2H, m), 4.22 and 5.07 (2H, ABq, J14 Hz), 4.54(1H, s), 5.70(1H, s), 6.97(1H, s), 7.2–7.7(13H, m), 8.31(1H, s).

(b) Sodium 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1-oxide.

Isomer A

Diphenylmethyl 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]ceph-3-em-4-carboxylate-1-oxide (Isomer A; 55 mg: 0.06 mmol) was dissolved in trifluoroacetic acid (1 ml) at room temperature. After 10 min. the reaction mixture was worked up and purified as described in 3(b) to give the title compound (34 mg; 75%). $\lambda_{max}$(H$_2$O) 265 nm, Em (13388); $\nu_{max}$ (KBr) 3429, 1774, 1710, 1679, 1611, 1045 cm$^{-1}$. δppm [D$_2$O] inter alia 1.17(3H, t, J7 Hz), 2.33(6H, s), 3.50(2H, q, J7 Hz), 3.67(2H, m), 3.99(3H, s), overlaps 4.00(2H, m), 5.53 (1H, s), 7.25–7.60(3H, m), 8.12 and 8.47(1H, s).

MIC against *P.Mirabilis* 889 is 0.5 μg.ml$^{-1}$

Isomer B

Diphenylmethyl 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate (Isomer B; 36 mg: 0.038 mmol) was dissolved in trifluoroacetic acid (1 ml) at room temperature as described above for Isomer A, to give the title compound Isomer B (22 mg; 75%). $\lambda_{max}$ (H$_2$O) 262 nm; Em(12390); $\nu_{max}$ (KBr) 3438, 1776, 1710, 1678, 1612, 1040 cm$^{-1}$; δ[D$_2$O] inter alia 1.18 (3H, t, J7 Hz), 2.31(6H, s), 3.50(2H, q, J7 Hz), 3.68(2H, m), 4.01(3H, s), overlaps 4.06(2H, m), 5.57(LH, s), 7.3–7.6 (3H, m), 8.20 and 8.42(1H, s).

MIC against *P.Mirabilis* 889 is 0.06 μg.ml$^{-1}$.

EXAMPLE 6

7β-[D-2-(3,4-Dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid-1-oxide, sodium salt (a) Diphenylmethyl 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]ceph-3-em-4-carboxylate A solution of D-2-(3,4-diacetoxyphenyl)-2-[(4-ethyl-2,3-dioxopiperazin-1-yl)carbonylamino]acetic acid (0.87 g, 2 mmol) in dichloromethane (30 ml) was added slowly dropwise to a solution of diphenylmethyl 7β-amino-7α-formamido-3-[(1-methyl-1H-tetrazol-5-yl)thiomethyl]ceph-3-em-4-carboxylate (0.58 g 1.1 mmol) and N,N'-dicyclohexylcarbodiimide (0.44 g, 201 mmol) in dichloromethane (50 ml). The reaction mixture was stirred at room temperature for two days, then washed with N.hydrochloric acid, saturated sodium hydrogen carbonate solution, brine, dried over magnesium sulphate and evaporated. The product was contaminated with some of the L-enantiomer, but chromatography (silica gel, 1%–5% acetone in ethyl acetate gave the pure title compound (0.26 g, 30%); δ (CDCl$_3$) 1.18 (3H, m, CH$_2$CH$_3$), 2.23, 2.24 (6H, 2s, OCOCH$_3$), 2.76, 3.04 (2H, ABq, J 16.5 Hz, 2-H$_2$), 3.37–3.69 (4H, m, piperazine CH$_2$ and CH$_2$CH$_3$), 3.84 (3H, s, NCH$_3$), 3.9–4.1 (2H, m, piperazine CH$_2$), 4.27, 4.58 (2H, ABq, J 13.5 Hz, CH$_2$S), 5.18 (1H, s, 6-H), 5.60 (1H, d, J 7 HZ, ArCH), 6.88 (1H, s, CHPh$_2$), 7.03–7.60 (13H, m, aromatic-H's), 8.01 (1H, s, NH), 8.10 (1H, s, CHO), 8.61 (1H, s, NH), 10.07 (1H, d, J 7 Hz, NH); $\nu_{max}$ (CH$_2$Cl$_2$) 1779, 1718, 1689 cm$^{-1}$.

(b) 7β-[D-2-(3,4-Diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid, sodium salt Diphenylmethyl 7β-[D-2-(3,4-diacetoxyphenyl)-2-[(4-ethyl-2,3-dioxopiperazin-1-yl)carbonyl amino]acetamido]-7α-formamido-3-[(1-methyl-1H-tetrazol-5-yl)thiomethyl]-ceph-3-em-4-carboxylate (0.17 g) in trifluoroacetic acid (5 ml) was stirred at room temperature for 0.5 h and evaporated to dryness. The residue was triturated with ether, taken up in water which was adjusted to pH 6.5 with saturated sodium hydrogen carbonate solution, washed with ethyl acetate and freeze dried to give the title compound (0.113 g, 70%); δ(D$_2$O), 1.21 (3H, t, J 7 Hz, CH$_2$CH$_3$), 2.34, 2.36 (6H, 2s, CH$_3$CO), 3.00, 3.39 (2H, ABq, J 17.5 Hz, 2-H), 3.53 (2H, q, J 7 Hz, CH$_2$CH$_3$), 3.6–3.8 (2H, m, piperazine CH$_2$), 3.8–4.2 (3H, m, piperazine CH$_2$ and 1H of CH$_2$S), 3.98 (3H, s, NCH$_3$), 4.24 (1H, d, J 13 Hz, 1H of CH$_2$S), 5.26 (1H, s, 6-H), 5.56 (1H, s, ArCH), 7.3–7.6 (3H, m, aromatic-H's), 8.15 (1H, s, CHO); $\nu_{max}$ (KBr) 3430, 1770, 1676, 1620 cm$^{-1}$.

(c) 7β-[D-2-[(4-ethyl-2,3-dioxopiperazin-1-yl)carbonylamino]-2-(3,4-dihydroxyphenyl)acetamido]-7α-formamido-3-[(1-methyl-1H-tetrazol-5-yl)thiomethyl]-ceph-3-em-4-carboxylic acid, sodium salt 7β-[D-2-(3,4-Diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid sodium salt (0.110 g) was stirred in dilute sodium hydrogen carbonate solution at pH 8.5 for 2 h. The reaction mixture was acidified to pH 2.0 saturated with sodium chloride and repeatedly extracted with a mixture of tetrahydrofuran and ethyl acetate (1:1). The combined extracts were washed with brine, dried over magnesium sulphate and evaporated. The residue was taken up in tetrahydrofuran and treated with 2N sodium ethyl hexanoate in 4-methylpentan-2-one (0.07 ml) and diluted with ether. The precipitate was filtered, washed with tetrahydrofuran, ether and dried to give the title compound (0.051 g, 57%); δ($D_2O$) 1.17 (3H, t, J 7 Hz, $CH_2CH_3$), 3.11 (1H, d, J 17 Hz, 1H of 2-H), 3.35–3.58 (3H, m, $CH_2CH_3$ and 1H of 2-H), 3.58–3.79 (2H, m, piperazine $CH_2$), 3.93 (3H, s, $NCH_3$), 3.80–4.07 (3H, m, piperazine $CH_2$ and 1H of $CH_2S$), 4.13 (1H, d, J 14 Hz, 1H of $CH_2S$), 5.24 (1H, s, 6-H), 5.33 (1H, s, ArCH), 6.83–7.06 (3H, m, aromatic-H's), 8.11 (1H, s, CHO); $\nu_{max}$ (KBr) 3400 br, 2980, 1770, 1723, and 1678 $cm^{-1}$.

(d) Sodium 7β-[D-2-[(4-Ethyl-2,3-dioxopiperazin-1-yl]carbonylamino)-2(3,4-dihydroxyphenyl)acetamido]-7α-formamido-3-[(1-methyl-1H-tetrazol-2-yl)thiomethyl]-ceph-3-em-4-carboxylate-1-oxide Sodium 7β-[D-2-([4-ethyl-2,3-dioxopiperazin-1-yl]carbonylamino)-3,4-(dihydroxyphenyl)acetamido]-7α-formamido-3-[(1-methyl-1H-tetrazol-5-yl)thiomethyl]ceph-3-em-4-carboxylate (42 mg; 0.06 mmol) was dissolved in water (2 ml), cooled in ice and peracetic acid (9 μl of 52.8% solution in acetic acid; 0.066 mmol) added. After stirring for 1 h. the pH was adjusted to 6.5 using sodium bicarbonate solution and the reaction mixture purified using Diaion HP20SS. Lyophilisation of the relevant fractions gave the title compound (28 mg; 65%) as a mixture of R and S-sulphoxides $\lambda_{max}$. 268 nm, (εm 13,232); $\nu_{max}$. (KBr) 3428, 1783, 1710, 1676, 1611, 1030 $cm^{-1}$; δppm ($D_2O$) inter alia 1.18 (3H, t, J 8 Hz), 3.5 (2H, q, J 8 Hz), 3.68 (4H, m), 3.97 and 3.99 (together 3H, s) overlaps 3.8–4.05 (2H, m), 4.1–4.35 (2H, m), 5.30 and 5.34 (together 1H, s), 6.8–7.0 (3H, m), 8.1 and 8.18 (together 1H, s).

MIC against P.mirabilis 889 is 0.25 μl/ml.

EXAMPLE 7

7β-[D-2-[(4-Ethyl-2,3-dioxopiperazin-1-yl)carbonyl amino]-2-phenylacetamido]-7α-formamido-3-pyridiniummethyl-ceph-3-em-4-carboxylate-1-oxide (a) 7β-Amino-7α-formamido-3-(1-pyridiniummethyl)ceph-3-em-4-carboxylate 7β-Amino-7α-formamido-cephalosporanic acid, trifluoroacetic acid salt (600 mg; 1.4 mmol) in water (approx. 10 ml) was treated with sodium iodide (2.0 g) and pyridine (1.0 ml). The mixture was heated at 60° C. with stirring for approximately 4.5 h. The mixture was cooled and concentrated at reduced pressure. 'Dianion' HP 20SS chromatography followed by lyophilization gave the product (300 mg). $\nu_{max}$. (KBr) 3390 (br), 3260 (sh), 1765, 1670 and 1610 $cm^{-1}$; δppm ($D_2O$) (90 MHz) 3.13 and 3.59 (ABq, 2H, J 18 Hz), 5.36 (AA', 2H), 7.95 to 8.20 (m, 3H), 8.56 (d. 1H, J 8 Hz), 8.89 (d, 2H, J 8 Hz).

(b) D-2-[(4-Ethyl-2,3-dioxopiperazin-1-yl)carbonylamino]2-phenylacetyl chloride

D-2-[(4-Ethyl-2,3-dioxopiperazin-1-yl)carbonylamino]-2-phenylacetic acid (191 mg; 0.6 mmol) in dry dichloromethane (10 ml) containing a trace of dry N,N-dimethylformamide (DMF) was treated with oxalyl chloride (152 mg; 1.2 mmol). After stirring for approximately 1 hour at ambient temperature the mixture was evaporated to dryness. The residue was dissolved in more dry dichloromethane (5 ml) and re-evaporated and the residue dried in vacuo.

(c) 7β-[D-2-[(4-Ethyl-2,3-dioxopiperazin-1-yl)carbonylamino]-2-phenylacetamido]-7α-formamido-3-pyridiniummethyl-ceph-3-em-4-carboxylate.

7β-Amino-7α-formamido-3-pyridiniummethyl-ceph-3-em-4-carboxylate (167 mg; 0.5 mmol) suspended in dry dichloromethane (10 ml) was treated with N,N-dimethylaniline (485 mg; 4.0 mmol) and trimethylchlorosilane (217 mg; 2.0 mmol). The mixture was heated at reflux, with stirring, for approximately 1 hour, then cooled to ambient temperature.

A solution of (b) in dry MDC (10 ml) was added and the mixture stirred for approximately 16 hour. The solution was extracted with water ($\times 3$) and the combined extracts washed with dichloromethane. The aqueous phase was concentrated and chromatographed on 'Dianion' HP20SS resin to give the title compound (165 mg). $\nu_{max}$. (KBr) 3400, 3270, 1780, 1710 (sh), 1670 and 1620 $cm^{-1}$; δppm ($D_2O$) (250 MHz) 1.18 (3H, t, J 7 Hz), 2.85 (1H, ½ABq, J 18 Hz), 3.35 to 3.57 (3H, m), 3.58 to 3.76 (2H, m), 3.80 to 4.10 (2H, m), 5.22 and 5.40 (2H, ABq, J 15 Hz), 5.33 (1H, s), 7.30 to 7.58 (5H, m), 8.00 to 8.12 (2H, m), 8.14 (1H, s), 8.50 to 8.62 (1H, m), 8.8 to 9.0 (2H, m).

MIC (μg/ml) Proteus mirabilis 889 is 0.5.

(c) 7β-[2-[(4-ethyl-2,3-dioxopiperazin-1-yl)carbonylamino]-2-phenylacetamido]-7α-formamido-3-pyridiniummethyl-ceph-3-em-4-carboxylate-1-oxide 7-β-[2-[(4-Ethyl-2,3-dioxopiperazin-1-yl)carbonylamino]-2-phenylacetamido]-7α-formamido-3-pyridiniummethyl-ceph-3-em-4-carboxylate (50 mg, 0.079 mmol) was dissolved in water (3 ml), cooled (ice bath), and treated with 5.36% (w/v) peracetic acid/acetic acid (0.10 ml). The mixture was stirred for approximately 1 h (HPLC control), then a further portion of 5.36% (w/v) peracetic acid/acetic acid (0.022 ml) added. After a further 20 min HPLC examination of the mixture still showed starting material. A further portion of 5.36% (w/v) peracetic acid/acetic acid (0.022 ml) was added. After 20 min (HPLC control) the mixture was concentrated at reduced pressure and chromatographed on 'Dianion' HP2055 resin. The product containing fractions were combined, concentrated at reduced pressure and the concentrate freeze dried to give the title compound (39 mg, 76%), as a mixture of isomers.

$\nu_{max}$ (KBr) 3423, 3300, 1790, 1710 (sh), 1675, 1628 and 1497 $cm^{-1}$; δppm (250 mHz) ($D_2O$) inter alia 1.20 (3H, J 7.5 Hz), 3.4 to 3.8 (6H, m), 3.9 to 4.15 (2H, m), 5.17 (1H,s), 5.51 (1H, s), 5.2 to 5.6 (2H, m), 7.35 to 7.6 (5H, m), 7.95 to 8.15 (2H, m), 8.17 (1H, s), 8.45 to 2.65 (1H, m), 8.8 to 9.0 (2H, m).

Mass spectrum (FAB); 652 ($MH^+$).

MIC against P.mirabilis 889 is 8.0 μg/ml.

EXAMPLE 8

Sodium
7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylate-1α-oxide and sodium
7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylate-1β-oxide (a) Diphenylmethyl 7β-[D-2-[(4-Ethyl-2,3-dioxopiperazin-1-yl)-carbonylamino]-2-phenylacetamido]-7α-formamido-3-[(1-methyl-1H-tetrazol-5-yl)thiomethyl]-ceph-3-em-4-carboxylate D-2-[(4-Ethyl-2,3-dioxopiperazin-1-yl)carbonylamino]-2-phenylacetic acid (96 mg, 0.3 mmol) in dichloromethane (3 ml) containing dimethylformamide (1/10th of a drop) was treated with oxalyl chloride (0.06 ml; 0.6 mmol). After stirring at room temperature for 1 h, the reaction mixture was evaporated to dryness. The resulting acid chloride was dissolved in dichloromethane (3 ml) at −10° C. and diphenylmethyl 7β-amino-7α-formamido-3-[(1-methyl-1H-tetrazol-5-yl)thiomethyl]ceph-3-em-4-carboxylate (107 mg, 0.2 mmol) added, followed by pyridine (16 mg; 0.22 mmol) in dichloromethane (0.5 ml). After 10 min. the solution was washed with N. hydrochloric acid, saturated sodium hydrogen carbonate solution, brine, dried, and evaporated. The crude product was chromatographed on silica gel 60 (<230 mesh ASTM) eluting with 2% methanol/ethyl acetate, to afford the title compound (116 mg, 70%) δ ((CD$_3$)$_2$CO) 1.23 (3H, t, J 7 Hz, CH$_2$CH$_3$), 3.22 and 3.34 (2H, ABq, J 17 Hz, 2-H$_2$), 3.48 (2H, q, J 7 Hz, CH$_2$CH$_3$), 3.68 (2H, m), 3.94 (3H, s, N-CH$_3$), 4.3 (2H, m), 4.3 and 4.52 (2H, ABq, J 14 Hz, CH$_2$S Tet), 5.25 (1H, s, C-6), 5.71 (1H, d, J 7 Hz, collapses to s on D$_2$O exch.), 6.9 (1H, s, Ph$_2$CH), 7.2–7.7 (5H, m, phenyls), 8.28 (1H, s, CHO), 8.42 (1H, broad s, exch. D$_2$O), 8.71 (1H, broads, exch. D$_2$O) 10.02 (1H, d, J 7 Hz, NH, exch. D$_2$O); $\nu_{max}$(CHCl$_3$) 3260, 1780, 1710, 1685 cm$^{-1}$.

(b) 7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]ceph-3-em-4-carboxylic acid, sodium salt Diphenylmethyl 7β-[D-2-[(4-ethyl-2,3-dioxopiperazin-1-1)-carbonylamino]-2-phenylacetamido]-7α-formamido-3[(1-methyl-1H-tetrazol-5-yl)thiomethyl]ceph-3-em-4-carboxylate (104 mg; 0.12 mmol) was dissolved in trifluoroacetic acid (5 ml). After 30 min. the reaction solution was evaporated to dryness, treated with sodium hydrogen carbonate (11 mg) in water (1 ml), with vigorous stirring. The mixture was chromatographed on Dianion HP20SS eluting with acetone-water mixtures. The relevant fractions were partially evaporated to remove actone, then freeze dried to afford the title compound (47 mg, 55%); δ(D$_2$O) 1.27 (3H, t, J 7 Hz, CH$_2$CH$_3$), 3.05 and 3.42 (2H, ABq, J 17 Hz, 2-H$_2$), 3.49 (2H, q, J 7 Hz, CH$_2$CH$_3$) 3.66 (2H, m), 3.94 (3H, s, N-Me), the latter signal obscures a two proton multiplet and the higher field arm of an AB quartet, 4.17 (1H, part of ABq, 13.5 Hz, CH$_2$ STet), 5.18 and 5.22 (together 1H, s, C-6), 5.44 and 5.48 (together 1H, s, PhCH), 7.3–7.6 (5H, m, phenyl), 8.1 and 8.42 (together 1H, s, CHO); $\nu_{max\,(KBr)}$ 3400 br, 1770, 1710, 1680, 1605 cm$^{-1}$.

MIC (μg/ml) against *P. mirabilis* 889 is 0.125.

(c) Diphenylmethyl
7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylate-1α-oxide and diphenylmethyl 7β-[D-2-[(4-ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylate-1β-oxide Diphenylmethyl
7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylate (263 mg; 0.31 mmol) was dissolved in dichloromethane (5 ml), cooled to −20° and peracetic acid (42 μl of a 52.8% solution in acetic acid; 0.34 mmol) added. After 1.75 h. warming to room temperature, the solution was evaporated to dryness. Toluene was added to the residue and the suspension re-evaporated; this process was repeated. Chromatography on silica gel afforded the title products. β-isomer (65 mg; 27%) $\nu_{max}$ (CHCl$_3$) 1800, 1715, 1690, 1060 cm$^{-1}$; δppm [(CD$_3$)$_2$CO] inter alia 1.13 (3H, t, J 7 Hz), 3.48 (2H, q, J 7 Hz), 3.66 (2H, m), 3.89 (3H, s), overlaps 3.8–3.96 (2H, m), 4.04 (2H, m), 4.15–4.60 (2H, complex m), 5.01 and 5.10 (together 1H, s), 5.70 and 5.80 (together 1H, d, J 6 Hz, collapses to s, on exch.) 6.96 (1H, s), 7.2–7.7 (15H, m), 8.22 and 8.52 (together 1H, s), 8.50 (1H, s, exch.), 9.12 and 9.29 (together 1H, s, exch.), 9.99 (1H, d, J 6 Hz, exch.). α-isomer (91 mg; 34%). $\nu_{max}$ (CHCl$_3$) 1800, 1718, 1690, 1065 cm$^{-1}$; δppm [(CD$_3$)$_2$CO] inter alia 1.15 (3H, t, J 7 Hz), 3.52 (2H, q, J 7 Hz), 3.72 (2H, m) overlaps 3.7–3.9 (2H, m), 3.92 (3H, s), 4.05 (2H, m), 4.27 and 5.01 (2H, ABq, J 14 Hz), 4.51 (1H, s), 5.70 (1H, d, J 6 Hz, collapses to s, on exch.), 6.98 (1H, s), 7.2–7.7 (15H, m), 8.33 (1H, s), 8.98 (1H, s, exch.), 9.07 (1H, s, exch.), 9.96 (1H, d, J 6 Hz, exch.).

(d) Sodium 7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]ceph-3-em-4-carboxylate-1α-oxide Diphenylmethyl 7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylate-1α-oxide (77 mg; 0.09 mmol) was dissolved in trifluoroacetic acid (1.5 ml) at room temperature. After 10 min. the solution was evaporated to dryness, toluene added and the suspension re-evaporated; this process was repeated. Trituration of the residue with ether gave a white solid which was suspended in water and the pH adjusted to 6.5 with dilute sodium hydrogencarbonate. Chromatography on Diaion HP20SS and lyophilisation of the product containing fractions gave the title compound (40 mg; 65%). $\lambda_{max}$ 261 nm, (ϵm 12343); $\nu_{max}$ (KBr) 3433, 1785, 1710, 1677, 1650, 1614, 1036 cm$^{-1}$; δppm (D$_2$O) inter alia 1.18 (3H, t, J 7 Hz), 3.50 (2H, q, J 7 Hz) 3.69 (3H, m), 3.99 (3H, s) overlaps 3.8–4.2 (4H, m), 4.30 (1H, lower field arm of ABq, J 17 Hz; higher field arm obscured), 4.98 (1H, s), 5.54 (1H, s), 7.50 (5H, s), 8.19 (1H, s).

MIC against *P. Mirabilis* 889 is 0.25 μg.ml$^{-1}$.

(e) Sodium 7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]ceph-3-em-4-carboxylate-1β-oxide Diphenylmethyl 7β-[D-2-[(4-ethyl-2,3-dioxopiperazin-1-yl)carbonylamino]-2-phenylacetamido]-7α-formamido-3-[(1-methyl-1H-tetrazol-5-yl)thiomethyl]- ceph-3-em-4-carboxylate-1β-oxide (47 mg; 0.05 mmol) was converted to the title product (33 mg; 87%) as described in example 8d λ$_{max}$ 265 nm, (εm 11782); ν$_{max}$ (KBr) 3427, 1790, 1710, 1678, 1063 cm$^{-1}$; δppm (D2O) inter alia 1.12 (3H, t, J 7 Hz), 3.52 (2H, q, J 7 Hz), 3.71 (4H, m), 4.00 (3H, s) overlaps 3.9–4.1 (3H, m), 4.27 (1H, lower field arm of ABq, J 16 Hz; higher field arm obscured), 5.07 (1H, s), 5.49 (1H, s), 7.4–7.6 (5H, m), 8.12 (1H, s).

MIC against *P. mirabilis* 889 is 0.5 μg.ml$^{-1}$.

EXAMPLE 9

Benzyl 6β-amino-6α-formamidopenicillanate-1-oxide, Isomer B.

(a) Benzyl 6β-[(2,2,2-trichloroethoxy)carbonylamino]-6α-formamidopenicillanate-1-oxide, Isomers A and B.

Benzyl 6β-[(2,2,2-trichloroethoxy)carbonylamino]-6α-formamidopenicillanate (5.00 g) (see UK Patent Application GB No. 2,107,307A), was dissolved in 1,2-dichloroethane (75 ml) and stirred at 0° C. It was treated with m-chloroperbenzoic acid (1.81 g), and after a reaction period of 1 hour the product was diluted with ethyl acetate (50 ml), washed with aqueous sodium hydrogen carbonate, brine and dried over sodium sulphate. This solution was concentrated to a gum and redissolved in ethyl acetate (15 ml) to which hexane was added to the point of turbidity. From this crystallised the more polar isomer B of benzyl 6β-[(2,2,2-trichloroethoxy)carbonylamino]-6α-formamido penicillanate-1-oxide (2.45 g); m.p. 149°–151° C.; ν$_{max}$ (CHCl3) 3400, 3260, 2980, 1800, 1735, 1700 and 1495 cm$^{-1}$; δ(CDCl3) 1.22 and 1.48 (6H, 2s, 2-CH3's), 4.54 (1H, s, 3-H), 4.67 and 4.89 (2H, ABq, J 12Hz, CH2CCl3), 5.12 (1H, s, 5-H), 5.20 (2H, s, CH2Ph), 7.25 and 7.97 (2H, 2br, s, NH's) 7.34 (5H, s, phenyl) and 8.18 (1H, s, CHO); (Found: C, 42.2; H, 3.7; N, 7.7; S, 5.5%. C19H20Cl3N3O7S requires C, 42.2; H, 3.7; N, 7.8; S, 5.9%). The mother liquors were chromatographed on silica gel 60, eluting with ethyl acetate/hexane 6:4, to give the less polar isomer A as a colourless foam (1.02 g); ν$_{max}$ (CHCl3), 3400, 3250, 2980, 1800, 1735, 1705, and 1500 cm$^{-1}$; δ(CDCl3) 1.09 and 1.60 (6H, 2s, 2-CH3's), 4.69 (1H, s, 3-H), 4.71 (2H, s, CH2CCl3), 5.11 and 5.31 (2H, ABq, J12 Hz, CH2Ph), 5.20 (1H, s, 5-H), 7.27 and 7.53 (2H, 2br s, NH's), 7.35 (5H, s, phenyl) and 8.22 (1H, s, CHO); (Found: MH$^+$540 by; +ve ion FAB. C19H20Cl3N3O7S required M 539); plus further isomer B (0.46 g).

(b) Benzyl 6β-amino-6α-formamidopenicillanate-1-oxide, Isomer B.

A vigorously stirred mixture of benzyl 6β-[(2,2,2-trichloroethoxy)carbonylamino]-6α-formamidopenicillanate-1-oxide, Isomer B (0.500 g) in tetrahydrofuran (10 ml) and aqueous M.potassium dihydrogen phosphate (1 ml) was treated with freshly acid-washed zinc powder (0.700 g). As the reaction proceeded, the pH was maintained at 4 to 6 by addition of M.hydrochloric acid and the progress was monitored by thin layer chromatography. Further zinc (0.500 g) was added after 1.5 hour and deprotection was complete in a total 3 hour. The reaction product was then filtered through Celite and the filtrate concentrated until turbid. It was partitioned between ethyl acetate and water, and the organic phase was separated, washed with brine, dried over sodium sulphate, and concentrated to a gum. This crude benzyl 6β-amino-6α-formamidopenicillanate-1-oxide, Isomer B (0.290 g) was suitable for further reaction, but it could be chromatographed on silica gel 60 eluting with chloroform/ethanol 9:1 to give purer material; ν$_{max}$ (CHCl3) 3380, 3300, 2980, 1790, 1740, 1690 and 1030 cm$^{-1}$; δ(CDCl3) 1.33 and 1.48 (6H, 2s, 2-CH3's), 2.67 (2H, br s, NH2), 4.56 (1H, s, 3-H), 5.04 (1H, s, 5-H), 5.17 (2H, s, CH2Ph), 7.34 (5H, s, phenyl), 7.64 (1H, s, NH) and 8.18 (1H, s, CHO).

EXAMPLE 10

Benzyl 6β-(2,2,2-trichloroetthoxycarbonylamino)-6α-formamidopenicillanate-1α-oxide (a) Benzyl 6-(N-2,2,2-trichloroethoxycarbonyl-N-trifluoromethanesulphonylamino)penicillanate-1α-oxide Benzyl 6-(N-2,2,2-trichloroethoxycarbonyl-N-trifluoromethanesulphonylamino)penicillanate (613 mg) was dissolved in dry dichloromethane (10 ml) at −10° C. and peracetic acid (1.5 ml of 5.24% solution in acetic acid) was added. After 16 hours at 0° C. the solvent was evaporated in vacuo. After addition of toluene and repetition of the evaporation (three times), the residue was chromatographed on silica gel to give the title compound (516 mg). ν$_{max}$ (CHCl3) 1810, 1755, 1425, 1130 cm$^{-1}$; δ(CDCl3) 1.18 and 1.68 (6H, 2s, (CH3)2C), 4.45 (1H, s, 3-H), 4.73 (1H, d, J 4.5 Hz), 4.81 and 4.97 (2H, ABq, J 12 Hz), 5.21 (2H, AA$^1$), 5.7 (1H, d, J 4.5 Hz), 7.35 (5H, s, aromatics).

(b) Benzyl 6β-(2,2,2-trichloroethoxycarbonylamino)-6α-formamido penicillanate-1-α-oxide.

Benzyl 6-(N-2,2,2-trichloroethoxycarbonyl-N-trifluoro-1α-methanesulphonylamino)penicillanate-1-α-oxide (63 mg) was dissolved in dry dichloromethane (2 ml) at −10° C. and bistrimethylsilylformamide (40 mg) was added, followed immediately by triethylamine (10 mg). The temperature was allowed to rise to −5° C. and after 40 minutes the solution was poured into ethyl acetate and washed successively with dilute hydrochloric acid, brine, dried, and evaporated. Chromatography on silica gel afforded the title compound; ν$_{max}$ (CHCl3) 3200 (broad), 1800, 1740, 1700 cm$^{-1}$; δ(CDCl3) 1.25 and 1.48 (6H, 2s, (CH3)2C), 4.56 (1H, s, 3-H), 4.68 and 4.89 (2H, Abq, J 13 Hz), 5.16 (1H, s), 5.2 (2H, AA$^1$) 7.2b(1H, s, exch. D2O) 7.33 (5H, s, aromatics), 8.03b(1H, s, exch D2O), 8.17 (1H, s, CHO).

EXAMPLE 11

(a) Benzyl 6β-(trifluoromethanesulphonyl)aminopenicileanate-1β-oxide.

Benzyl 6β-(trifluoromethanesulphonyl)aminopenicillanate (3.12 g) was dissolved in dry dichloromethane (50 ml) at −10° C. and peracetic acid (1 ml of 52.4% solution in acetic acid) added. After 15 minutes the solvent was evaporated. After addition of toluene and repetition of the evaporation (three times), the residue was chromatographed on silica gel to give the title compound (2.6 g); ν$_{max}$ 3250, 1810, 1750, 1440, 1140 cm$^{-1}$; δ(CDCl3) 1.05 and 1.64 (6H, 2s, (CH3)2C), 4.69 (1H, s, 3-H), 4.98 (1H, d, J 4.5 Hz), 5.1 and 5.28 (2H, ABq, J 12 Hz), 5.31 (1H, d, J 4.5 Hz), 7.34 (5H, s, aromatics).

(b) Benzyl 6-(N-2,2,2-trichloroethoxycarbonyl-N-trifluoromethanesulphonylamino)penicillanate-1β-oxide.

Benzyl 6β-(trifluoromethanesulphonyl)aminopenicillanate-1β-oxide (988 mg) was dissolved in dry dichloromethane (30 ml) at −10° C. and trichloroethylchloroformate (844 mg) added, followed by pyridine (240 mg). The temperature was raised to 0° C. and after 1½ hour the reaction mixture was poured into ethyl acetate/dilute hydrochloric acid. The organic layer was separated, washed with brine, dried and evaporated. Chromatography on silica gel gave the title compound (1.14 g); $v_{max}$ 1815, 1750, 1420, 1125, 1045 cm$^{-1}$; $\delta$(CDCl$_3$) 1.05 and 1.6 (6H, 2s, (CH$_3$)$_2$C), 4.7 (1H, s, 3-H), 4.88 (2H, AA'), 5.01 (1H, d, J 5 Hz), 5.13 and 5.3 (2H, ABq, J 12 Hz), 5.52 (1H, s, J 5 Hz), 7.34 (5H, s, aromatics).

(c) Benzyl 6$\beta$-(2,2,2-trichloroethoxycarbonylamino)-6$\alpha$-formamidopenicillanate-1$\beta$-oxide Benzyl 6-(N-2,2,2-trichloroethoxycarbonyl-N-trifluoromethanesulphonylamino)penicillanate-1$\beta$-oxide (126 mg) was dissolved in dry dichloromethane (3 ml) at −10° C. and bis(trimethylsilyl)formamide (80 mg) was added, followed immediately by triethylamine (20 mg). After 20 min at −10° C./−5° C. the solution was poured into ethyl acetate, and washed with dilute hydrochloric acid, followed by brine, dried and evaporated. Chromatography on silica gel afforded the title compound; $v_{max}$ (CHCl$_3$) 3400, 3250, 1795, 1735 (broad), 1700, 1050 cm$^{-1}$; $\delta$(CDCl$_3$) 1.06 and 1.6 (6H, 2s, (CH$_3$)$_2$C), 4.68 (1H, s, 3-H), 4.72 (2H, AA'), 5.2 (1H, s), 5.13 and 5.32 (2H, ABq, J 12 Hz), 7.35 (5H, s, aromatics), obscures one NH, 1H, s, exch. D$_2$O), 8.22 (1H, s, CHO).

EXAMPLE 12

Benzyl 6$\alpha$-formamido-6$\beta$-(phenylacetamido)penicillanate-1$\beta$-oxide A solution of benzyl 6$\alpha$-methylsulphinyl-6$\beta$-(phenylacetamido)penicillanate-1$\beta$-oxide (80 mg, 0.159 mmol) in dry tetrahydrofuran (5 ml) and bis-(trimethylsilyl)formamide (120 mg, 0.635 mmol) was heated under reflux for 6 h and then allowed to stand at room temperature for 18 h. The solvent was then evaporated in vacuo and the residue taken up in ethyl acetate (15 ml). The solution was washed successively with 2N-hydrochloric acid (10 ml) and saturated brine (10 ml), dried (MgSO$_4$) and evaporated. Chromatography of the crude product on silica gel gave the title compound (30 mg, 39%), $v_{max}$ (CHCl$_3$) 3250, 2930, 1795, 1745, and 1680 cm$^{-1}$; $\delta$(CDCl$_3$) 1.01 and 1.56 (3H, s), 3.53 (2H, s), 4.72 (1H, s), 5.08 (1H, s), 5.24 (2H, ABq, J 12 Hz), 7.26 (s, 5H), 7.37 (s, 5H), 7.78 br (s, 1H), 7.90 br (s, 1H) and 7.99 and 8.33 (each s, together 1H), (addition of D$_2$O caused the signals at 7.78 and 7.90 to disappear).

EXAMPLE 13 t-Butyl 7$\beta$-[2,2,2-trichloroethoxycarbonylamino)-7$\alpha$-formamidocephalosporanate-1-oxide t-Butyl 7$\beta$-(2,2,2-trichloroethoxycarbonylamino)-7$\alpha$-formamidocephalosporanate (546 mg) was dissolved in dry dichloromethane (10 ml) at −20° C. and peracetic acid (1.6 ml of 5.2% w/v solution in acetic acid) added. After 30 min further peracetic acid (0.36 ml) was added and the mixture stirred at 0° C. for 1 h and then the solvent was evaporated in vacuo. After addition of toluene and repetition of the evaporation (twice), the residue was chromatographed on silica gel, to give the two isomers of the title compound.

Isomer A (less polar tlc)-$\beta$-isomer (164 mg): $v_{max}$ (CHCl$_3$) 3390, 3250, 1800, 1720, 1065, 1040 cm$^{-1}$; $\delta$(CDCl$_3$) inter alia 1.57 (9H, s, C(CH$_3$)$_3$), 2.07 (3H, s, OCOCH$_3$), 3.34 (1H, d, J 18.5 Hz, part of AB quartet, showing fine coupling of 1.2 Hz, removed by irradiation at 4,87), 3.75 (1H, d, J 18.5 Hz, part of ABq), 4.67 and 5.16 (2H, ABq, J 13.5 Hz), 4.77 (2H, AA'), 4.87 (1H, d, J 1.5 Hz, 6-H), 7.36 (1H, s), 7.58 (1H, slightly broadened s), 8.23 (1H, s, CHO). Isomer B (more polar tlc)-: $\alpha$-isomer (208 mg); $v_{max}$ (CHCl$_3$) 3480, 3200 broad, 1805, 1730, 1700 sh, 1040 cm$^{-1}$; $\delta$(CDCl$_3$) inter alia 1.55 (9H, s, (CH$_3$)$_3$C), 2.11 (3H, s, OCOCH$_3$), 3.58 and 4.07 (2H, ABq, J 16.8 Hz, S-CH$_2$), 4.7–4.9 (3H, m), 4.91 (1H, s, 6-H), 5.11 (1H, part of ABq, J 13.6 Hz), 7.44 (1H, s), 8.16 (1H, broadened s), 8.27 (1H, s, CHO).

EXAMPLE 14

7$\beta$-[D-2-[(4-Ethyl-2,3-dioxopiperazin-1-yl)carbonylamino]-2-(4-hydroxyphenyl)acetamido]-7$\alpha$-formamidocephalosporanic acid 1-oxide, sodium salt (a) t-Butyl 7$\beta$-[D-2-[4-(benzyloxycarbonyloxy)phenyl]-2-[(4-ethyl-2,3-dioxopiperazin-1-yl)carbonylamino]acetamido]-7$\alpha$-formamidocephalosporanate-1-oxide t-Butyl 7$\beta$-[D-2-[4-(benzyloxycarbonyloxy)phenyl]-2-[(4-ethyl-2,3-dioxopiperazin-1-yl)carbonylamino]acetamido]-7$\alpha$-formamidocephalosporanate (324 mg) (see UK Patent app. No. GB2, 107,307A) was dissolved in dichloromethane (15 ml) at −20° C. and peracetic acid (0.75 ml of 5.2% w/v solution in acetic acid) added. The solvent was evaporated in vacuo. After addition of toluene and repetition of the evaporation (three times), the residue was chromatographed on silica gel to give the two isomers of the title compound.

Isomer A (less polar tlc); $\beta$-oxide (69 mg); $v_{max}$ (CHCl$_3$), 3260 br, 1795, 1715, 1690 cm$^{-1}$; $\delta$(CDCl$_3$), inter alia 1.22 (3H, t, J 7 Hz), 1.55 (9H, s, (CH$_3$)$_3$C), 2.06 (3H, s, OCOCH$_3$), 3.22 and 3.62 (2H, ABq, J 19 Hz, S-CH$_2$), 3.4–3.7 (4H, m), 4.0–4.2 (2H, m), 4.68 and 5.10 (2H, ABq, J 13 Hz), 4.87 (1H, slightly broadened singlet, 6-H), 5.24 (2H, s), 5.71 (1H, d, J 7 Hz, side-chain $\alpha$-CH), 7.1–7.6 (9H, m, aromatics), 7.93 (1H, s, exch. D$_2$O), 8.12 (1H, s, CHO), 8.68 (1H, slightly broadened s, exch. D$_2$O), 9.97 (1H, d, J 7 Hz, exch. D$_2$O).

Isomer B (more polar tlc); $\alpha$-oxide (168 mg); $v_{max}$ (CHCl$_3$) 3280, 1795, 1720, 1685 cm$^{-1}$; $\delta$(CDCl$_3$) 1.19 (1H, t, J 7 Hz), 1.52 (9H, s, (CH$_3$)$_3$C), 2.06 (3H, s, OCOCH$_3$), 3.3–3.7 (6H, m), 3.8–4.2 (2H, m), 4.76 and 5.08 (2H, ABq, J 14 Hz), 4.87 (1H, s, 6-H), 5.62 (1H, d, J 6 Hz, $\alpha$-proton), 7.1–7.6 (9H, m, aromatics), 8.22 (1H, s, CHO), 8.36b (1H, s, exch D$_2$O), 8.97b (1H, s, exch D$_2$O, 9.98 (1H, d, J 6 Hz, exch D$_2$O).

(b) t-Butyl 7$\beta$-[D-2-[(4-ethyl-2,3-dioxopiperazin-1-yl)carbonylamino]-2-(4-hydroxyphenyl)acetamido]-7$\alpha$-formamidocephalosporanate-1-oxide Isomer A; $\beta$-oxide A mixture of t-butyl 7$\beta$-[D-2-[4-(benzyloxycarbonyl)-phenyl]-2-[(4-ethyl-2,3-dioxopiperazin-1-yl)carbonylamino]acetamido]-7$\alpha$-formamidocephalosporanate-1-$\beta$-oxide (62 mg) and 10% Pd-C (60 mg) in dioxane (10 ml) was shaken under an atmosphere of hydrogen for 2 h. The catalyst was then filtered off, the filtrate evaporated, and chromatographed on silica gel, to give the $\beta$-oxide of the title compound (44 mg); $v_{max}$ (CHCl$_3$) 3270, 1795, 1715, 1690 cm$^{-1}$; $\delta$(CDCl$_3$+(CD$_3$)$_2$CO) inter alia 1.21 (3H, t, J 7 Hz), 1.55 (9H, s, (CH$_3$)$_3$C), 2.07 (3H, s, OCOCH$_3$), 3.34 (1H, d, part of ABq, J 18 Hz, showing further fine coupling removed by irradiation at 4.87), 3.5–3.8 (5H, m), 4.0–4.2 (2H, m), 4.63 and 5.13 (2H, ABq, J 13.6 Hz, CH$_2$OCO), 4.87 (1H, very slightly broadened s, J 1.1 Hz, 6-H), 5.54 (1H, d, J 6.7 Hz), 6.81 and 7.32 (4H, ABq, J 8.6 Hz, aromatics), 7.64 (5H, s, aromatics), 8.17 (1H, s, CHO), 8.20 (1H, s, exch D2O), 8.24 (1H, s, exch. D2O), 8.59 (1H, s, exch. D2O), 9.79 (1H, s, J 6.7 Hz exch. D2O).

Isomer B; α-oxide

A mixture of t-butyl 7β-[D-2-[4-(benzyloxycarbonyl)-phenyl]-2-[(4-ethyl-2,3-dioxopiperazin-1-yl)carbonylamino]acetamido]-7α-formamidocephalosporanate-1α-oxide (157 mg) and 10% Pd-C (150 mg) in tetrahydrofuran:dioxan (1:1, 10 ml) was shaken under an atmosphere of hydrogen for 2 h. Work-up as described for isomer A gave the α-oxide of the title compound (88 mg); $v_{max}$ (KBr) 3240, 1795, 1710, 1675, 1510 cm$^{-1}$; δ(CDCl$_3$+(CD$_3$)$_2$CO) inter alia 1.20 (3H, t, J 7 Hz), 1.53 (9H, s, (CH$_3$)$_3$C), 2.09 (3H, s, OCOCH$_3$), 3.4–3.7 (6H, m), 3.95–4.10 (2H, m), 4.85 (1H, s, 6-H), 4.85 and 5.09 (2H, ABq, J 14 Hz), 5.5 (1H, s not d, due to partial exch. of NH with solvent), 6.83 and 7.35 (4H, ABq, J 8 Hz, aromatics), 8.02 (1H, s, CHO), 8.40, 8.53, 9.0 (three weak broad s, partially exchanged by solvent), 9.8 (weak d, J 6 Hz, partial exch. with solvent).

(c) 7β-[D-2[(4-Ethyl-2,3-dioxopiperazin-1-yl)carbonylamino]-2-(4-hydroxyphenyl)acetamido]-7α-formamidocephalosporanic acid-1-oxide, sodium salt.

Isomer A—β-oxide t-Butyl 7β-[D-2[(4-ethyl-2,3-dioxopiperazin-1-yl)carbonylamino]-2-(4-hydroxyphenyl)acetamido]-7α-formamidocephalosporanate-1β-oxide (38 mg) was dissolved in trifluoroacetic acid (5 ml). After 30 min., toluene was added and the solvents evaporated. After addition of toluene and repetition of the evaporation (twice), the solid residue was suspended in water (3 ml) and the pH adjusted to 6.5 with dilute aqueous sodium hydrogen carbonate. The resulting solution was purified on HP20SS eluting with water/acetone mixtures. Partial evaporation and then lyophilisation of the relevant fractions gave the β-oxide of the title compound (27 mg); $v_{max}$ (KBr) 3310, 3240, 1780, 1710, 1675, 1610 cm$^{-1}$; δ(D$_2$O) inter alia 1.20 (3H, t, J 7.2 Hz), 2.09 (3H, s, OCOCH$_3$), 3.4–3.8 (6H, m), 3.9–4.1 (2H, m), 4.61 and 4.84 (2H, ABq, J 13 Hz), 5.08 (1H, s, 6-H), 5.43 (1H, s, α-CH), 6.91 and 7.38 (4H, ABq, J 8.6 Hz, aromatics), 8.15 (1H, s, CHO).

MIC against P. mirabilis 889 is 0.25 μg/ml.

Isomer B; α-oxide t-Butyl 7β[D-2[(4-ethyl-2,3-dioxopiperazin-1-yl)carbonylamino]-2-(4-hydroxyphenyl)acetamido]-7α-formamidocephalosporanate-1α-oxide (78 mg) was converted into the α-oxide of the title compound (66 mg) as described for isomer A; $v_{max}$ (KBr) 3310, 3240, 1785, 1710, 1670, 1610, 1510 cm$^{-1}$; δ(D$_2$O) inter alia 1.20 (3H, t, J 7.2 Hz), 2.11 (3H, s, OCOCH$_3$), 3.52 (2H, q, J 7.2 Hz), 3.57 and 4.11 (2H, obscured ABq, J 17 Hz), 3.71 (2H, m), 3.95–4.10 (2H, m), 4.65 and 4.88 (2H, ABq, J 12.8 Hz), 5.09 (1H, s, 6-H), 5.47 (1H, s, α-CH), 6.95 and 7.39 (4H, ABq, J 8.5 Hz, aromatics), 8.23 (1H, s, CHO).

MIC against P. mirabilis 889 is 0.12 μg/ml.

EXAMPLE 15

3-[(1-Carboxymethyl-1H-tetrazol-5-yl)-thiomethyl]-7β-[D-2(3,4-diacetoxyphenyl)-2-[(4-ethyl-2,3-dioxopiperazin-1-yl)carbonylamino]acetamido]-7α-formamidoceph-3-em-4-carboxylic acid-1-oxide, disodium salt (a) Diphenylmethyl 3-[(1-diphenylmethoxycarbonylmethyl-1H-tetrazol-5-yl)thiomethyl]-7β-[D-2(3,4-diacetoxyphenyl)-2-[(4-ethyl-2,3-dioxopiperazin-1-yl)carbonylamino]acetamido]-7α-formamidoceph-3-em-4-carboxylate-1-oxide Diphenylmethyl 3-[(1-diphenylmethoxycarbonylmethyl-1H-tetrazol-5-yl)thiomethyl]-7β-[D-2(3,4-diacetoxyphenyl)-2-[(4-ethyl-2,3-dioxopiperazin-1-yl)carbonylamino]acetamido]-7α-2,3-dioxopiperazin-1-yl)formamidoceph-3-em-4-carboxylate (347 mg) was dissolved in dry dichloromethane (6 ml) and methanol (6 ml) at −22° C. and peracetic acid (0.43 ml of a 0.695 mmol/ml solution in acetic acid) added. After 20 min, more peracetic acid (0.10 ml) was added and the mixture stirred at 0° C. for 30 min. The mixture was then diluted with more dichloromethane and washed with dilute aqueous sodium hydrogen carbonate, followed by saturated brine. The organic layer from above was dried (MgSO$_4$) and evaporated to give a yellow glass which was purified on silica gel to give the two isomers of the title compound.

Isomer A (less polar by t.l.c.; β-isomer); δ[(CD$_3$)$_2$CO] 1.14 (3H, t, J 7.5 Hz, N.CH$_2$.CH$_3$), 1.99 and 2.13 (each 3H, s, 2x OCOCH$_3$), 3.40–3.75 (together 6H, m, 2-CH$_2$, N.CH$_2$.CH$_3$ and N.CH$_2$.CH$_2$.N), 3.95–4.10 (2H, m, N.CH$_2$.CH$_2$.N), 4.17 [1H, high-field half of 3-CH$_2$SX ABq (J15 Hz)], 4.36 and 4.56 [together 1H, each d (J 15 Hz), low-field halves of 3-CH$_2$S, major and minor rotamer respectively], 4.97 br and 5.04 br (together 1H, each s, 6-H), 5.40–5.55 (2H, m, N.CH$_2$.CO$_2$), 5.78 and 5.84 [together 1H, each d (J 8 Hz), NH.CH.CO, minor and major rotamer respectively], 6.92 and 6.95 (2H, each s, 2x CHPh$_2$), 7.15–7.70 (23H, m, aromatics) 8.22 and 8.53 (together 1H, each s, NH.CHO, major and minor rotamer respectively), 8.53 br (1H, amide NH), 9.25 br and 9.41 br (together 1H, each s, amide NH), and 10.03 (1H, d, J 8 Hz, CH.NH.CO). (Addition of D$_2$O caused the signals at 9.41 and 9.25 to disappear, whilst that at 8.53 diminished in intensity).

Isomer B (more polar by t.l.c.; α-isomer): δ[(CD$_3$)$_2$CO] 1.13 (3H, t, J 7 Hz, N.CH$_2$.CH$_3$), 2.25 and 2.27 (each 3H, s, 2x OCOCH$_3$), 3.26 and 3.75 (2H, ABq, J 15 Hz, 2-CH$_2$), 3.47 (2H, q, J 7 Hz, N.CH$_2$.CH$_3$), 3.5–3.7 (2H, m, N.CH$_2$.CH$_2$.N), 3.9–4.1 (3H, m, N.CH$_2$.CH$_2$.N and high-field half of 3-CH$_2$S), 4.55 (1H, s, 6-H), 5.18 [1H, low-field half of 3-CH$_2$S (J 14 Hz)], 5.51 (2H, ABq, J 17 Hz, N.CH$_2$.CO$_2$), 5.76 (1H, d, J 7 Hz, NH.CH.CO), 6.94 and 6.96 (each 1H, s, 2x CHPh$_2$), 7.2–7.7 (23H, m, aromatics), 8.29 (1H, s, NH.CHO), 8.87 br and 9.11 br (each 1H, s, 2x amide NH), and 10.06 (1H, d, J 7.0 Hz, CH.NH.CO). (Addition of D$_2$O caused the signals at 8.87 and 9.11 to disappear).

(b) 3-[(1-Carboxymethyl-1H-tetrazol-5-yl)thiomethyl]-7β-[D-2(3,4-diacetoxyphenyl)-2-[(4-ethyl-2,3-dioxopiperazin-1-yl)carbonylamino]acetamido]-7α-formamidoceph-3-em-4-carboxylic acid-1-oxide, disodium salt Isomer A (β-Oxide);

Diphenylmethyl 3-[(1-diphenylmethoxycarbonylmethyl-1H-tetrazol-5-yl)thiomethyl]-7β-[D-2(3,4-diacetoxyphenyl)-2-[(4-ethyl-2,3-dioxopiperazin-1-yl)carbonylamino]acetamido]-7α-formamidoceph-3-em-4-carboxylate-1β-oxide (34 mg) was treated with trifluoroacetic acid (2 ml) at room temperature and the solvent then evaporated in vacuo. The residue was dissolved in dilute aqueous sodium hydrogen carbonate, pH adjusted to 6.8 and the solution chromatographed on Diaion HP20SS to afford the title compound as a white solid after lyophilisation (10 mg); $v_{max}$ (KBr) 3430, 3000, 1770, 1675, 1625, 1500 and 1064 cm$^{-1}$, δ(D$_2$O) 1.18 (3H, t, J 7 Hz, N.CH$_2$.CH$_3$), 2.35 (6H, s, 2x OCOCH$_3$), 3.50 (2H, q, J 7 Hz, N.CH$_2$.CH$_3$), 3.5–3.8 (4H, m, N.CH$_2$.CH$_2$.N and 2-CH$_2$), 3.9–4.1 (3H, m, N.CH$_2$.CH$_2$.N and high-field half of 3-CH$_2$S), 4.38 and 4.53 [together 1H, each d(J 14.5 Hz), low-field halves of 3-CH$_2$S, major and minor rotamer respectively], 4.99 (2H, s, N.CH$_2$.CO$_2$), 5.01 (1H, s, 6-H), 5.47 and 5.53 (1H, each s, NH.CH.CO, minor and major rotamer respectively), 7.25–7.55 (3H, m, aromatics), 8.11 and 8.47 (together 1H, each s, NH.CHO, major and minor rotamer respectively).

MIC (μg/ml) against *P. mirabilis* 889 is 0.5.

Isomer B (α-oxide);

Diphenylmethyl 3-[(1-diphenylmethoxycarbonylmethyl-1H-tetrazol-5-yl)thiomethyl]-7β-[D-2(3,4-diacetoxyphenyl)-2-[(4-ethyl-2,3-dioxopiperazin-1-yl)carbonylamino]acetamido]-7α-formamidoceph-3-em-4-carboxylate-α1-oxide (33 mg) was treated with trifluoroacetic acid as described for isomer A (β-oxide) to afford the title compound as a white solid (12 mg); ν$_{max}$. 3430, 2990, 1780, 1680, 1625, 1501, and 1015 cm$^{-1}$, δ(D$_2$O) inter alia 1.20 (3H, t, J 14.5 Hz, N.CH$_2$.CH$_3$), 2.35 (6H, s, 2x OCOCH$_3$), 3.53 (2H, q, J 14.5 Hz, N.CH$_2$.CH$_3$), 3.6–3.85 (4H, m, N.CH$_2$.CH$_2$.N and 2-CH$_2$S), 3.9–4.1 (3H, m, N.CH$_2$.CH$_2$.N and high-field half of 3-CH$_2$S), 4.39 (1H, d, J 14 Hz, low-field half of 3-CH$_2$S ABq), 5.03 (2H, s, N.CH$_2$.CO$_2$), 5.05 (1H, s, 6-H), 5.60 (1H, s, NH.CH.CO), 7.3–7.6 (3H, m, aromatics), and 8.21 and 8.43 (together 1H, each s, NH.CHO).

MIC (μg/ml) against *P. mirabilis* 889 is 0.25.

EXAMPLE 16

Sodium 7β-[D-2-(3,4-dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1-oxide (a) Diphenylmethyl 7β-[D-2-(3,4-Diacetoxyphenyl)-2-([4-ethyl-2,3-dioxopiperazin-1-yl]carboxylamino)acetamido]-7α-formamido-3-[(1-methyl-1H-tetrazol-5-yl)thiomethyl]-ceph-3-em-4-carboxylate D-2-(3,4-Diacetoxyphenyl)-2-[(4-ethyl-2,3-dioxopiperazin-1-yl)carbonylamino]acetic acid (1.024 g; 2.3 mmol) in anhydrous dichloromethhane (20 ml) containing a catalytic amount of dimethylformamide, was cooled at 0° C. and oxalyl chloride (0.656 g; 5.17 mmol) added. After stirring at room temperature for 1 hr., the solution was evaporated to dryness, the residue redissolved in dichloromethane and the solution evaporated; this was repeated. The resulting acid chloride was taken up in dichloromethane (8 ml) and added to diphenylmethyl 7β-amino-7α-formamido-3-[(1-methyl-1H-tetrazol-5-yl)thiomethyl]-ceph-3-em-4-carboxylate (0.632 g; 1.17 mmol) (see U.K. Patent Application No. 2107307A) in dichloromethane (12 ml) at −20° C., followed by pyridine (0.102 g; 1.3 mmol) in dichloromethane (0.5 ml). After stirring it −20° C. to 0° C. for 1 h., the reaction was diluted with ethyl acetate and washed with dilute hydrochloric acid, brine, dilute sodium hydrogencarbonate, brine, dried (MgSO$_4$) and evaporated. Chromatography of the residue on silica gel gave the title product (0.8 g; 74%) which was identical with Example 57 isomer 2 U.K. Patent Application No. 2107307A.

(b) Sodium 7β-[D-2-(3,4-Diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate Diphenylmethyl 7β-[D-2-(3,4-diacetoxyphenyl)-2-[(4-ethyl-2,3-dioxopiperazin-1-yl)carboxylamino]acetamido]-7α-formamido-3-[(1-methyl-1H-tetrazol-5-yl)thiomethyl]-ceph-3-em-4-carboxylate (0.6 g; 0.62 mmol) was dissolved in trifluoroacetic acid (10 ml) at room temperature. After 10 min. the solution was evaporated to dryness, toluene added and the suspension re-evaporated. This process was repeated. The residue was triturated with ether to give a white solid which was suspended in water (3–4 ml) and the pH adjusted to 6.5 with dilute sodium hydrogencarbonate. Chromatograph on Diaion HP20SS and lyophilisation of the relevant fractions gave the title product (0.32 g; 65%). (See U.K. Patent Application No. 2,107,307A.)

(c) Sodium 7β-[D-2-(3,4-dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate Sodium 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate (76 mg; 0.09 mmol) was dissolved in water (3 ml) and tetrahydrofuran (2 ml) at room temperature and the pH adjusted to 9.0 using sodium carbonate solution. Sodium sulphite (31 mg; 0.23 mmol) was added and the solution stirred at room temperature for 1 h whilst maintaining the pH at 9.0. The pH was adjusted to 6.5 using dilute hydrochloric acid and the solution partially evaporated. The residual solution was chromatographed on Diaion HP20SS and the relevant fractions lyophilised to give the title compound (51 mg; 75%).

(d) Sodium 7β-[D-2-(3,4-dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1β-oxide Sodium 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1β-oxide (50 mg; 0.06 mm) see Example 5(a) was dissolved in water (3 ml) and tetrahydrofuran (2 ml) at room temperature and the pH adjusted to 9.0 using sodium carbonate solution. Sodium sulphite (20 mg; 0.15 mmol) was added and the solution stirred at room temperature for 1.25 h whilst maintaining the pH at 9.0. The pH was adjusted to 6.5 with dilute hydrochloric acid, the solution evaporated to reduced volume and chromatographed on Diaion HP20SS. The relevant product fractions were lyophilised to give the title product (31 mg; 70%). λ$_{max}$. (H$_2$O) 270 nm, (εm 13237); ν$_{max}$. (KBr) 3400, 1784, 1710, 1676, 1611, 1040 cm$^{-1}$, δppm (D$_2$O) inter alia 1.16 (3H, t, J 7 Hz), 3.51 (2H, q, J 7 Hz), 3.5–3.8 (4H, m), 3.98 (3H, s) overlaps 3.9–4.1 (3H, m), 4.22 (1H, lower field arm of ABq, J 13 Hz; higher field arm obscured), 5.03 (1H, s), 5.32 (1H, s), 6.8–7.0 (3H, m), 8.14 (1H, s).

MIC against *P. mirabilis* 889 is 1.0 μg.ml$^{-1}$.

(e) Sodium 7β-[D-2-(3,4-dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1α-oxide Sodium 7β-[D-2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylate-1α-oxide (50 mg; 0.06 mmol) see Example 5(a) was converted to the title compound (25 mg; 56%) as described in Example 16d. λ$_{max}$.(H$_2$O) 269 nm (εm 13160); λhd max. (KBr) 3425, 1787, 1710, 1677, 1611, 1035 cm$^{-1}$; δppm (D$_2$O) inter alia 1.18 (3H, t, J 7 Hz), 3.52 (2H, q, J 7 Hz), 3.6–3.8 (3H, m), 4.00 (3H, s) overlaps 3.85–4.1 (3H, m), 4.08 and 4.29 (2H, ABq, J 13 Hz), 5.01 (1H, s), 5.38 (1H, s), 6.85–7.05 (3H, m), 8.22 (1H, s).

MIC against *P. mirabilis* 889 is 0.25 μg. ml$^{-1}$.

EXAMPLE 17

Sodium 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer A (a) Benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomers A and B.

The mixed sulphoxide isomers of benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide (see example 4) were carefully chromatographed on silica gel 60 eluting with ethyl acetate/dioxane 2:1. This enabled the isolation of pure samples of the less polar isomer A and more polar isomer B. The spectral data for isomer A were $v_{max}$ (CHCl$_3$) 3280, 2960, 2850, 1800, 1775, 1710, and 1690 cm$^{-1}$; δ(CDCl$_3$) 1.08 and 1.55 (6H, 2s, 2-CH$_3$'s), 1.18(3H, t, J 7 Hz, NCH$_3$CH$_3$), 2.26 (6H, s, OCOCH$_3$'s), 3.4–4.1(6H, m, NCH$_2$$\overline{CH}_2$NCH$_2$), 4.63(1H, s, 3-H), 5.15 and 5.29(2H, ABq, J 12 Hz, CH$_2$Ph), 5.18(1H, s, 5-H), 5.61(1H, d, J 8 Hz, NCHCO), 7.1–7.4(8H, m, phenyl), 8.03(1H, s, NH), 8.08 (1H, s, CHO), 8.48(1H, s, NH), 9.84(1H, d, J 8 Hz, NH).

(b) Sodium 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer A.

A solution of benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer A (0.008 g) in dry dioxane (3 ml) was treated with 10% palladium on charcoal catalyst (0.010 g) and hydrogenated at atmospheric pressure for 2.5 hour. The resulting mixture was filtered through celite and the filtrate concentrated under reduced pressure. The residue was partitioned between ethyl acetate and water and the pH adjusted to 6.5 with dilute aqueous sodium hydrogen carbonate. The aqueous layer was then separated and freeze dried to give sodium 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer A as a white powder (0.006 g); $v_{max}$ (KBr micro disc) 3430, 2927, 1778, 1710, 1677 and 1614 cm$^{-1}$; δ(D$_2$O) 1.26 and 1.57 (6H, 2s, 2-CH$_3$'s), 1.20 (3H, t, J 7 Hz, NCH$_2$CH$_3$), 2.37 (6H, s, OCOCH$_3$'s), 3.5–4.1(6H, m, NCH$_2$$\overline{CH}_2$NCH$_2$), 4.36(1H, s, 3-H), 5.29(1H, s, 5-H), 5.52(1H, s, NCHCO), 7.3–7.5(3H, m, phenyl), and 8.13(1H, s, CHO). MIC against *P. mirabilis* 889 is 4.0 μg.ml$^{-1}$.

EXAMPLE 18

Sodium 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer B (a) Benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer B.

Benzyl 6β-amino-6α-formamidopenicillanate-1-oxide, Isomer B (0.29 g) was stirred in dry dichloromethane (5 ml) at 0° C. under argon. To this was added N,N'-dicyclohexylcarbodiimide (0.16 g) followed by dropwise addition of D-2-[(4-ethyl-2,3-dioxopiperazin-1-yl)carbonylamino]-2-(3,4-diacetoxyphenyl)acetic acid (0.35 g) in dichloromethane over a period of 0.25 hour. The cooling was removed and the reaction mixture stirred at room temperature for 3 hour. The product was filtered and the filtrate concentrated and chromatographed on silica gel 60 eluting with ethyl acetate/ethanol 9:1 followed by further silica gel chromatography using chloroform/ethanol 9:1. This gave benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer B as a colourless foam (0.14 g); $v_{max}$ (CHCl$_3$), 3300, 2970, 1780, 1750 sh, 1710 sh, 1680, and 1045 cm$^{-1}$; δ(CDCl$_3$) 0.85 and 1.17(6H, 2s, 2-CH$_3$'s), 1.22(3H, t, J 7 Hz, NCH$_2$CH$_3$), 2.26(6H, s, OCOCH$_3$'s), 3.4–4.1(6H, m, NCH$_2$CH$_2$NCH$_2$), 4.45(1H, s, 3-H), 5.0–5.2(3H, m, 5-H and CH$_2$Ph), 5.61(1H, d, J 7 Hz, NCHCO), 7.1–7.4(8H, m, phenyls), 8.09(1H, s, CHO), 8.26 and 9.00(2H, 2 br s, NH's), and 10.11(1H, d, J 7 Hz, NH); (Found: $\overline{MH}^+$ 783 by +ve ion FAB. C$_{35}$H$_{38}$N$_6$O$_{13}$S requires M 782).

(b) Sodium 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer B.

A solution of benzyl 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer B (0.130 g) in dry dioxane (5 ml) was treated with 10% palladium on charcoal catalyst (0.130 g) and hydrogenated at atmospheric pressure for 2.5 hour. The reaction mixture was then filtered through Celite and the filtrate evaporated to ca 1 ml volume. It was treated with 1.93M sodium 2-ethylhexanoate in 4-methylpentan-2-one (0.085 ml) followed by dry diethyl ether (10 ml). The precipitate was collected, washed with 1:1 acetone/diethyl ether and dried under vacuum to give 6β-[D-2-[(4-ethyl-2,3-dioxopiperazin-1-yl)carbonylamino]-2-(3,4-diacetoxyphenyl)acetamido]-6α-formamidopenicillanate-1-oxide, Isomer B as a white powder (0.073 g); $v_{max}$(CHCl$_3$) 3436, 2966, 1776, 1710, 1678 and 1619 cm$^{-1}$; ε(D$_2$O) 1.01 and 1.28 (6H, 2s, 2-CH$_3$'s), 1.22(3H, t, J 7 Hz, NCH$_2$CH$_3$), 2.37(6H, s, OCOCH$_3$'s), 3.5–4.1(6H, m, NCH$_2$CH$_2$NCH$_2$), 4.28(1H, s, 3-H), 5.21(1H, s, 5-H), 5.54(1H, s, NCHCO), 7.3–7.6(3H, m, phenyl) and 8.19(1H, s, CHO). MIC against *P. mirabilis* 889 is 0.5 μg.ml$^{-1}$.

EXAMPLE 19

Sodium 6β-[D-2-[(4-ethyl-2,3-dioxoiperazin-1-yl)carbonylamino]-2-(3,4-diacetoxyphenyl)acetamido]-6α-formamidopenicillanate-1,1-dioxide (a) Benzyl 6β-[D-2-[(4-ethyl-2,3-dioxopiperazin-1-yl)carbonylamino]-2-(3,4-diacetoxyphenyl)acetamido]-6α-formamidopenicollanate-1,1-dioxide.

A solution of benzyl 6β-[D-2-[(4-ethyl-2,3-dioxopiperazin-1-yl)carbonylamino]-2-(3,4-diacetoxyphenyl)acetamido]-6α-formamidopenicillanate (0.500 g) in dry dichloromethane (10 ml) was stirred at room temperature under argon and treated with m-chloroperbenzoic acid (0.370 g) in a single portion. After a period of 2 hours the solution was washed with aqueous sodium hydrogen carbonate, then brine, and dried over sodium sulphate. The solution was concentrated and chromatographed on silica gel 60 eluting with ethyl acetate/dioxane 2:1 to give benzyl 6β-[D-2-[(4-ethyl-2,3-dioxopiperazin-1-yl)carbonylamino]-2-(3,4-diacetoxyphenyl)acetamido]-6α-formamidopenicillanate-1,1-dioxide as a colourless glass (0.130 g); $v_{max}$ (CHCl$_3$), 3280, 2960, 2910, 2860, 1805, 1760, 1715, 1690 and 1495 cm$^{-1}$; $\delta$(CDCl$_3$) 1.16(3H, t, J 7 Hz, NCH$_2$CH$_3$), 1.20 and 1.39(6H, 2s, 2-CH$_3$'s), 2.23 and 2.24(6H, 2s, OCOCH$_3$'s), 3.51(4H, br s, NCH$_2$'s), 3.99(2H, br s, NCH$_2$), 4.45(1H, s, 3-H), 5.02(1H, s, 5-H), 5.15 and 5.28(2H, ABq, J 12 Hz, PhCH$_2$), 5.65 (1H, d, J 6 Hz, NCHCO), 7.1–7.4(8H, m, phenyls), 8.00(1H, s, CHO), 8.10 and 8.47(2H, 2s, NH's) and 9.89(1H, d, J 6 Hz, NH).

(b) Sodium 6$\beta$-[D-2-[(4-ethyl-2,3-dioxopiperazin-1-yl)carbonylamino]-2-(3,4-diacetoxyphenyl)acetamido]-6$\alpha$-formamidopenicillanate-1,1-dioxide.

Benzyl 6$\beta$-[D-2-[(4-ethyl-2,3-dioxopiperazin-1-yl)carbonylamino]-2-(3,4-diacetoxyphenyl)acetamido]-6$\alpha$-formamidopenicillanate-1,1-dioxide (0.110 g) was dissolved in dry dioxane (10 ml) and 10% palladium on charcoal catalyst (0.110 g) was added. The mixture was hydrogenated at atmospheric pressure for 2 hour and then filtered through Celite. The filtrate was concentrated to about 1 ml volume and 1.93M. sodium 2-ethylhexanoate in 4-methylpentan-2-one (0.071 ml) was added. Precipitation of the white solid was completed by addition of diethyl ether. The solid was then separated, washed with 1:1 acetone/diethyl ether, neat diethyl ether, and dried under vacuum to yield sodium 6$\beta$-[D-2-[(4-ethyl-2,3-dioxopiperazin-1-yl)carbonylamino]-2-(3,4-diacetoxyphenyl)acetamido]-6$\alpha$-formamidopenicillanate-1,1-dioxide (0.088 g); $v_{max}$ (KBr) 3446, 2963, 2938, 1776, 1710, 1676, 1624 and 1502 cm$^{-1}$; $\delta$(D$_2$O) 1.12(3H, t, J 7 Hz, NCH$_3$CH$_3$), 1.40 and 1.45(6H, 2s, 2-CH$_3$'s), 2.36(6H, s, COCH$_3$'s), 3.53 (2H, q, J 7 Hz, NCH$_2$CH$_3$), 3.6–4.1(4H, m, NCH$_2$CH$_2$N), 4.27(1H, s, 3-H), 5.28(1H, s, 5-H), 5.53(1H, s, NCHCO), 7.32(1H, d, J 8 Hz, aromatic 5-H), 7.38(1H, d, J 2 Hz, aromatic 2-H), 7.47(1H, dd, J 8 and 2 Hz, aromatic 6-H), and 8.14(1H, s, CHO).

EXAMPLE 20

Pivaloyloxymethyl 6$\beta$-[D-2-(3,4-diacetoxyphenyl)-2-[(4-ethyl-2,3-dioxopiperazin-1-yl)carbonylamino]acetamido]-6$\alpha$-formamidopenicillanate-1-oxide (i) Pivaloyloxymethyl 6$\beta$-[D-2-(3,4-diacetoxyphenyl)-2-[(4-ethyl-2,3-dioxopiperazin-1-yl)carbonylamino]acetamido]-6$\alpha$-formamidopenicillanate.

Sodium 6$\beta$-[D-2-(3,4-diacetoxyphenyl)-2-[(4-ethyl-2,3-dioxopiperazin-1-yl)carbonylamino]acetamido]-6$\alpha$-formamidopenicillanate (0.698 g, 1 mmol) in N,N-dimethylformamide was treated with freshly distilled bromomethyl pivalate (0.195 g, 1 mmol) and stirred for 12 hour. The reaction mixture was evaporated to dryness and the residue was dissolved in a 50:50 ethyl acetate:water mixture. The two phases were separated and the ethyl acetate layer was washed with dilute sodium hydrogen carbonate, water and brine before being dried over magnesium sulphate and evaporated to dryness to give the crude product as a white foam (0.317 g). This was chromatographed on silica gel 60 (<230 mesh ASTM) (15 g) eluting with 5% ethanol in ethyl acetate to give the title compound as a white foam (0.091 g, 15%); $v_{max}$ (CH$_2$Cl$_2$) 3275, 1775, 1765, 1710, 1690, 1500 cm$^{-1}$; $\delta$(CDCl$_3$) 0.90(3H, s, 2-CH$_3$), 1.10–1.38(15H, m, CH$_2$CH$_3$, 2-CH$_3$, C(CH$_3$)$_3$), 2.27 (6H, s, OCOCH$_3$'s), 3.40–3.68(3H, m, CH$_2$CH$_3$, piperazine CH), 3.72–4.02(2H, m, piperazine CH$_2$), 4.48(1H, s, 3-H), 5.52(1H, s, 5-H), 5.60(1H, d, J 8 Hz, ArCH, s with D$_2$O), 5.73, 5.80(2H, ABq, J 6 Hz, CH$_2$OCO), 7.12(1H, d, J 8 Hz, aromatic 5-H), 7.30(1H, d, J 2 Hz, aromatic 2-H), 7.44(1H, dd, J 8 and 2 Hz, aromatic 6-H), 8.05(1H, s, NH, exch with D$_2$O), 8.09(1H, s, NHCHO), 8.69(1H, s, NH exch. with D$_2$O), 10.12(1H, d, J 8 Hz, NH, exch with D$_2$O).

(ii) Pivaloyloxymethyl 6$\beta$-[D-2-(3,4-diacetoxyphenyl)-2-[(4-ethyl-2,3-dioxopiperazin-1-yl)carbonylamino]acetamido]-6$\alpha$-formamidopenicillanate-1-oxide.

Pivaloxymethyl 6$\beta$-[D-2-(3,4-diacetoxyphenyl)-2-[(4-ethyl-2,3-dioxopiperazin-1-yl)carbonylamino]acetamido]-6$\alpha$-formamidopenicillanate (0.032 g, 0.04 mmol) in dichloromethane (5 ml) was cooled to 0° C. and treated dropwise with m-chloroperoxybenzoic acid (0.008 g, 0.044 mmol) in dichloromethane (3 ml). The reacton mixture was stirred for 0.5 hour before being evaporated to dryness. The residue was taken up in ethyl acetate and washed with dilute hydrochloric acid, dilute sodium hydrogen carbonate and brine before being dried over magnesium sulphate and evaporated to dryness to give the crude product as a white foam (0.030 g). This was chromatographed on silica gel 60 (<230 mesh ASTM) (5 g) eluting with 5% ethanol in chloroform to give sulphoxide isomer A of the title compound (0.005 g, 15% yield) and sulphoxide isomer B of the title compound (0.005 g, 15% yield), both as white foams. Spectral data for isomer A were $v_{max}$ (CHCl$_3$), 3286, 2965, 1795 (sh), 1770, 1712, 1687, 1501, 1369, 1261, 1109, 1014, 809 cm$^{-1}$; $\delta$(CDCl$_3$) 1.23(15H, m, C(CH$_3$)$_2$, CH$_2$CH$_3$, 2-CH$_3$), 1.60(3H, s, 2-CH$_3$), 2.29(6H, s, OCOCH$_3$'s), 3.35–3.66(4H, m, CH$_2$CH$_3$, piperazine CH$_2$), 3.91–4.15(2H, m, piperazine CH$_2$), 4.65 (1H, s, 3-H), 5.19(1H, s, 5-H), 5.60(1H, d, J 7 Hz, ArCH), 5.72, 5.95(2H, ABq, J 6 Hz, CH$_2$OCO), 7.10–7.45 (3H, m, aromatic-H's), 7.92–8.15 (2H, m, NHCHO and NH), 8.50 (1H, br s, NH) and 9.85 (1H, d, J 7 Hz, NH) and for isomer B were $v_{max}$ (CHCl$_3$) 3271, 2931, 1769, 1713, 1693, 1500, 1369, 1258, 1183, 1114 cm$^{-1}$; $\delta$(CDCl$_3$) 0.88(3H, s, 2-CH$_3$), 1.05–1.43(15H, m, C(CH$_3$)$_3$, CH$_2$CH$_3$, 2-CH$_3$), 2.27 (6H, m, OCOCH$_3$'s), 3.40–3.75 (4H, m, CH$_2$CH$_3$, piperazine CH$_2$), 3.82–4.17 (2H, m, piperazine CH$_2$), 4.46(1H, s, 3-H), 5.15(1H, s, 5-H), 5.58(1H, d, J 6Hz, ArCH), 5.70, 5.79(2H, ABq, J 6 Hz, CH$_2$oco, 7.05–7.41(3H, m, aromatic-H's), 8.16(1H, s, NHCHO), 8.40(1H, s, NH), 9.45(1H, brs, NH), 10.03(1H, d, J 6 Hz, NHCH).

EXAMPLE 21

Sodium 6$\beta$-(phenoxyacetamido)-6$\alpha$-formamido penicilllanate-1-oxide (i) Benzyl 6$\beta$-(phenoxyacetamido)-6$\alpha$-formamidopenicillanate-1-oxide (Isomers A and B).

A solution of benzyl 6$\beta$-(phenoxyacetamido)-6$\alpha$-formamidopenicillanate (0.314 g, 0.65 mmol) in dichloromethane (10 ml) was stirred at 0° C. with m-chloroperbenzoic acid (0.125 g, 0.72 mmol) for 2 hour. The solution was then evaporated to dryness and the solid dissolved in ethyl acetate (20 ml), washed with dilute aqueous sodium hydrogen carbonate (twice), brine, and dried over magnesium sulphate. The solution was concentrated and chromatographed at atmostpheric pressure on silica gel (30 g), eluting with 3% methanol in chloroform, to obtain pure samples of both the less polar isomer (isomer A) and more polar isomer (isomer B) of benzyl 6$\beta$-(phenoxyacetamido)-6$\alpha$-formamidopenicillanate-1-oxide. The data for isomer A(0.107 g) were $R_f$ 0.31 in 5% methanol in chloroform; $\nu_{max}$(KBr) 1794, 1750, 1685, 1598, 1493 and 1060 cm$^{-1}$; $\delta$(CDCl$_3$) 1.09 and 1.61(6H, 2s, C(CH$_3$)$_2$), 4.51 (2H, ABq, J14 Hz, PhOCH$_2$CO—), 4.70(1H, s, 3-H), 5.16(1H, s, 5-H) 5.27(2H, ABq, J11 Hz, PhCH$_2$), 6.85–7.45(10H, m, phenyl), 8.23 (1H, s, NHCHO), 8.35(1H, s, D$_2$Oexch., NHCHO). The data for isomer B (0.088 g) were $R_f$ 0.23 in 5% methanol in chloroform; $\nu_{max}$(KBr) 1796, 1748, 1685, 1598, 1492 and 1061 cm$^{-1}$; $\delta$(CDCl$_3$) 1.23 and 1.47(6H, 2s, C(CH$_3$)$_2$), 4.51(2H, s, PhOCH$_2$CO—), 4.55(1H, s, 3-H), 5.10 (1H, s, 5-H), 5.22(2H, ABq, J11 Hz, PhCH$_2$), 6.80–7.45(10H, m, phenyls), 8.17(1H, s, NHCHO), 8.21(1H, s, D$_2$Oexch., NHCHO).

(ii) Sodium 6$\beta$-(phenoxyacetamido)-6$\alpha$-formamido penicillanate-1-oxide (isomer B).

The more polar isomer (isomer B, 0.088 g) of benzyl 6$\beta$-(phenoxyacetamido)-6$\alpha$-formamidopenicillanate-1-oxide was dissolved in tetrahydrofuran (5 ml) and hydrogenated in the presence of 10% palladium on charcoal (0.04 g) under ambient conditions for 3 hour. The mixture was then filtered through Kieselguhr, and the insoluble material washed with tetrahydrofuran. The filtrate was then evaporated to dryness and the solid immediately redissolved in acetone (1 ml). This was treated with 1.93M sodium 2-ethylhexanoate in 4-methylpentan-2-one (0.09 ml, 0.17 mmol) followed by diethyl ether (5 ml) to complete precipitation. The solid sodium 6$\beta$-(phenoxyacetamido)-6$\alpha$-formamidopenicillanate-1-oxide was filtered off, washed with ether and dried (0.027 g, 36%); $R_f$ 0.30 in butanol:acetic acid:water (4:1:1); $\nu_{max}$(KBr) 1783, 1684, 1617, 1559, and 1492 cm$^{-1}$; $\delta$(D$_2$O) 1.32 and 1.47(6H, 2s, C(CH$_3$)$_2$), 4.32(1H, s, 3-H), 5.14(1H, s, 5-H), 7.00–7.55(5H, m, phenyl), and 8.18 (1H, s, NHCHO).

EXAMPLE 22

Sodium 6$\beta$-[D-2-[(4-ethyl-2,3-dioxopiperazin-1-yl)carbonylamino]-2-phenylacetamido]-6$\alpha$-formamidopenicillanate-1-oxide (i) Benzyl 6$\beta$-[D-2-[(4-ethyl-2,3-dioxopiperazin-1-yl)carbonylamino]-2-phenylacetamido]-6$\alpha$-formamidopenicillanate-1-oxide. (Isomers A and B).

A solution of benzyl 6$\beta$-[D-2-[(4-ethyl-2,3-dioxopiperazin-1-yl)carbonylamino]-2-phenylacetamido]-6$\alpha$-formamidopenicillanate (0.12 g, 0.185 mmol) in dichloromethane (10 ml) was stirred at 0° C. and treated with m-chloroperbenzoic acid (0.035 g, 0.2 mmol). After 1 hour the mixture was diluted with ethyl acetate (30 ml), washed with dilute aqueous sodium hydrogen carbonate, brine, and dried over magnesium sulphate. The solution was chromatographed on silica gel (4 g) eluting with 5% ethanol in ethyl acetate grading to 7.5% ethanol in ethyl acetate, to separate the less polar isomer (isomer A, 0.017 g) from the more polar isomer (isomer B, 0.036 g) of benzyl 6$\beta$-[D-2-[(4-ethyl-2,3-dioxopierazin-1-yl)carbonyl-amino]-2-phenylacetamido]-6$\alpha$-formamidopenicillanate-1-oxide. The data for isomer A were $R_f$ 0.22 in 10% ethanol in ethyl acetate; $\nu_{max}$ (CH$_2$Cl$_2$) 1795, 1710, and 1690 cm$^{-1}$; $\delta$(CDCl$_3$) 1.05–1.35 (6H, m, 2-CH$_3$ and CH$_2$CH$_3$), 1.59(3H, s, 2-CH$_3$), 3.40–3.60(4H, m, CH$_2$CH$_3$, N-CH$_2$), 3.95–4.15 (2H, m, N-CH$_2$), 4.65(1H, s, 3-H), 5.10–5.35(3H, m, Ph-CH$_2$ and 5-H), 5.53 (1H, d, J 8 Hz, $\alpha$-CH), 7.20–7.50(11H, m, phenyl and 6$\beta$-NH), 8.08 (1H, s, NHCHO), 8.13(1H, s, exch in D$_2$O, NHCHO), 9.80(1H, d, J 8 Hz, $\alpha$-NH); and for isomer B were $R_f$ 0.15 in 10% ethanol in ethyl acetate; $\nu_{max}$(CH$_2$Cl$_2$) 1795, 1750, 1710 and 1680 cm$^{-1}$; $\delta$ (CDCl$_3$) 0.73(3H, s, 2-CH$_3$), 1.10–1.35(6H, m, 2-CH$_3$ and NCH$_2$CH$_3$), 3.40–3.70 (4H, m, NCH$_2$'s), 3.90–4.10(2H, m, N-CH$_2$), 4.43(1H, s, 3-H), 5.05–5.25(3H, m, Ph-CH$_2$ and 5-H), 5.57(1H, d, J7Hz, $\alpha$-CH), 7.20–7.50(11H, m, phenyl and 6$\beta$-NH), 8.21(2H, s, NHCHO), 10.05(1H, d, J 7 Hz, $\alpha$NH).

(ii) Sodium 6$\beta$-[D-2-[(4-ethyl-2,3-dioxopiperazin-1-yl)carbonylamino]-2-phenylacetamido]-6$\alpha$-formamidopenicillanate-1-oxide. (Isomers A and B).

The more polar isomer B (0.032 g) of benzyl 6$\beta$-[D-2-[(4-ethyl-2,3-dioxopiperazin-1-yl)carbonylamino]-2-phenylacetamido]-6$\alpha$-formamidopenicillanate-1-oxide was dissolved in tetrahydrofuran (5 ml) and hydrogenated for 1.5 hour under ambient conditions in the presence of 10% palladium on charcoal catalyst (0.04 g). The mixture was then filtered through Kieselguhr, and the insoluble material washed with tetrahydrofuran. The filtrate was evaporated and the solid was taken up in water which was adjusted to pH 6.5 with dilute aqueous sodium hydrogen carbonate. The solution was washed with ethyl acetate (2x), filtered through dicalite and freeze dried to give sodium 6$\beta$-[D-2-[(4-ethyl-2,3-dioxopiperazin-1-yl)carbonylamino]-2-phenylacetamido]-6$\alpha$-formamidopenicillanate-1-oxide (isomer B) (0.012 g, 42%); $R_f$ 0.35 in butanol:acetic acid:water (4:1:1); $\nu_{max}$ (KBr) 1782, 1710, 1677, 1616, 1511, and 1460 cm$^{-1}$; $\delta$(D$_2$O) 0.99(3H, s, 2-CH$_3$), 1.10–1.30 (6H, m, 2-CH$_3$ and CH$_2$CH$_3$), 3.51(2H, q, J 7 Hz), 3.60–3.80(2H, m, N-CH$_2$), 3.90–4.15(2H, m, N-CH$_2$), 4.20(1H, s, 3-H), 5.14(1H, s, 5-H), 5.47(1H, s, $\alpha$-CH), 8.16(1H, s, NHCHO). MIC against P. mirabilis 889 is 1 $\mu$g/ml. The less polar isomer (isomer A, 0.017 g) of benzyl 6$\beta$-[D-2-[(4-ethyl-2,3-dioxopiperazin-1-yl)carbonylamino]-2-phenylacetamido]-6$\alpha$-formamidopenicillanate-1-oxide was similarly hydrogenated and freeze-dried to yield sodium 6$\beta$-[D-2-[(4-ethyl-2,3-dioxopiperazin-1-yl)carbonylamino]-2-phenylacetamido]-6$\alpha$-formamidopenicillanate-1-oxide (isomer A, 0.003 g, 10%); $\nu_{max}$ (KBr) 1782, 1712, 1677, 1619, 1521 and 1461 cm$^{-1}$; $\delta$(D$_2$O) 1.15–1.35(6H, m, 2-CH$_3$ and CH$_2$CH$_3$), 1.57(3H, s, 2-CH$_3$), 3.53 (2H, q, J 7 Hz, NCH$_2$CH$_3$), 3.60–3.80(2H, m, N-CH$_2$), 3.90–4.15(2H, m, N-CH$_2$), 4.37(1H, s, 3-H), 5.29(1H, s, 5-H), 5.48(1H, s, $\alpha$-CH), 8.13(1H, s, NHCHO).

EXAMPLE 23

6$\beta$-(D-2-Amino-2-phenylacetamido)-6$\alpha$-formamidopenicillanic acid-1-oxide.

(i) Benzyl 6$\beta$-[D-2-[(4-nitrobenzyl)oxycarbonylamino)-2-phenylacetamido]-6$\alpha$-formamidopenicillanate-1-oxide, Isomer B.

A solution of benzyl 6$\beta$-[D-2-[(4-nitrobenzyl)oxycarbonylamino]-2-phenylacetamido]-6$\alpha$-formamidopenicillanate (0.331 g, 0.5 mmol) in dichloromethane (10 ml) was stirred at 0° C. and treated with m-chloroperbenzoic acid (0.095 g, 0.55 mmol). After 1.5 hour the mixture was diluted with ethyl acetate (30 ml), washed with dilute aqueous sodium hydrogen carbonate (2x), brine, and dried over magnesium sulphate. The solution was then concentrated and chromatographed on silica gel (9 g) eluting with 2% methanol in chloroform. This allowed the separation of the more polar isomer (isomer B) of benzyl 6$\beta$-[D-2-[(4-nitrobenzyl)oxycarbonylamino]-2-phenylacetamido]-6$\alpha$-formamidopenicillanate-1-oxide (0.173 g, 51%); $R_f$ 0.54 in 10% methanol in chloroform; $\nu_{max}$(KBr) 1794, 1730 sh, 1685, 1607 and 1517 cm$^{-1}$; δ[(CD$_3$)$_2$CO] 0.90 and 1.13(6H, 2s, C(CH$_3$)$_2$), 4.57(1H, s, 3-H), 5.02(1H, s, 5-H), 5.15-5.35(4H, m, OCH$_2$Ph's), 5.55(1H, d, J 8 Hz α-CH), 7.30-7.60(11H, m, phenyls and 6β-NH), 7.67 and 8.24(4H, 2d, J 8 Hz, 4-nitrophenyl system), 8.22(1H, s, NHCHO), 8.48(1H, s, exch. in D$_2$O, NHCHO), 8.99(1H, s, exch. in D$_2$O, α-NH).

(ii) 6β-(D-2-Amino-2-phenylacetamido)-6α-formamidopenicillanic acid-1-oxide, isomer B.

The mole polar isomer (isomer B, 0.173 g, 0.256 mmol) of benzyl 6β-[D-2-[(4-nitrobenzyl)oxycarbonylamino]-2-phenylacetamido]-6α-formamidopenicillanate-1-oxide was dissolved in tetrahydrofuran (8 ml) and water (2 ml) and hydrogenated in the presence of 10% palladium on charcoal (0.17 g) under ambient conditions for 2.5 hour. The mixture was then filtered through Kieselguhr, and the insoluble material washed with tetrahydrofuran and water. The filtrate was then concentrated to about 20 ml to remove any tetrahydrofuran, washed with ethyl acetate (2x) concentrated further to a volume of 10 ml, filtered and freeze dried to give 6β-[D-2-amino-2-phenylacetamido]-6α-formamidopenicillanic acid-1-oxide, isomer B (0.063 g, 60%); R$_f$ 0.19 in n-butanol:acetic acid:water, 4:1:1; ν$_{max}$(KBr) 1786, 1690, 1616, 1516 cm$^{-1}$; δ(D$_2$O) 1.02 and 1.25 (6H, 2s, C(CH$_3$)$_2$), 4.23(1H, s, 3-H), 5.14(1H, s, 5-H), 5.20(1H, s, NCHCO], 7.54(5H, br s, ArH), 8.16(1H, s, NHCHO). MIC against P. mirabilis 889 is 32 μg/ml.

EXAMPLE 24

Sodium 6β-[D-2-(4-hydroxyphenyl)-2-[[3-(methylsulphonyl)-2-oxoimidazolidin-1-yl]carbonylamino]acetamido]-6α-formamidopenicillanate-1-oxide (i) Benzyl 6β-[D-2-[(2,2,2-trichloroethoxy)carbonylamino]-2-[4-(benzyloxycarbonyloxy)phenyl]acetamido]-6α-formamidopenicillanate-1-oxide. (isomer B).

A solution of benzyl 6β-[D-2-[(2,2,2-trichloroethoxy)carbonylamino]-2-[4-(benzyloxycarbonyloxy)phenyl]acetamido]-6α-formamidopenicillanate (4.5 g, 5.5 mmol) in dichloromethane (40 ml) was stirred at 0° C. and treated with m-chloroperbenzoic acid (0.95 g, 5.5 mmol). After 2 hour the mixture was diluted with ethyl acetate (120 ml) and washed with dilute aqueous sodium hydrogen carbonate (2x), brine, and dried over magnesium sulphate. The solution was then concentrated and chromatographed on silica gel (125 g) eluting with 4% methanol in chloroform, combining appropriate fractions to obtain a pure sample of the more polar isomer (isomer B) of benzyl 6β-[D-2-[(2,2,2-trichloroethoxy)-carbonylamino]-2-[4-(benzyloxycarbonyloxy)phenyl]acetamido]-6α-formamidopenicillanate-1-oxide (0.170 g, 37%); R$_f$ 0.35 in 5% methanol in chloroform; ν$_{max}$ (KBr) 1794, 1748, 1690, 1504, and 1453 cm$^{-1}$; δ(CDCl$_3$) 0.89 and 1.18(6H, 2s, C(CH$_3$)$_2$), 4.43(1H, s, 3-H), 4.27 and 4.35(2H, ABq, J 12 Hz, CH$_2$CCl$_3$), 5.1-5.3(5H, m, benzyl CH$_2$'s and 5-H), 5.70(1H, d, J 7 Hz, α-CH), 7.12 and 7.51 (4H, 2d, J 9 Hz, phenyl), 7.2-7.5 (11 Hz, m, phenyl and 6β-NH), 8.10(1H, s, NHCHO), 8.30(1H, s, D$_2$Oexch., NHCHO), 8.95(1H, s, D$_2$O exch., α-NH).

(ii) Benzyl 6β-[D-2-amino-2-[4-(benzyloxycarbonyloxy)phenyl]acetamido]-6α-formamidopenicillanate-1-oxide (Isomer B).

The preceding compound, the N-(2,2,2-trichloroethoxy)carbonyl derivative (0.6 g, 0.73 mmol), was dissolved in tetrahydrofuran (15 ml) and stirred vigorously. It was treated with M. potassium dihydrogen phosphate (3 ml) followed by freshly acid-washed zinc powder (1.2 g). The pH was maintained at 4–5 by addition of dilute aqueous hydrochloric acid. The mixture was stirred for a total of 3 hour, with the addition of a further 1.2 g of freshly acid-washed zinc after 1 hour, and then filtered through Kieselguhr, washed with tetrahydrofuran, water and ethyl acetate. The filtrate was thus partitioned between organic and aqueous phases. The organic phase was washed with brine (2×), dried over magnesium sulphate and evaporated to dryness. The solid was immediately redissolved in dichloromethane (10 ml), stored overnight at −78° C. and used without further purification. It had a R$_f$ 0.16 in 10% methanol in chloroform.

(iii) Benzyl 6β-[D-2-[4-(benzyloxycarbonyloxy)-phenyl]-2-[[3-(methylsulphonyl)-2-oxoimidazolidin-1-yl]carbonylamino]acetamido]-6α-formamido penicillanate-1-oxide (isomer B).

The product of the preceding reaction was stirred at 0° C. and treated with triethylamine (0.15 ml, 1.1 mmol) and 3-(methylsulphonyl)-2-oxoimidazolidine-1-carbonyl chloride (0.165 g, 0.73 mmol) in dichloromethane (3 ml). After 2 hour the mixture was diluted with ethyl acetate (30 ml) and washed with 0.5M hydrochloric acid, dilute aqueous sodium hydrogen carbonate, brine and dried over magnesium sulphate. The solution was concentrated and chromatographed on silica gel (11 g) eluting with 2% methanol in chloroform, combining appropriate fractions to obtain benzyl 6β-[D-2-[4-(benzyloxycarbonyloxy)phenyl]-2-[[3-(methylsulphonyl)-2-oxoimidazolidin-1-yl]carbonylamino]acetamido]-6α-formamido penicillanate-1-oxide (isomer B) (0.093 g, 15%); R$_f$ 0.44 in 10% methanol in chloroform; ν$_{max}$ (KBr) 1795, 1760 sh, 1733, 1684, 1506, and 1478 cm$^{-1}$; δ(CDCl$_3$) 0.80 and 1.13(6H, 2s, C(CH$_3$)$_2$), 3.41(3H, s, SO$_2$CH$_3$), 3.65-4.15(4H, m, NCH$_2$CH$_2$N), 4.44(1H, s, 3-H), 5.05-5.30(5H, m, benzyl CH$_2$'s and 5-H), 5.51(1H, d, J 7 Hz, α-CH), 7.13 and 7.49 (4H, 2d, J 8 Hz, phenyl), 7.2-7.6(10H, m, phenyls), 8.25 and 8.43 (2H, 2s, D$_2$O-exch., NH's), 8.29(1H, s, NHCHO), 9.11(1H, d, J 7 Hz, D$_2$Oexch, α-NH).

(iv) Sodium 6β-[D-2-(4-hydroxyphenyl)-2-[[3-(methylsulphonyl)-2-oxoimidazolidin-1-yl]carbonylamino]acetamido]-6α-formamidopenicillanate-1-oxide (isomer B)

Benzyl 6β-[D-2-[4-(benzyloxycarbonyloxy)phenyl]-2-[[3-(methylsulphonyl)-2-oxoimidazolidin-1-yl]carbonylamino]acetamido]-6α-formamidopenicillanate-1-oxide (0.085 g, 0.1 mmol) was dissolved in tetrahydrofuran (10 ml) and hydrogenated in the presence of 10% palladium on charcoal (0.085 g) under ambient conditions for a total of 3 hour. After 1.5 hour a further 0.045 g of 10% palladium on charcoal was added. The mixture was then filtered through Kieselguhr, washed on the filter with tetrahydrofuran, and then evaporated to produce a white solid which was immediately redissolved in acetone (1 ml). This solution was treated with 1 ml of a solution of 0.51 ml of 1.93M sodium 2-ethylhexanoate in 4-methylpentan-2-one in acetone (10 ml), followed by ether (10 ml) to precipitate the title sodium salt (0.011 g). A further quantity of less pure material (0.002 g) was obtained by evaporation of the mother liquor to dryness followed by trituration with fresh ether (21% in all); R$_f$ 0.32 in n-butanol:acetic acid:water, 4:1:1; ν$_{max}$ (KBr) 1781, 1729, 1676, 1615, 1543, and 1510 cm$^{-1}$; δ(D$_2$O) 1.02 and 1.23(6H, 2s, (CH$_3$)$_2$C), 3.40(3H, s, SO$_2$CH$_3$), 3.8–4.0(4H, m, NCH$_2$'s), 4.21(1H, s, 3-H), 5.14(1H, s, 5-H), 5.32 (1H, s, NCHCO), 6.83(2H, d, ArH) 7.31(2H, d, ArH), 8.16(1H, s, NHCHO). MIC against *P. mirabilis* 889 is 2.0 μg/ml.

EXAMPLE 25

Sodium 6α-formamidopenicillanate-1-oxide (i) Benzyl 6α-formamidopenicillanate

A solution of benzyl 6β-[(4-nitrobenzylidene)amino]-penicillanate (2.20 g) in dry dimethylformamide (30 ml) was stirred at −18° C. under argon and treated with diisopropylethylamine (2.00 ml). After 18 minutes the reaction mixture was diluted with benzene (250 ml) and washed six times with water, including pH 2 phosphate on wash 2 and sodium hydrogen carbonate on wash 5. The solution was then dried over sodium sulphate and concentrated to an orange foam. 2,4-Dinitrophenylhydrazine (0.99 g) and toluene-p-sulphonic acid (0.98 g) were stirred together in ethanol (80 ml) at room temperature for 0.75 hour, and a solution of the orange foam in chloroform (10 ml) added. After a further period of 0.75 hour the product was filtered and the solid washed with ethanol. The combined filtrates was concentrated and the residue washed with diethyl ether. The insoluble material was then shaken with a mixture of water (5 ml), ethyl acetate (50 ml), and sodium hydrogen carbonate (0.42 g). The organic layer was separated, washed with brine, dried over magnesium sulphate and concentrated. Chromatography on silica gel 60 eluting with ethyl acetate/hexane 7:3 gave benzyl 6α-aminopenicillanate as a gum. This was disolved in dichloromethane (20 ml) and stirred at 0° C. under argon. It was treated with pyridine (1.64 ml) and acetic formic anhydride (0.82 ml) and the reaction allowed to warm to room temperature over a period of 3 hour. It was then washed with 0.5M hydrochloric acid, dilute aqueous sodium hydrogen carbonate, brine and dried over sodium sulphate. It was chromatographed on silica gel 60 eluting with ethyl acetate/hexane 1:1 to give benzyl 6α-formamidopenicillanate (0.43 g); $v_{max}$ (CHCl$_3$) 3420, 3320 br, 1780, 1740 and 1690 cm$^{-1}$; δ(C$_6$D$_6$) 1.10 and 1.16(6H, 2s, 2-CH$_3$'s), 4.43 (1H, s, 3-H), 4.84(2H, s, PhCH$_2$), 5.00(1H, s, 5-H), 5.1–5.4(2H, m, 6-H and NH), 7.08(5H, s, phenyl), and 7.60(1H, s, CHO)

(ii) Benzyl 6α-formamidopenicillanate-1-oxide.

A solution of benzyl 6α-formamidopenicillanate (0.216 g) in dichloromethane (5 ml) was cooled to 0° C. and treated with m-chloroperbenzoic acid (0.123 g). After a period of 1 hour, the solution was diluted with ethyl acetate, washed with dilute aqueous sodium hydrogen carbonate, then brine, and dried over sodium sulphate. It was chromatographed on silica gel 60 eluting with ethyl acetate to give benzyl 6α-formamidopenicillanate-1-oxide (0.064 g); $v_{max}$ (CHCl$_3$) 3420, 3300 br, 1795, 1740, and 1690 cm$^{-1}$; δ(CDCl$_3$) 1.07 and 1.59 (6H, 2s, 2-CH$_3$'s), 4.50(1H, s, 3-H), 5.11 and 5.32(2H, ABq, J 12 Hz, PhCH$_2$), 5.0–5.4(2H, m, 5-H and 6-H), 7.34(6H, s, NH and phenyl), and 8.22(1H, s, CHO). (Found: M$^+$, 332.0834. C$_{16}$H$_{16}$N$_2$O$_4$S requires M, 332.0831).

(iii) Sodium 6α-formamidopenicillanate-1-oxide

Benzyl 6α-formamidopenicillanate-1-oxide (0.056 g) was dissolved in dry tetrahydrofuran (5 ml) and hydrogenated at atmospheric pressure over 10% palladium on charcoal catalyst (4×0.050 g). The catalyst was changed every 3 hour and the reaction was run for 12 hour. The product was filtered through Celite and concentrated to about 0.5 ml volume. It was treated with 1.93M sodium 2-ethylhexanoate in 4-methylpentan-2-one (0.10 ml), followed by diethyl ether to complete precipitation. The solid was separated, washed with 1:1 diethyl ether/acetone, followed by diethyl ether, and dried in vacuo to give sodium 6α-formamidopenicillanate-1-oxide as a white powder (0.031 g); $v_{max}$(KBr) 3417 br, 1783, 1675, 1615, and 1514 cm$^{-1}$; δ(D$_2$O) 1.32 and 1.67(6H, 2s, 2-CH$_3$'s), 4.28 (1H, s, 3-H), 5.07 and 5.43(2H, 2d, J 1 Hz, 5-H and 6-H), and 8.24(1H, s, CHO).

EXAMPLE 26

Sodium 3-Carbamoyloxymethyl-7α-formamido-7β-thien-2-yl-acetamido-ceph-3-em-4-carboxylate-1-oxide (a) 7α-Formamido-3-hydroxymethyl-7β-thien-2-ylacetamido-ceph-3-em-4-carboxylic acid Sodium 7α-Formamido-7β-thien-2-ylacetamido-cephalosporanate (1.00 g) (see UK Patent Application GB 2107307A) was dissolved in 0.05 m potassium dihydrogen phosphate (40 ml) and treated with citrus acetyl esterase preparation (ex. Sigma chemicals) (10 ml, equivalent to approx. 40 mg enzyme protein). The pH was adjusted to 7.0 by the addition of 2M sodium hydroxide. The mixture was stirred slowly at ambient temperature, maintaining a pH of 7.0+0.2 by the addition of dilute sodium hydroxide. The reaction was monitored by t.l.c. when all the starting material had been consumed (approx. 2 h). The mixture was saturated with sodium chloride and cooled (ice bath). The solution was layered with an equal volume of ethyl acetate and with vigorous stirring acidified to pH 1.5 with 5M hydrochloric acid. The organic phase was separated and the aqueous phase re-extracted with ethyl acetate. The combined extracts were washed with brine, then dried (MgSO$_4$), filtered. On concentrating the concentrate was stored at 4° C. for 1 h. The solid was filtered off under dry argon, washing with a small volume of ice-cooled ethyl acetate. The solid was dried in vacuo over P$_2$O$_5$, giving the title compound (254 mg).

$v_{max}$ (KBr) 3307, 2999, 1778, 1671 and 1516 cm$^{-1}$. δppm (250 MHz) (CD$_3$.CO.CD$_3$) (major rotamer) 3.43 and 3.63 (together 2H, ABq, J 16 Hz), 3.93 (2H, s), 4.47 (2H, AA'), 5.22 (1H, s), 6.9 to 7.1 (2H, m), 7.25 to 7.40 (1H, m), 8.20 (1H, s), 8.31 (1H, broad s, exch. D$_2$O), 8.45 (1H, broad s, exch. D$_2$O).

(b) Sodium 3-carbamoyloxymethyl-7α-formamido-7β-thien-2-yletamido-ceph-3-em-4-carboxylate 7α-Formamido-3-hydroxymethyl-7β-thien-2-ylacetamido-ceph-3-em-4-carboxylic acid (80 mg) was suspended in dry acetonitrile (3 ml) and cooled to 0° C. with stirring under dry argon. Chlorosulphonyl isocyanate (0.044 ml) was added dropwise from a syringe; stirring was continued at 0° C. for 1 h. The solution was evaporated to dryness at reduced pressure to give a gum. The gum was dissolved in water by adding saturated sodium bicarbonate solution to give a solution of pH 1.5. The resulting solution was layered with an equal volume of ethyl acetate and stirred at ambient temperature overnight. The ethyl acetate layer was separated and the aqueous re-extracted with ethyl acetate. The combined extracts were washed with brine, then dried (MgSO$_4$), filtered and the filtrate evaporated at reduced pressure. The crude product was dissolved in dilute sodium bicarbonate solution at pH 6.5 and the resulting solution chromatographed on 'Diaion' HP20SS resin, eluting with water then acetone/water mixtures. The product containing fractions were combined, concentrated at reduced pressure and the concentrate freeze dried to give the title compound (3 mg). $\nu_{max}$ (KBr) 3440, 3380, 1767, 1676, 1611, and 1525 cm$^{-1}$; δppm (250 MHz) (D$_2$O) (major rotamer) 3.25 and 3.60 (together 2H, ABq, J 18 Hz), 3.94 (2H, s), 4.61 (1H, upper field ½ ABq, lower field signal obscured by HOD, J 12 Hz), 5.31 (1H, s), 7.0 to 7.1 (2H, m), 7.3 to 7.4 (1H, m), 8.15 (1H, s); Mass spectrum (FAB), MH$^+$ 463, MNa$^+$ 485.

MIC against *P. mirabilis* 889 16.0 μg/ml (broth).

(c) Sodium 3-Carbamoyloxymethyl-7α-formamido-7β-thien-2-yl-acetamido-ceph-3-em-4-carboxylate-1-oxide Oxidation of sodium 3-carbamoyloxymethyl-7α-formamido-7β-thien-2-yl-acetamido-ceph-3-em-4-carboxylate with peracetic acid in analogous manner to that described in Example 6(d) gives the title compound as a mixture of R- and and S-sulphoxide isomers.

EXAMPLE 27

Sodium 7α-formamido-7-thien-2-ylacetamido-cephalosporanate-1β-oxide and sodium 7α-formamido-7β-thien-2-ylacetamido-cephalosporanate-1α-oxide (a) t-Butyl 7α-formamido-7β-thien-2-ylacetamido-cephalosporanate-1α and 1β-oxides t-Butyl 7α-formamido-7β-thien-2-ylacetamido-cephalosporanate (200 mg) was suspended in dry methylene dichloride (MDC) (15 ml) and cooled to −30° C., with stirring, and treated with 5.28% (w/v) peracetic acid/acetic acid (0.58 ml). The mixture was allowed to slowly warm to room temperature. After approximately 1 h (t.l.c. monitoring) the mixture was evaporated to dryness. The residue was chromatographed on silica gel (12 g) using MDC then ethyl acetate/MDC mixtures to elute the products, t-butyl 7α-formamido-7β-thien-2-ylacetamido-cephalosporanate-1β-oxide, (104 mg) (50%); m.p. (ethyl acetate/n-hexane) 152°–155° C.; $\nu_{max}$ (CHCl$_3$) 3390, 1795, 1690 and 1040 cm$^{-1}$, δppm (250M Hz) (CDCl$_3$) (major rotamer) 1.58 (9H, s), 2.08 (3H, s), 3.23 and 3.66 (2H, ABq, J 18 Hz), upper field ½ of ABq shows further coupling, J 1.6 Hz, which is lost on irradiation at 4.75), 3.85 (2H, s), 4.68 and 5.15 (2H, ABq, J 13 Hz), 4.75 (1H, d, J 1.6 Hz), 6.95 to 7.05 (2H, m), 7.20 to 7.30 (1H, m), 7.51 (1H, s, exch. D$_2$O), 7.66 (1H, s, exch. D$_2$O), 8.16 (1H, s). (Found C, 49.0; H, 4.8; N, 8.0; s, 12.3. C$_{21}$H$_{25}$N$_3$O$_8$S$_2$ requires C, 49.3, H, 4.9,; N, 8.2; 5, 12.5%). and t-butyl 7α-foramido-7β-thien-2-ylacetamido-cephalosporanate-1α-oxide, (73 mg) (35%); m.p. (ethyl acetate/n-hexane) 153°–156° C.; $\nu_{max}$ (CHCl$_3$) 3390 sh, 3250, 1800, 1730, 1685 and 1045 cm$^{-1}$; δppm (250 MHz) (CDCl$_3$) (major rotamer) 1.65 (9H, s), 2.11 (3H, s), 3.55 and 4.02 (2H, ABq, J 18 Hz), 3.87 (2H, s), 4.79 and 5.09 (2H, ABq, J 14 Hz), 4.94 (1H, s), 6.90 to 7.05 (2H, m), 7.20 to 7.30 (1H, m), 7.25 (1H, s, exch. D$_2$O), 8.10 (1H, s) 8.39 (1H, s, exch. D$_2$O). (Found C, 49.1; H 4.9; N, 8.1; s, 12.5%).

(b) Sodium 7α-Formamido-7β-thien-2-ylacetamidocephalosporanate-1β-oxide t-Butyl 7α-formamido-7β-thien-2-ylacetamido-cephalosporanate-1β-oxide (77 mg) was dissolved in trifluoroacetic acid (4 ml) and stirred at ambient temperature for approx. ½ h. The mixture was evaporated, dry toluene (2 ml) added and the mixture re-evaporated. The residue was dried at high vacuum for approx. 15 min then triturated with dry ether. The solid was washed with more ether (x 2), then dried in vacuo. The solid was suspended in water (1 ml) and the pH adjusted to 6.5 by the addition of saturated sodium bicarbonate solution. The resulting solution was chromatographed on 'Diaion' HP20SS, eluting with water, then acetone/water mixtures. Concentration and lyophilization of the relevant fraction gave the title compound (73 mg). $\nu_{max}$ (KBr) 3433, 3260, 1781, 1727, 1676, 1612 and 1041 cm$^{-1}$; δppm (250 MHz) (D$_2$O) (major rotamer) 2.11 (3H, s), 3.6 and 3.80 (together 2H, ABq, J 17.6 Hz, upper field ½ of ABq broadened), 3.98 (2H, AA', J 17 Hz), 4.67 and 4.85 (together 2H, ABq, J 13 Hz), 5.18 (1H, broad s), 7.00 to 7.12 (2H, m), 7.35 to 7.45 (1H, m), 8.14 (1H, s). Mass spectrum (FAB) MH$^+$ 478, MNa$^+$ 500. MIC against *P. mirabilis* 889 is 8.0 (μg/ml).

(c) Sodium 7α-Formamido-7β-thien-2-ylacetamidocephalosporanate-1α-oxide t-Butyl 7α-formamido-7β-thien-2-ylacetamidocephalosporanate-1α-oxide (75 mg) was treated with trifluoroacetic acid and worked up as in Example 27B to give the title compound (76 mg). $\nu_{max}$ (KBr) 3422, 3300, (sh), 1782, 1731, 1676, 1616, 1527 and 1037 cm$^{-1}$; δppm (250 MHz) (D$_2$O) (major rotamer) 2.12 (3H, s), 3.59 and 4.24 (together 2H, ABq, J 16 Hz), 3.94 and 4.01 (together 2H, ABq, J 6.5 Hz), 4.67 and 4.92 (together 2H, ABq, J 13 Hz), 5.06 (1H, s), 7.00 to 7.15 (2H, m), 7.35 to 7.46 (1H, m), 8.29 (1H, s).

Mass spectrum (FAB) MH$^+$ 478. MIC against *P. mirabilis* 889 is 2.0 μg/ml.

EXAMPLE 28

6α-Formamido-6β-[D-2-[D-2-amino-3-(N-methylcarbamoyl)propionamido]-2-(4-hydroxyphenyl)acetamido]penicillanic acid 1α-oxide.

(a) Benzyl 6α-formamido-6β-[D-2-[D-2-(4-nitrobenzyloxycarbonylamino)-3-(N-methylcarbamoyl)propionamido]-2-(4-benzyloxycarbonyloxyphenyl)acetamido]penicillanate.

A solution of benzyl 6α-formamido-6β-[D-2-(4-nitrobenzyloxycarbonylamino)-2-(4-benzyloxycarbonyloxyphenyl)acetamido]penicillanate (0.81 g, 1 mmol) in tetrahydrofuran (30 ml) was treated with 1M aqueous potassium dihydrogen phosphate (6 ml), then stirred vigorously at room temperature while freshly acid-washed zinc dust (2 g) was added. The pH of the solution was adjusted to 2.0 by dropwise addition of 2M aqueous hydrochloric acid and the course of the reduction was monitored by t.l.c. After 1 h, the starting material appeared to be completely consumed, as addition of further zinc dust caused no further change. The reaction mixture was filtered and the precipitated solid was well washed with ethyl acetate and water. The organic phase was separated and washed with water (2×50 ml) and brine, then dried over anhydrous magnesium sulphate. Concentration to ca. 10 ml afforded an ethyl acetate solution of the free α-amino penicillin, which was unstable and used at once without further purification; R$_F$ca. 0.2 in 10% methanol-chloroform with much streaking to higher R$_F$.

A portion of the above solution (5 ml, taken to contain 0.5 mmol of the free α-amino penicillin) was added slowly at 0° C. to a mixture of D-2-(4-nitrobenzyloxycarbonylamino)-3-(N-methylcarbamoyl)propionic acid (163 mg, 0.5 mmol), 1-hydroxybenzotriazole monohydrade (77 mg, 0.5 mmol) and N,N'-dicyclohexylcarbodi-imide (103 mg, 0.5 mmol) in tetrahydrofuran (3 ml). The solution was allowed to regain ambient temperature and stirred for 2 h, after which time no free α-amino penicillin could be detected by t.l.c. The precipitated solid was filtered and washed with ethyl acetate and tetrahydrofuran and the combined filtrate was washed sequentially with 0.5M hydrochloric acid solution (2×20 ml), saturated aqueous sodium hydrogen carbonate solution (2×20 ml), water and brine, then dried over anhydrous magnesium sulphate. Evaporation gave crude product (ca. 400 mg), which was subjected to chromatography on silica gel (40 g), eluting with 5% methanol in chloroform. Appropriate fractions were combined and evaporated to give the title penicillin ester (225 mg, 48%); $\nu_{max}$ (KBr) 1785, 1764, 1645, 1607 sh, 1519, 1453 cm$^{-1}$; $\delta[(CD_3)_2CO]$ 1.03, 1.19 [6H, 2s, (CH$_3$)$_2$C] 2.6–2.8 (5H, m, CH$\underline{CH_2}$CO+NH$\underline{CH_3}$), 4.41 (1H, s, 3-H), 4.80 (1H, m, t on D$_2$O exchange, $\underline{CH_2}$CHNH), 5.15–5.30 (6H, m, 3×Ar$\underline{CH_2}$O), 5.71 (1H, s, 5-$\underline{H}$), 5.89 (1H, d, s on D$_2$O exchange and shifting to $\delta$5.6, Ar$\underline{CH}$NH), 7.0–7.7 (17H, m, Ar$\underline{H}$+one NH, the latter D$_2$O exchanged), 8.18 (2H, brs, sharpened on D$_2$O exchange and becoming s, NH$\underline{CHO}$), 8.25, 8.42 and 9.04 (3H, brs+2 brd, all D$_2$O exchanged, 3×NH); R$_F$ 0.39 in 10% methanol-chloroform.

(b) Benzyl 6α-formamido-6β-[D-2-[D-2-(4-nitrobenzyloxycarbonylamino)-3-(N-methylcarbamoyl)propionamido]-2-(4-benzyloxycarbonyloxyphenyl)acetamido]penicillianate-1α-oxide.

Benzyl 6α-formamido-6β-[D-2-[D-2-(4-nitrobenzyloxycarbonylamino)-3-(N-methylcarbamoyl)propionamido]-2-(4-benzyloxycarbonyloxyphenyl)acetamido]penicillanate (215 mg, 0.23 mmol) was dissolved in anhydrous dichloromethane (5 ml) and cooled to 0° C. with stirring. 3-Chloroperbenzoic acid (44 mg, 1.1 eq) was added and stirring continued at the same temperature for 1 h, after which time no starting material was visible by t.l.c. The solution was poured into ethyl acetate (20 ml) and washed sequentially with saturated aqueous sodium hydrogen carbonate solution (2×20 ml), water and brine, then dried over anhydrous magnesium sulphate and evaporated to dryness. This crude product (215 mg) was subjected to chromatography on silica gel (22 g), eluting with 7% methanol in chloroform. Appropriate fractions were combined and evaporated to give the title penicillin 1α-oxide as the more polar, major product (158 mg, 72%); $\nu_{max}$ (KBr) 1794, 1759, 1653 br, 1607, 1517, 1453 cm$^{-1}$; $\delta[(CD_3)_2CO]$ 1.01, 1.16 [6H, 2s, (CH$_3$)$_2$C], 2.6–2.9 (5H, m, including d becoming s on D$_2$O exchange, CH$\underline{CH_2}$CO+NH$\underline{CH_3}$), 4.58 (1H, s, 3-H) 4.64 (1H, m, t on $\overline{D_2O}$ exchange, $\underline{CH_2}$CHNH), 5.09 (1H, s, 5-H), 5.15–5.30 (6H, 3m, 3×Ar$\underline{CH_2}$O), 5.73 (1H, d, s on D$_2$O exchange, Ar$\underline{CH}$NH), 7.0–7.7 (17H, m, 16H on D$_2$O exchange, Ar$\underline{H}$+one NH), 8.22 (3H, m, 2Ar H+NH$\underline{CHO}$), 8.30–8.60 (3H, brd+2 brs, all D$_2$O exchanged, 3×NH), and 9.20 (1H, br s, D$_2$O exchanged, NH); R$_F$ ca. 0.30 in 10% methanol-chloroform.

(c) 6α-Formamido-6β-[D-2-[D-2-amino-3-(N-methylcarbamoyl)propionamido]-2-(4-hydroxyphenyl)acetamido]penicillanic acid, 1α-oxide.

Benzyl 6α-formamido-6β-[D-2-(D-2-(4-nitrobenzyloxycarbonylamino)-3-(N-methylcarbamoyl)propionamido]-2-(4-benzyloxycarbonyloxyphenyl)acetamido]penicillanate-1α-oxide (150 mg, 0.16 mmol) was dissolved in tetrahydrofuran (8 ml) and water (2 ml) was added, followed by 10% palladium on charcoal catalyst (150 mg). The mixture was hydrogenated under ambient conditions for 3 h, after which time there was almost complete conversion to a single very polar material by t.l.c. Hydrogenation was resumed for a further 1 h with more catalyst (60 mg), after which the mixture was filtered and the precipitate washed well with water and tetrahydrofuran. The filtrate was concentrated to ca. 20 ml. and washed with three portions of ethyl acetate, discarding the organic washings. The aqueous solution was treated with activated charcoal to remove resistant traces of colloidal catalyst, which rendered it dark; after again filtering, washing with chloroform and discarding both the organic phase and the interface, the aqueous phase was reasonably clear. It was again filtered, concentrated to about 10 ml. and lyophilised, giving the title zwitterionic penicillin-1α-oxide (65 mg, 75%); $\nu_{max}$ 1784, 1670, 1610 sh, 1512 cm$^{-1}$; $\delta(D_2O)$ 1.04, 1.22 [6H, 2s, (CH$_3$)$_2$], 2.76 (3H, s, NCH$_3$), 2.6–2.8 (2H, m, CH$\underline{CH_2}$CO), 3.65 (1H, t, $\underline{CH}$ (NH$_3^+$)CH$_2$), 4.19 (1H, s, 3-$\underline{H}$), 5.13 (1H, s, 5-H), 5.35 (1H, s, Ar$\underline{CHN}$), 6.94 and 7.37 (4H, 2d, ArH), 8.16 (1H, s, NCHO); R$_F$ ea. 0 in n-butanol:acetic acid:water, 4:1:1, R$_F$ 0.63 in pyridine:n-butanol:acetic acid:water, 15:10:3:12.

EXAMPLE 29

6α-Formamido-6β-[D-2-[(4-ethyl-2,3-dioxopiperazin-1-yl)carbonylamino]-2-(4-hydroxyphenyl)acetamido]-penicillanic acid 1α-oxide, sodium salt.

(a) Benzyl 6α-formamido-6β-[D-2-[(4-ethyl-2,3-dioxopiperazin-1-yl)carbonylamino]-2-(4-benzyloxycarbonyloxyphenyl)acetamido]penicillanate-1α-oxide.

A solution of benzyl 6α-formamido-6β-[D-2-[(4-ethyl-2,3-dioxopiperazin-1-yl)carbonylamino]-2-(4-benzyloxycarbonyloxyphenyl)acetamido]penicillanate (260 mg, 0.33 mmol) in anhydrous dichloromethane (5 ml) was cooled to 0° C. and stirred while 3-chloroperbenzoic acid (62 mg, 0.36 mmol) was added. The solution was stirred at the same temperature for 1 h, after which t.l.c. analysis showed complete consumption of the starting material. It was then poured into ethyl acetate (20 ml) and washed sequentially with saturated aqueous sodium hydrogen carbonate (2×20 ml), water and brine, then dried over anhydrous magnesium sulphate. Evaporation gave the crude product (ca. 230 mg), which was subjected to chromatography on silica gel (23 g). Elution with 5% methanol in chloroform afforded, after pooling and evaporation of appropriate fractions, the title α-sulphoxide as the major (most polar) product (173 mg, 65%); $\nu_{max}$ (KBr) 1794, 1758, 1715, 1683, 1504, and 1457 cm$^{-1}$; $\delta[(CD_3)_2CO]$ 0.92, 1.16 [6H, 2s, (CH$_3$)$_2$C], 1.19 (3H, t, $\underline{CH_3}$CH$_2$N), 3.4–4.1 (6H, 3 m, 3×NCH$_2$), 4.60 (1H, s, 3-$\underline{H}$), 5.05 (1H, s, 5-H), 5.21, 5.30 (4H, ABq+s, 2×Ph$\underline{CH_2}$O), 5.75 (1H, d, s on D$_2$O exchange, Ph $\underline{CH}$ NH), 7.20–7.75 (14H, m, ArH), 8.23 (1H, s, sharpened on D$_2$O exchange, NH$\underline{CHO}$), 8.57, 9.25 and 10.12 (3H, 2 brs+d, all D$_2$O exchanged, 3×NH).

(b) 6α-Formamido-6β-[D-2-[(4-ethyl-2,3-dioxopiperazin-1-yl)carbonylamino]-2-(4-hydroxyphenyl)acetamido]penicillanic acid 1α-oxide, sodium salt.

Benzyl 6α-formamido-6β-[D-2[(4-ethyl-2,3-dioxopiperazin-1-yl)carbonylamino]-2-(4-benzyloxycarbonyloxyphenyl)acetamido]penicillanate-1α-oxide(160 mg, 0.20 mmol) was dissolved in anhydrous tetrahydrofuran (10 ml) and 10% palladium on charcoal (100 mg) was added under argon. The mixture was hydrogenated under ambient conditions for 2.25 h, after which time a little starting material remained (t.l.c). Further catalyst (80 mg) was added and the hydrogenation was resumed for a further 2 h, after which there was virtually complete conversion to a single polar material (t.l.c). The mixture was filtered and the precipitate well washed with tetrahydrofuran. The filtrate was evaporated to dryness and redissolved in acetone containing sufficient tetrahydrofuran for solubility, then a solution of sodium 2-ethylhexanoate in 4-methylpentan-2-one (1 eq.) was added. The resulting precipitate was filtered, well washed with acetone: ether 1:1, ether, and dried to afford the title penicillin sodium salt (82 mg, 68%). This material was further purified by dissolving in a small volume of methanol, then filtered into a large, well-stirred excess of anhydrous ether, and the spectral and biological data relate to this product: $\nu_{max}$ (KBr) 1782, 1715, 1676, 1612, and 1512 cm$^{-1}$; $\delta$(D$_2$O) 1.03, 1.22 [6H, 2s, (CH$_3$)$_2$C] 1.20 (3H, t, $\underline{CH_3}$CH$_2$N), 3.4–4.1 (6H, 3 m, 3×NCH$_2$) 4.20 (1H, s, 3-$\overline{H}$), 5.14 (1H, s, 5-H), 5.38 (1H, s, PhCHN), 6.92, 7.38 (4H, 2d, ArH), 8.17 (1H, s, NC$\overline{HO}$); R$_f$ 0.15 in n-butanol:acetic acid:water, 4:1:1.

I claim:

1. A compound of Formula (I):

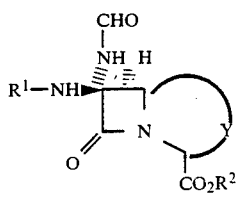

or a salt thereof wherein R$^1$ is hydrogen, an acyl group, or an amino-protecting group; R$^2$ is hydrogen or a readily removable carboxyl protecting group; and Y is:

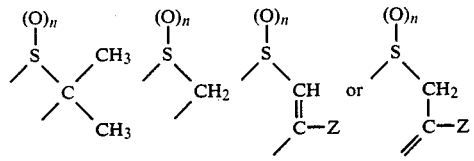

wherein n is 1 or 2 and Z is hydrogen, halogen, alkoxy of 1 to 4 carbon atoms, —CH$_2$Q or —CH=CH—Q wherein Q is hydrogen, halogen, hydroxy, mercapto, cyano, carboxy, carboxylic ester, carbamoyloxy, alkyloxy of 1 to 4 carbon atoms, acyloxy, aryl, a heterocyclyl group bonded via carbon, a heterocyclythio group or a nitrogen containing heterocyclic group bonded via nitrogen.

2. A compound according to claim 1 wherein n is 1.

3. A compound according to claim 1 wherein Y is:

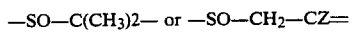

4. A compound according to claim 1 of the Formula (II):

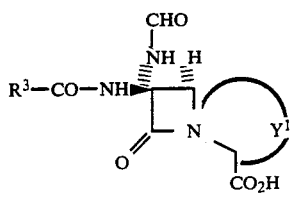

or a pharmaceutically acceptable salt or in vivo hydrolysable ester thereof wherein R$^3$ is a group such that R$^3$—CO—NH— is an acylamino group, as found in antibacterially active penicillins or cephalosporins and Y$^1$ is:

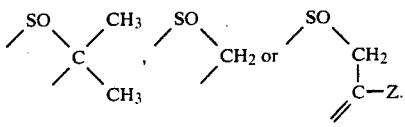

5. A compound according to claim 4 of Formula (III):

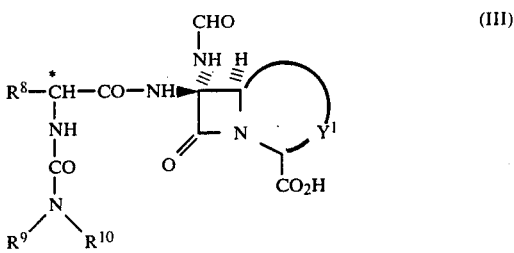

or a pharmaceutically acceptable salt or in vivo hydrolysable ester thereof wherein R$^8$ is phenyl, unsubstituted or substituted by up to 3 groups selected from alkyl of 1 to 6 carbon atoms, phenyl, halogen, alkoxy of 1 to 6 carbon atoms, amino, nitro, hydroxy, alkylamino or 1 to 6 carbon atoms, alkylcarbonyloxy of 1 to 6 carbon atoms, carboxy, alkoxycarbonyl of 1 to 6 carbon atoms, haloalkyl or 1 to 6 carbon atoms, oxoalkyl of 1 to 6 carbon atoms, alkylcarbonyl of 1 to 6 carbon atoms, aryloxy, aralkyloxy, arylcarbonyl, or dialkylamino or 1 to 6 carbon atoms in each alkyl moiety, cyclohexenyl, cyclohexadienyl or a 5- or 6-membered heterocyclic ring containing up to three hetero-atoms selected from oxygen, sulphur or nitrogen, unsubstituted or substituted with hydroxy, amino, halogen, substituted amino or alkoxy of 1 to 6 carbon atoms; R$^9$ is hydrogen or alkyl of 1 to 6 carbon atoms and R$^{10}$ is a 5- or 6-membered heterocyclic group containing one or two nitrogen heteroatoms unsubstituted or substituted by alkenyl, alkynyl, cycloalkyl, phenyl, oxo, hydroxy unsubstituted or substituted by alkyl, alkenyl, cycloalkyl, phenyl, pyridyl, pyrimidyl, or benzyl, mercapto, alkylsulphonyl, imino, or amino unsubstituted or substituted by alkyl, alkenyl, cycloalkyl, phenyl or benzyl; or R$^9$ and R$^{10}$ together with the nitrogen atom to which they are attached form a five- or six-membered heterocyclic group containing one or two nitrogen heteroatoms unsubstituted or substituted by alkenyl, alkynyl, cycloalkyl, phenyl, oxo, hydroxy unsubstituted or substituted by alkyl, alkenyl, cycloalkyl, phenyl, pyridyl, pyrimidyl, or benzyl, mercapto, alkylsulphonyl, imino, or amino unsubstituted or substituted by alkyl, alkenyl, cycloalkyl, phenyl or benzyl.

6. A compound selected from the following or a pharmaceutically acceptable salt or in vivo hydrolysable ester thereof:

7β-[D-2-[(4-Ethyl-2,3-dioxopiperazin-1-yl)carbonylamino]-2-(3,4-diacetoxyphenyl)acetamido]-7α-formamidocephalosporanic acid-1-oxide;

7β-[D-2-[(4-Ethyl-2,3-dioxopiperazin-1-yl)carbonylamino]-2-phenylacetamido]-7α-formamidocehalosporanic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1-oxide;

7β-[D-2-(3,4-Diacetoxyphenyl)-2-[(4-ethyl-2,3-diox-opiperazin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-(3,4-Dihydroxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-[(4-Ethyl-2,3-dioxopiperazin-1-yl)carbonylamino]-2-phenylacetamido]-7α-formamido-3-pyridiniummethyl-ceph-3-em-4-carboxylate-1-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1α-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1β-oxide;

α-Formamido-6β-(phenylacetamido)penicillanic acid-1β-oxide;

7β-[D-2-[(4-Ethyl-2,3-dioxopiperazin-1-yl)carbonylamino]-2-(4-hydroxyphenyl)acetamido]-7α-formamidocephalosporanic acid-1-oxide;

3-[(1-Carboxymethyl-1H-tetrazol-5-yl)thiomethyl]-7β-[D-2-(3,4-diacetoxyphenyl)-2-[(4-ethyl-2,3-dioxopiperazin-1-yl)carbonylamino]acetamido]-7α-formamidoceph-3-em-4-carboxylic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1α-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1β-oxide;

6β-(Phenoxyacetamido)-6α-formamidopenicillanic acid-1-oxide;

6β-[D-2[(4-Ethyl-2,3-dioxopiperazin-1-yl)carbonylamino]-2-phenylacetamido]-6α-formamidopenicillanic acid-1-oxide;

6β-(D-2-Amino-2-phenylacetamido)-6α-formamidopenicillanic acid-1-oxide;

6β-[D-2-(4-Hydroxyphenyl)-2-[(3-(methylsulphonyl)-2-oxoimidazolidin-1-yl]carbonylamino]acetamido]-6α-formamidopenicillanic acid-1-oxide;

7α-Formamido-7β-(thien-2-ylacetamido)cephalosporanic acid-1β-oxide;

7α-Formamido-7β-(thien-2-ylacetamido)cephalosporanic acid-1α-oxide;

3-Carbamoyloxymethyl-7α-formamido-7β-(thien-2-ylacetamido)ceph-3-em-4-carboxylic acid-1-oxide;

6α-Formamidopenicillanic acid-1-oxide;

7β-[D-2-[(4-Ethyl-2,3-dioxopiperazin-1-yl)carbonylamino]-2-phenylacetamido]-7α-formamidocephalosporanic acid-1,1-dioxide; or 6β-[D-2-[(4-Ethyl-2,3-dioxopiperazin-1-yl)carbonylamino]-2-(3,4-diacetoxyphenyl)acetamido]-6α-formamidopenicillanic acid-1,1dioxide.

7. A method of treating bacterial infections in humans and animals which comprises administering to a human or animal in need thereof and antibacterially effective amount of a compound of claim 4 in combination with a pharmaceutically acceptable carrier.

8. A pharmaceutical composition useful for treating bacterial infections in humans and animals and for effecting β-Lactamase inhibitory activity in humans and animals which comprises a therapeutically effect amount of a compound of the formula (I):

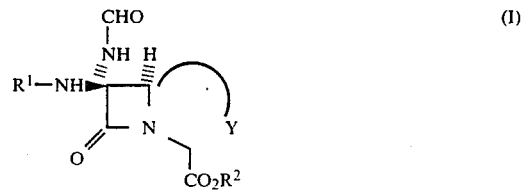

or a pharmaceutically acceptable salt thereof wherein $R^1$ is hydrogen, an acyl group, or an amino-protecting group; $R^2$ is hydrogen or a readily removable carboxyl protecting group; and Y is:

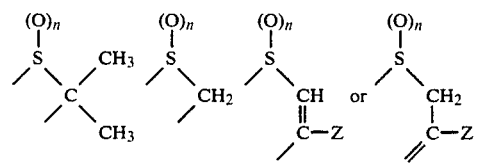

wherein n is 1 or 2 and Z is hydrogen, halogen, alkoxy of 1 to 4 carbon atoms, $-CH_2Q$ or $-CH=CH-Q$ where Q is hydrogen, halogen, hydroxy, mercapto, cyano, carboxy, carboxylic ester, carbamoyloxy, alkyloxy of 1 to 4 carbon atoms, acyloxy, aryl, a heterocyclyl group bonded via carbon, a hetrocyclythio group or a nitrogen containing heterocyclic group bonded via nitrogen, in combination with a pharmaceutically acceptable carrier.

9. A composition according to claim 8 wherein n is 1.

10. A composition according to claim 8 wherein Y is:

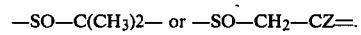

$-SO-C(CH_3)_2-$ or $-SO-CH_2-CZ=$.

11. A composition according to claim 8 wherein the compound is of the formula (II):

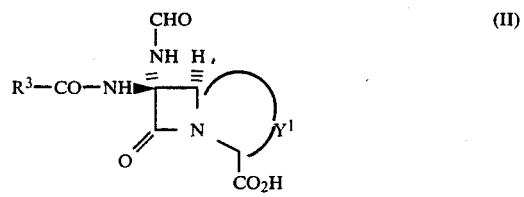

or a pharmaceutically acceptable salt or in vivo hydrolysable ester thereof wherein $R^3$ is a group such that $R^3-CO-NH-$ is an acylamino group, as found in antibacterially active penicillins or cephalosporins and $Y^1$ is:

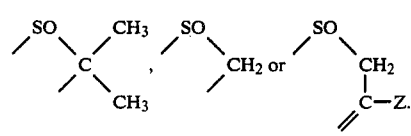

12. A composition according to claim 8 wherein the compound is the of Formula (III):

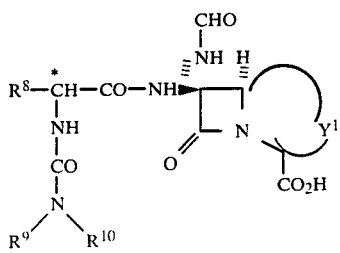

(III)

or a pharmaceutically acceptable salt or in vivo hydrolysable ester thereof wherein $R^8$ is phenyl, unsubstituted or substituted by up to 3 groups selected from alkyl of 1 to 6 carbon atoms, phenyl, halogen, alkoxy of 1 to 6 carbon atoms, amino, nitro, hydroxy, alkylamino of 1 to 6 carbon atoms, alkylcarbonyloxy of 1 to 6 carbon atoms, carboxy, alkoxycarbonyl of 1 to 6 carbon atoms, haloalkyl or 1 to 6 carbon atoms, oxoalkyl of 1 to 6 carbon atoms, alkylcarbonyl of 1 to 6 carbon atoms, aryloxy, aralkyloxy, arylcarbonyl, or dialkylamino or 1 to 6 carbon atoms in each alkyl moiety, cyclohexenyl, cyclohexadienyl, or a 5- or 6-membered heterocyclic ring containing up to three hetero-atoms selected from oxygen, sulphur or nitrogen, unsubstituted or substituted with hydroxy, amino, halogen, substituted amino or alkoxy of 1 to 6 carbon atoms; $R^9$ is hydrogen or alkyl of 1 to 6 carbon atoms and $R^{10}$ is a 5- or 6-membered heterocyclic group containing one or two nitrogen heteroatoms unsubstituted or substituted by alkenyl, alkynyl, cycloalkyl, phenyl, oxo, hydroxy unsubstituted or substituted by alkyl, alkenyl, cycloalkyl, phenyl, pyridyl, pyrimidyl, or benzyl, mercapto, alkylsulphonyl, imino, or amino unsubstituted or substituted by alkyl, alkenyl, cycloalkyl, phenyl or benzyl; or $R^9$ and $R^{10}$ together with the nitrogen atom to which they are attached form a five- or six-membered heterocyclic group containing one or two nitrogen heteroatoms unsubstituted or substituted by alkenyl, alkynyl, cycloalkyl, phenyl, oxo, hydroxy unsubstituted or substituted by alkyl, alkenyl, cycloalkyl, phenyl, pyridyl, pyrimidyl, or benzyl, mercapto, alkylsulphonyl, imino, or amino unsubstituted or substituted by alkyl, alkenyl, cycloalkyl, phenyl or benzyl.

13. A composition according to claim 8 wherein the compound is:

7β-[D-2-[(4-Ethyl-2,3-dioxopiperazin-1-yl)carbonylamino]-2-(3,4-diacetoxyphenyl)acetamido]-7α-formamidocephalosporanic acid-1-oxide;

7β-[D-2-[(4-Ethyl-2,3-dioxopiperazin-1-yl)carbonylamino]-2-phenylacetamido]-7α-formamidocephalosporanic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1-oxide;

7β-[D-2-(3,4-Diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-(3,4-Dihydroxyphenyl)-2-[(4-ethyl-2,3-dioxopipe razin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-[(4-Ethyl-2,3-dioxopiperazin-1-yl)carbonylamino]-2-phenylacetamido]-7α-formamido-3-pyridiniummethyl-ceph-3-em-4-carboxylate-1-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1α-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1β-oxide;

6α-Formamido-6β-(phenylacetamido)penicillanic acid-1β-oxide;

7β-[D-2-[(4-Ethyl-2,3-dioxopiperazin-1-yl)carbonylamino]2-(4-hydroxyphenyl)acetamido]-7α-formamidocephalosporanic acid-1-oxide;

3-[(1-Carboxymethyl-1H-tetrazol-5-yl)thiomethyl]-7β-[D-2-(3,4-diacetoxyphenyl)-[(4-ethyl-2,3-dioxopiperazin-1-yl)carbonylamino]acetamido]-7α-formamidoceph-3-em-4-carboxylic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1α-oxide;

6β-[D-2-[(4-Ethyl-2,3-dioxopiperazin-1-yl)carbonylamino]2-(3,4-diacetoxyphenyl)acetamido]-6α-formamidopenicillanic acid-1β-oxide;

6β-(Phenoxyacetamido)-6α-formamidopenicillanic acid-1-oxide;

6β-[D-2[(4-Ethyl-2,3-dioxopiperazin-1-yl)carbonylamino]-2-phenylacetamido]-6α-formamidopenicillanic acid-1-oxide;

6β-(D-2-Amino-2-phenylacetamido)-6α-formamidopenicillanic acid-1-oxide;

6β-[D-2-(4-Hydroxyphenyl)-2-[(3-(methylsulphonyl)-2-oxoimidazolidin-1-yl]carbonylamino]acetamido]-6α-formamidopenicillanic acid-1-oxide;

7α-Formamido-7β-(thien-2-ylacetamido)cephalosporanic acid-1β-oxide;

7α-Formamido-7β-(thien-2-ylacetamido)cephalosporanic acid-1α-oxide;

3-Carbamoyloxymethyl-7α-formamido-7β-(thien-2-ylacetamido)ceph-3-em-4-carboxylic acid-1-oxide;

6α-Formamidopenicillanic acid-1-oxide;

7β-[D-2-[(4-Ethyl-2,3-dioxopiperazin-1-yl)carbonylamino]-2-phenylacetamido]-7α-formamidocephalosporanic acid-1,1-dioxides; or 6β-[D-2-[(4-ethyl-2,3-dioxopiperazin-1-yl)carbonylamino]-2-(3,4-diacetoxyphenyl)acetamido]6α-formamidopenicillanic acid-1,1-dioxide, or a pharmaceutically acceptable salt or in vivo hydrolysable ester thereof.

14. A method for treating bacterial infections in humans and animals and for effecting β-Lactamase inhibitory activity in humans and animals which comprises administering to a human or animal in need thereof a therapeutically effective amount of a compound of the Formula (I):

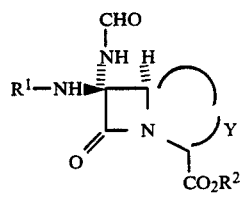

(I)

or a pharmaceutically acceptable salt thereof wherein $R^1$ is hydrogen, an acyl group, or an amino-protecting group; $R^2$ is hydrogen or a readily removable carboxyl protecting group; and Y is:

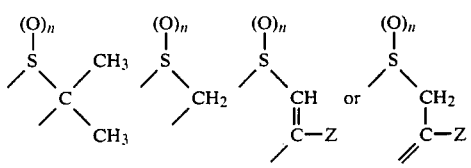

wherein n is 1 or 2 and Z is hydrogen, halogen, alkoxy of 1 to 4 carbon atoms, —CH$_2$Q or —CH=CH—Q wherein Q is hydrogen, halogen, hydroxy, mercapto, cyano, carboxy, carboxylic acid, carbamoyloxy, alkyloxy of 1 to 4 carbon atoms, acyloxy, aryl, a heterocyclyl group bonded via carbon, a heterocyclythio group or a nitrogen containing heterocyclic group bonded via nitrogen, in combination with a pharmaceutically acceptable carrier.

15. A method according to claim 14 wherein n is 1.
16. A method according to claim 14 wherein Y is:

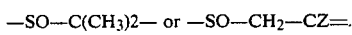

17. A method according to claim 14 wherein the compound is of the formula (II):

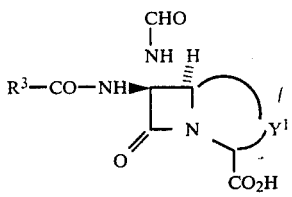

or a pharmaceutically acceptable salt or in vivo hydrolysable ester thereof wherein $R^3$ is a group such that $R^3$—CO—NH— is an acylamino group, as found in antibacterially active penicillins or cephalosporins and $Y^1$ is:

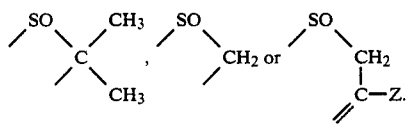

18. A method according to claim 14 wherein the compound is the of Formula (III):

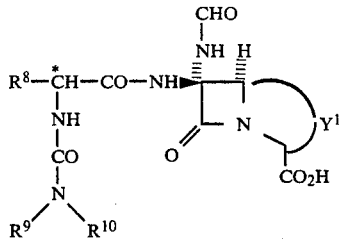

or a pharmaceutically acceptable salt or in vivo hydrolysable ester thereof wherein $R^8$ is phenyl, unsubstituted or substituted by up to 3 groups selected from alkyl of 1 to 6 carbon atoms, phenyl, halogen, alkoxy of 1 to 6 carbon atoms, amino, nitro, hydroxy, alkylamino of 1 to 6 carbon atoms, alkylcarbonyloxy of 1 to 6 carbon atoms, carboxy, alkoxycarbonyl of 1 to 6 carbon atoms, haloalkyl or 1 to 6 carbon atoms, oxoalkyl of 1 to 6 carbon atoms, alkylcarbonyl of 1 to 6 carbon atoms, aryloxy, aralkyloxy, arylcarbonyl, or dialkylamino or 1 to 6 carbon atoms in each alkyl moiety, cyclohexenyl, cyclohexadienyl, or a 5- or 6-membered heterocyclic ring containing up to three hetero-atoms selected from oxygen, sulphur or nitrogen, unsubstituted or substituted with hydroxy, amino, halogen, substituted amino or alkoxy of 1 to 6 carbon atoms; $R^9$ is hydrogen or alkyl of 1 to 6 carbon atoms and $R^{10}$ is a 5- or 6-membered heterocyclic group containing one or two nitrogen heteroatoms unsubstituted or substituted by alkenyl, alkynyl, cycloalkyl, phenyl, oxo, hydroxy unsubstituted or substituted by alkyl, alkenyl, cycloalkyl, phenyl, pyridyl, pyrimidyl, or benzyl, mercapto, alkylsulphonyl, imino, or amino unsubstituted or substituted by alkyl, alkenyl, cycloalkyl, phenyl or benzyl; or $R^9$ and $R^{10}$ together with the nitrogen atom to which they are attached form a five- or six-membered heterocyclic group containing one or two nitrogen heteroatoms unsubstituted or substituted by alkenyl, alkynyl, cycloalkyl, phenyl, oxo, hydroxy unsubstituted or substituted by alkyl, alkenyl, cycloalkyl, phenyl, pyridyl, pyrimidyl, or benzyl, mercapto, alkylsulphonyl, imino, or amino unsubstituted or substituted by alkyl, alkenyl, cycloalkyl, phenyl or benzyl.

19. A method according to claim 14 wherein the compound is:

7β-[D-2-[(4-Ethyl-2,3-dioxopiperazin-1-yl)carbonylamino]-2-(3,4-diacetoxyphenyl)acetamido]-7α-formamidocephalosporanic acid-1-oxide;

7β-[D-2-[(4-Ethyl-2,3-dioxopiperazin-1-yl)carbonylamino]-2-phenylacetamido]-7α-formamidocephalosporanic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1-oxide;

7β-[D-2-(3,4-Diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-(3,4-Dihydroxyphenyl)-2-[(4-ethyl-2,3-dioxopipe razin-1-yl)carbonylamino]acetamido]-7α-formamido-3-[(1-methyl-1H-tetrazol-5-yl)thiomethyl]-ceph-3-em-4-carboxylic acid-1-oxide;

7β-[D-2-[(4-Ethyl-2,3-dioxopiperazin-1-yl)carbonylamino]-2-phenylacetamido]-7α-formamido-3:pyridiniummethyl-ceph-3-em-4-carboxylate-1-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1α-oxide;

7β-[D-2-[(4-Ethyl-2,3-dioxopiperazin-1-yl)carbonylamino]-2-phenylacetamido]-7α-formamido-3-[(1-methyl-1H-tetrazol-5-yl)thiomethyl]-ceph-3-em-4-carboxylic acid-1β-oxide;

6α-Formamido-6β-(phenylacetamido)penicillanic acid-1β-oxide;

7β-[D-2-[(4-Ethyl-2,3-dioxopiperazin-1-yl)carbonylamino]-2-(4-hydroxyphenyl)acetamido]-7α-formamidocephalosporanic acid-1-oxide;

3-[(1-Carboxymethyl-1H-tetrazol-5-yl)thiomethyl-7β-[D-2-(3,4-diacetoxyphenyl)-[(4-ethyl-2,3-dioxopiperazin-1-yl)carbonylamino]acetamido]-7α-formamidoceph-3-em-4-carboxylic acid-1-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1α-oxide;

6β-[D-2-[(4-Ethyl-2,3-dioxopiperazin-1-yl)carbonylamino]-2-(3,4-diacetoxyphenyl)acetamido]-6α-formamidopenicillanic acid-1β-oxide;
6β-(Phenoxyacetamido)-6α-formamidopenicillanic acid-1-oxide;
6β-[D-2-[(4-Ethyl-2,3-dioxopiperazin-1-yl)carbonylamino]-2-phenylacetamido]-6α-formamidopenicillanic acid-1-oxide;
6β-(D-2-Amino-2-phenylacetamido)-6α-formamidopenicillanic acid-1-oxide;
6β-[D-2-(4-Hydroxyphenyl)-2-[(3-(methylsulphonyl)-2-oxoimidazolidin-1-yl]carbonylamino]acetamido]-6α-formamidopenicillanic acid-1-oxide;
7α-Formamido-7β-(thien-2-ylacetamido)cephalosporanic acid-1β-oxide;
7α-Formamido-7β-(thien-2-ylacetamido)cephalosporanic acid-1α-oxide;
3-Carbamoyloxymethyl-7α-formamido-7β-(thien-2-ylacetamido)ceph-3-em-4-carboxylic acid-1-oxide;
6α-Formamidopenicillanic acid-1-oxide;
7β-[D-2-[(4-Ethyl-2,3-dioxopiperazin-1-yl)carbonylamino]-2-phenylacetamido]-7α-formamidocephalosporanic acid-1,1-dioxide; or
6β-[D-2-[(4-ethyl-2,3-dioxopiperazin-1-yl)carbonylamino]-2-(3,4-diacetoxyphenyl)acetamido]6α-formamidopenicillanic acid-1,1-dioxide,
or a pharmaceutically acceptable salt or in vivo hydrolysable ester thereof.

* * * * *